US012781242B2

(12) United States Patent
Brown et al.

(10) Patent No.: US 12,781,242 B2
(45) Date of Patent: Nov. 3, 2026

(54) TRANSGENIC CORN EVENT MON95275 AND METHODS FOR DETECTION AND USES THEREOF

(71) Applicant: Monsanto Technology LLC, St. Louis, MO (US)

(72) Inventors: Sarah L. Brown, Weldon Spring, MO (US); Stanislaw Flasinski, Ballwin, MO (US); Aihong Pan, St. Louis, MO (US); Jason W. Stelzer, Wildwood, MO (US); Heidi M. Windler, Fenton, MO (US); Yong Yin, Creve Coeur, MO (US)

(73) Assignee: Monsanto Technology LLC, St. Loius, MO (US)

( * ) Notice: Subject to any disclaimer, the term of this patent is extended or adjusted under 35 U.S.C. 154(b) by 64 days.

(21) Appl. No.: 18/957,316

(22) Filed: Nov. 22, 2024

(65) Prior Publication Data

US 2025/0092417 A1 Mar. 20, 2025

Related U.S. Application Data

(62) Division of application No. 17/829,963, filed on Jun. 1, 2022, now Pat. No. 12,188,034, which is a division of application No. 17/235,129, filed on Apr. 20, 2021, now Pat. No. 11,578,339.

(60) Provisional application No. 63/014,771, filed on Apr. 24, 2020.

(51) Int. Cl.
*C12N 15/82* (2006.01)
*C12Q 1/6895* (2018.01)

(52) U.S. Cl.
CPC ....... *C12N 15/8286* (2013.01); *C12Q 1/6895* (2013.01); *C12Q 2600/13* (2013.01); *C12Q 2600/158* (2013.01)

(58) Field of Classification Search
None
See application file for complete search history.

(56) References Cited

U.S. PATENT DOCUMENTS

| | | | |
|---|---|---|---|
| 7,750,207 B2 | 7/2010 | Wu et al. | |
| 7,943,818 B2 | 5/2011 | Fillatti et al. | |
| 9,365,863 B2 | 6/2016 | Burns et al. | |
| 9,617,553 B2 | 4/2017 | Flasinski et al. | |
| 9,719,145 B2 | 8/2017 | Beazley et al. | |
| 10,100,330 B2 | 10/2018 | Bowen et al. | |
| 10,316,330 B2 | 6/2019 | Burns et al. | |
| 11,578,339 B2 | 2/2023 | Brown et al. | |
| 12,188,034 B2 | 1/2025 | Brown et al. | |
| 2004/0018518 A1 | 1/2004 | Krieb et al. | |
| 2013/0031672 A1 | 1/2013 | Flasinski et al. | |
| 2013/0340111 A1* | 12/2013 | Burns | C12N 15/8286 426/627 |
| 2015/0274786 A1 | 10/2015 | Bowen et al. | |
| 2016/0319302 A1 | 11/2016 | Bean et al. | |
| 2018/0363067 A1 | 12/2018 | Barbour et al. | |
| 2019/0136331 A1 | 5/2019 | Diehn et al. | |
| 2019/0153468 A1 | 5/2019 | Bean et al. | |
| 2019/0352726 A1 | 11/2019 | Bezaley et al. | |
| 2021/0017531 A1 | 1/2021 | Davis | |
| 2021/0332380 A1 | 10/2021 | Brown et al. | |
| 2023/0332171 A1 | 10/2023 | Brown et al. | |
| 2026/0028641 A1 | 1/2026 | Brown et al. | |

FOREIGN PATENT DOCUMENTS

| | | |
|---|---|---|
| CA | 3057145 A1 | 10/2018 |
| WO | 2004011601 | 2/2004 |
| WO | 2005103301 | 11/2005 |
| WO | 2011075586 | 6/2011 |
| WO | 2020028172 A1 | 2/2020 |

OTHER PUBLICATIONS

International Search Report and Written Opinion regarding International App. No. PCT/US2021/028189, mailed Sep. 21, 2021.
Fourgoux-Nicol et al., Plant Mol. Biol. (1999) 40:857-872.
GenBank Accession No. MH973511, dated Nov. 12, 2018.
Extended European Search Report regarding EP App. 21792059.4, dated May 14, 2024.
Gryson et al., Anal. Bioanal. Chem (2010) 396:2003-2022.
Devine, Why are there not more herbicide-tolerant crops?, Pest Management Science 61:312-317, 2005.

* cited by examiner

*Primary Examiner* — Mykola V. Kovalenko
(74) *Attorney, Agent, or Firm* — Dentons US LLP; David Lanzotti

(57) ABSTRACT

The invention provides a transgenic corn event MON95275, plants, plant cells, seeds, plant parts (including pollen, seed, and cells, and tissues corresponding to tassel, root, stalk, stem, leaf, cobb, and the like), progeny plants, commodity products comprising detectable amounts of corn event MON95275 DNA. The invention also provides polynucleotides specific for corn event MON95275 and methods for using and detecting corn event MON95275 DNA as well as plants, plant cells, seeds, plant parts, progeny plants, and commodity products comprising corn event MON95275. The invention also provides methods related to making and using corn event MON95275.

3 Claims, 3 Drawing Sheets

Specification includes a Sequence Listing.

TRANSGENIC CORN EVENT MON95275 AND METHODS FOR DETECTION AND USES THEREOF

CROSS-REFERENCE TO RELATED APPLICATIONS

This application is a divisional of U.S. patent application Ser. No. 17/829,963, filed Jun. 1, 2022, which is a divisional of U.S. patent application Ser. No. 17/235,129, filed Apr. 20, 2021, now U.S. Pat. No. 11,578,339, which claims the benefit of priority to U.S. Provisional Application Ser. No. 63/014,771, filed Apr. 24, 2020, which claims the benefit of U.S. provisional application No. 63/014,771, filed Apr. 24, 2020, each of which is herein incorporated by reference in its entirety.

INCORPORATION OF SEQUENCE LISTING

The sequence listing contained in the file named MONS480USD2_ST26.xml is 89,393 bytes (measured in Microsoft Windows®), was created on Nov. 21, 2024, is filed herewith by electronic submission, and is incorporated by reference.

FIELD OF THE INVENTION

The invention relates to recombinant DNA molecules present in and/or isolated from corn event MON95275. The invention also relates to transgenic corn plants, plant parts, and seed, pollen, cells, and agricultural products containing corn event MON95275, as well as methods of using the same, and detecting the presence of corn event MON95275 in samples containing corn. Transgenic corn plants, plant parts, seed and cells containing corn event MON95275 DNA exhibit resistance to infestations by insects in the family Coleoptera.

BACKGROUND OF THE INVENTION

Corn (*Zea mays*) is an important crop and is a primary food source in many areas of the world. The methods of biotechnology have been applied to corn for improving agronomic traits and product quality. One such agronomic trait is insect resistance, manifested through the insertion of a recombinant DNA segment into the genome of the corn plant.

There are a number of different transgenic events in corn that have been described in the art that provide various types of insect resistance, particularly to Lepidopteran or Coleopteran species, and these include MON810, TC1507, MON89034, MON95379, and MIR 162 among those that confer Lepidopteran resistance, and MON863, MON88017, DAS-59122-7, DP-004114-3, and DP23211 and MIR604 among those that confer Coleopteran resistance, particularly resistance to corn rootworm infestations. These transgenic events have been in use commercially in a variety of geographies across the glove for an extended period of time, often have used the same or similar toxins that were in use in earlier deployed transgenic events, and resistance to the expressed toxins in these events by targeted insect pests has been observed in many geographic regions where these have been deployed.

Thus, there is a continuing need in the art to provide novel transgenic events in corn that exhibit resistance to insect infestation, and preferably the novel transgenic events confer resistance to the target insects, including those races that have evolved resistance to the existing commercially deployed traits, using modes of action that are not overlapping with or similar to the modes of action previously deployed in earlier commercial embodiments. The inventions described herein are one example of such a novel transgenic event that confers resistance to corn rootworm infestations, including resistance to rootworms that have evolved resistance to commercial embodiments that have been previously deployed.

SUMMARY OF THE INVENTION

In one embodiment, the invention provides a novel transgenic corn event—MON95275—that provides insecticidal control over Coleopteran pests of corn. In a further embodiment, the invention also provides transgenic plant, plant cells, seed, plant parts, pollen and commodity products that contain the DNA that is specifically and identifiably present in corn event MON95275 and not present in corn that does not contain this particular event. This event specific DNA is the inserted transgenic DNA and the novel DNA segments that are described herein as the junction sequences formed at the chromosomal breakpoints at which the inserted DNA has been introduced. In another embodiment, the invention provides polynucleotides specific for corn event MON95275 and plant, plant cells, seed, plant parts, pollen, progeny plants, and commodity products comprising event MON95275 DNA. In yet another embodiment, methods related to enabling the selection and detection of the presence (or absence) of corn event MON95275 in a sample are provided, such methods providing for the investigator to confirm that the event DNA is, or is not, present in a particular sample subjected to the method.

Thus, in one aspect, the invention provides a recombinant DNA molecule comprising a nucleotide sequence selected from the group consisting of SEQ ID NO:1, SEQ ID NO:2, SEQ ID NO: 3, SEQ ID NO:4, SEQ ID NO:5, SEQ ID NO:6, SEQ ID NO:7, SEQ ID NO:8, SEQ ID NO:9, and SEQ ID NO: 10, and a complete complement thereof.

In one embodiment, the recombinant DNA molecule is from corn containing the corn event MON95275 in a sample of seed which seed has been deposited with the American Type Culture Collection repository (ATCC) and designated with the Accession No. PTA-126049.

Another aspect of the invention provides a DNA molecule comprising a polynucleotide segment of sufficient length to function as a DNA probe that hybridizes specifically under stringent hybridization conditions with corn event MON95275 DNA in a sample, wherein detecting hybridization of the probe to the corn event DNA under the stringent hybridization conditions is diagnostic for confirming the presence of corn event MON95275 DNA in that sample. In certain embodiments, the sample comprises a corn plant, corn plant cell, corn seed, corn plant part, corn pollen, progeny of any of the foregoing, processed corn seed, animal feed comprising corn, corn oil, corn meal, corn flour, corn flakes, corn bran, pasta and other food products made with corn, corn biomass, and fuel products produced using corn and corn parts, provided that such corn and corn products contain detectable amounts of corn event MON95275 DNA or detectable amounts of the novel toxin proteins or the double stranded DNA produced by corn plants, cells and the like that contain the corn event MON95275 DNA.

Yet another aspect of the invention provides a first DNA molecule and a second DNA molecule different from the first DNA molecule, i.e. a pair of DNA molecules that function as primers when used together in an amplification reaction containing the appropriate reagents necessary for conducting a DNA amplification procedure with a sample containing corn event MON95275 template DNA to produce an amplicon diagnostic for the presence of said corn event MON95275 DNA in said sample. The amplicon produced may contain at least the nucleotide sequence selected from the group consisting of SEQ ID NO: 1, SEQ ID NO:2, SEQ ID NO:3, SEQ ID NO: 4, SEQ ID NO:5, SEQ ID NO:6, SEQ ID NO:7, SEQ ID NO:8, SEQ ID NO:9, and SEQ ID NO: 10.

Another embodiment of the invention is a method of detecting the presence of a DNA segment diagnostic for confirming the presence or absence of corn event MON95275 DNA in a sample. In a certain embodiment, the method is conducted by contacting the sample with a probe DNA molecule that hybridizes specifically to DNA uniquely associated with corn event MON95275, then subjecting the sample and the probe DNA molecule to stringent hybridization conditions to allow the probe to bind to the appropriate complementary segment of corn event MON95275 specific DNA. Detecting hybridization of the probe DNA molecule to the DNA in the sample would be conclusive, meaning that detection of such hybridization, would be diagnostic, that the DNA in the sample contained a detectable amount of the corn event MON95275 DNA.

Yet another embodiment of the invention is a method of detecting the presence of a DNA segment diagnostic for corn event MON95275 DNA in a sample containing corn DNA. In one embodiment, the method comprises the steps of contacting a sample with a pair of DNA molecules that function as thermal amplification primers specific for amplification of a segment of the corn event MON95275 DNA, and performing an amplification reaction sufficient to produce the DNA amplicon, then detecting the presence of the DNA amplicon in the reaction. Detection of the DNA amplicon may be diagnostic for the presence of a detectable amount of the corn event MON95275 DNA in the sample, and the amplicon may contain the nucleotide sequence selected from the group consisting of SEQ ID NO: 1, SEQ ID NO:2, SEQ ID NO:3, SEQ ID NO:4, SEQ ID NO:5, SEQ ID NO: 6, SEQ ID NO:7, SEQ ID NO:8, SEQ ID NO:9, and SEQ ID NO: 10.

Another embodiment of the invention is a corn plant, corn plant part, corn cell, or part thereof comprising a recombinant polynucleotide molecule comprising the nucleotide sequence selected from the group consisting of SEQ ID NO: 1, SEQ ID NO:2, SEQ ID NO:3, SEQ ID NO:4, SEQ ID NO:5, SEQ ID NO:6, SEQ ID NO:7, SEQ ID NO:8, SEQ ID NO:9, and SEQ ID NO: 10. This corn plant, corn plant part, corn cell, or part thereof is insecticidal when provided in the diet of a Colcopteran insect pest. Coleopteran insect target pests intended to be controlled include, but are not limited to, Western Corn Rootworm (*Diabrotica virgifera virgifera*) and Northern Corn Rootworm (*Diabrotica barberi*). In addition, the corn plant can be further defined as progeny of any generation of a corn plant comprising the corn event MON95275, provided that the progeny contains the corn event MON95275 DNA.

Yet another embodiment of the invention is a method for protecting a corn plant from insect infestation, wherein said method comprises providing in the diet of a Coleopteran insect pest an insecticidally effective amount of cells or tissue of the corn plant comprising corn event MON95275. Contemplated Coleopteran insect pests include Western Corn Rootworm (*Diabrotica virgifera virgifera*) and Northern Corn Rootworm (*Diabrotica barberi*).

Another embodiment of the invention is a method of producing an insect resistant corn plant comprising: a) breeding two different corn plants to produce progeny, wherein at least one of the two different corn plants contains the corn event MON95275 DNA; b) confirming in the progeny the presence of a DNA segment diagnostic for corn event MON95275 DNA; and c) selecting the progeny comprising corn event MON95275 DNA. In certain embodiments, these progeny are corn rootworm resistant corn plants.

A further embodiment of the invention is a corn seed, nonliving plant material, or a microorganism comprising a detectable amount of the nucleotide sequence selected from the group consisting of SEQ ID NO: 1, SEQ ID NO:2, SEQ ID NO:3, SEQ ID NO:4, SEQ ID NO:5, SEQ ID NO: 6, SEQ ID NO: 7, SEQ ID NO:8, SEQ ID NO:9, and SEQ ID NO: 10, or complete complements thereof.

Yet another embodiment is a commodity corn product comprising a detectable amount of a DNA molecule unique to the DNA descriptive of the corn event MON95275, wherein the molecule comprises a nucleotide sequence selected from the group consisting of SEQ ID NO:1, SEQ ID NO:2, SEQ ID NO:3, SEQ ID NO:4, SEQ ID NO:5, SEQ ID NO:6, SEQ ID NO:7, SEQ ID NO: 8, SEQ ID NO:9, and SEQ ID NO:10. Contemplated commodity corn products include, but are not limited to, whole or processed corn seed, animal feed comprising corn, corn oil, corn meal, corn flour, corn flakes, corn bran, corn biomass, and fuel products produced using corn and corn parts.

Another embodiment of the invention is a corn plant, corn plant part, or corn seed thereof comprising DNA functional as a template when tested in DNA amplification method producing an amplicon diagnostic for the presence of corn event MON95275 DNA.

Yet another embodiment of the invention is a method of determining the zygosity of the genome of a corn plant or corn seed comprising DNA descriptive of the corn event MON95275. The zygosity is determined in a series of consecutive steps. In the first step, a sample comprising corn DNA is contacted with a first primer pair that is capable of producing an amplicon diagnostic for DNA that is descriptive of and present exclusively in corn event MON95275. Then the sample comprising corn DNA is contacted with a second primer pair that is designed to produce an amplicon of an internal standard known to be single-copy and homozygous in the corn plant. The method additionally includes contacting the DNA sample with a probe set which contains at least a first probe that specifically hybridizes the allele of corn event MON95275, and a second probe that specifically hybridizes to the internal standard genomic DNA known to be single-copy and homozygous in the corn plant. The method also includes a DNA amplification reaction performed using real-time PCR and determining the cycle thresholds (Ct values) of the amplicon corresponding to the allele of corn event MON95275 and the single-copy, homozygous internal standard. After the amplification, the difference ($\Delta$Ct) between the Ct value of the single-copy, homozygous internal standard amplicon and the Ct value of the allele for corn event MON95275 amplicon may be calculated. In one embodiment, zygosity is determined wherein a $\Delta$Ct of about zero (0) indicates homozygosity of the inserted T-DNA of corn event MON95275 and a $\Delta$Ct of about one (1) indicates heterozygosity of the inserted T-DNA of corn event MON95275. In certain embodiments of this method, the primer pairs are selected from the group consisting of SEQ ID NO: 15 combined with SEQ ID NO: 16, and SEQ ID NO:18 combined with SEQ ID NO: 19; and wherein the probes are SEQ ID NO: 17 and SEQ ID NO:20. In yet another embodiment of this invention the ΔCt of about one (1) indicating heterozygosity of the inserted T-DNA of corn event MON95275 is in the range of 0.75 to 1.25. In certain embodiments, a ΔCt of about zero (0) may be about 0, 0.05, 0.1, 0.15, 0.2, or 0.25, in other embodiments, a ΔCt of about one (1) may be about 0.75, 0.8, 0.85, 0.9, 0.95, 1.0, 1.05, 1.1, 1.15, 1.2, or 1.25. In a further embodiment, a ΔCt of about one (1) may be in the range of 0.75 to 1.25, 0.8 to 1.25, 0.85 to 1.25, 0.9 to 1.25, 0.95 to 1.25, 1.0 to 1.25, 1.05 to 1.25, 1.1 to 1.25, 1.15 to 1.25, 1.2 to 1.25, 0.75 to 1.2, 0.8 to 1.2, 0.85 to 1.2, 0.9 to 1.2, 0.95 to 1.2, 1.0 to 1.2, 1.05 to 1.2, 1.1 to 1.2, 1.15 to 1.2, 0.75 to 1.15, 0.8 to 1.15, 0.85 to 1.15, 0.9 to 1.15, 0.95 to 1.15, 1.0 to 1.15, 1.05 to 1.15, 1.1 to 1.15, 0.75 to 1.1, 0.8 to 1.1, 0.85 to 1.1, 0.9 to 1.1, 0.95 to 1.1, 1.0 to 1.1, 1.05 to 1.1, 0.75 to 1.05, 0.8 to 1.05, 0.85 to 1.05, 0.9 to 1.05, 0.95 to 1.05, 1.0 to 1.05, 0.75 to 1.0, 0.8 to 1.0, 0.85 to 1.0, 0.9 to 1.0, 0.95 to 1.0, 0.75 to 0.95, 0.8 to 0.95, 0.85 to 0.95, 0.9 to 0.95, 0.75 to 0.9, 0.75 to 0.85, 0.75 to 0.8, 0.8 to 0.9, 0.8 to 0.85, or 0.85 to 0.9.

A further embodiment of the invention is a method of determining the zygosity of a corn plant or corn seed comprising corn event MON95275 comprising: a) contacting a sample comprising corn DNA with a set of primer pairs comprising at least two different primer pairs capable of producing a first amplicon diagnostic for corn event MON95275 and a second amplicon diagnostic for native corn genomic DNA not comprising corn event MON95275; i) performing a nucleic acid amplification reaction with the sample and the set of primer pairs; ii) detecting in the nucleic acid amplification reaction the first amplicon diagnostic for corn event MON95275, or the second amplicon diagnostic for native corn genomic DNA not comprising corn event MON95275, wherein the presence of only the first amplicon is diagnostic of a homozygous event MON95275 DNA in the sample, and the presence of both the first amplicon and the second amplicon is diagnostic of a corn plant heterozygous for corn event MON95275 allele; or b) contacting a sample comprising corn DNA with a probe set which contains at least a first probe that specifically hybridizes to corn event MON95275 DNA and at least a second probe that specifically hybridizes to corn genomic DNA that was disrupted by insertion of the heterologous DNA of corn event MON95275 and does not hybridize to corn event MON95275 DNA; i) hybridizing the probe set with the sample under stringent hybridization conditions, wherein detecting hybridization of only the first probe under the hybridization conditions is diagnostic for a homozygous allele of corn event MON95275 DNA in the sample, and wherein detecting hybridization of both the first probe and the second probe under the hybridization conditions is diagnostic for a heterozygous allele of corn event MON95275 in said sample. In one embodiment of this method, the set of primer pairs comprises SEQ ID NO:15 combined with SEQ ID NO:16 which can be used to produce an amplicon that can be detected using the probe sequence set forth in SEQ ID NO:17, and SEQ ID NO: 21 combined with SEQ ID NO:22 which can be used to produce an amplicon that can be detected using the probe sequence set forth in SEQ ID NO:23.

The forgoing and other aspects of the invention will become more apparent from the following detailed description.

BRIEF DESCRIPTION OF THE SEQUENCES

Figure 1:
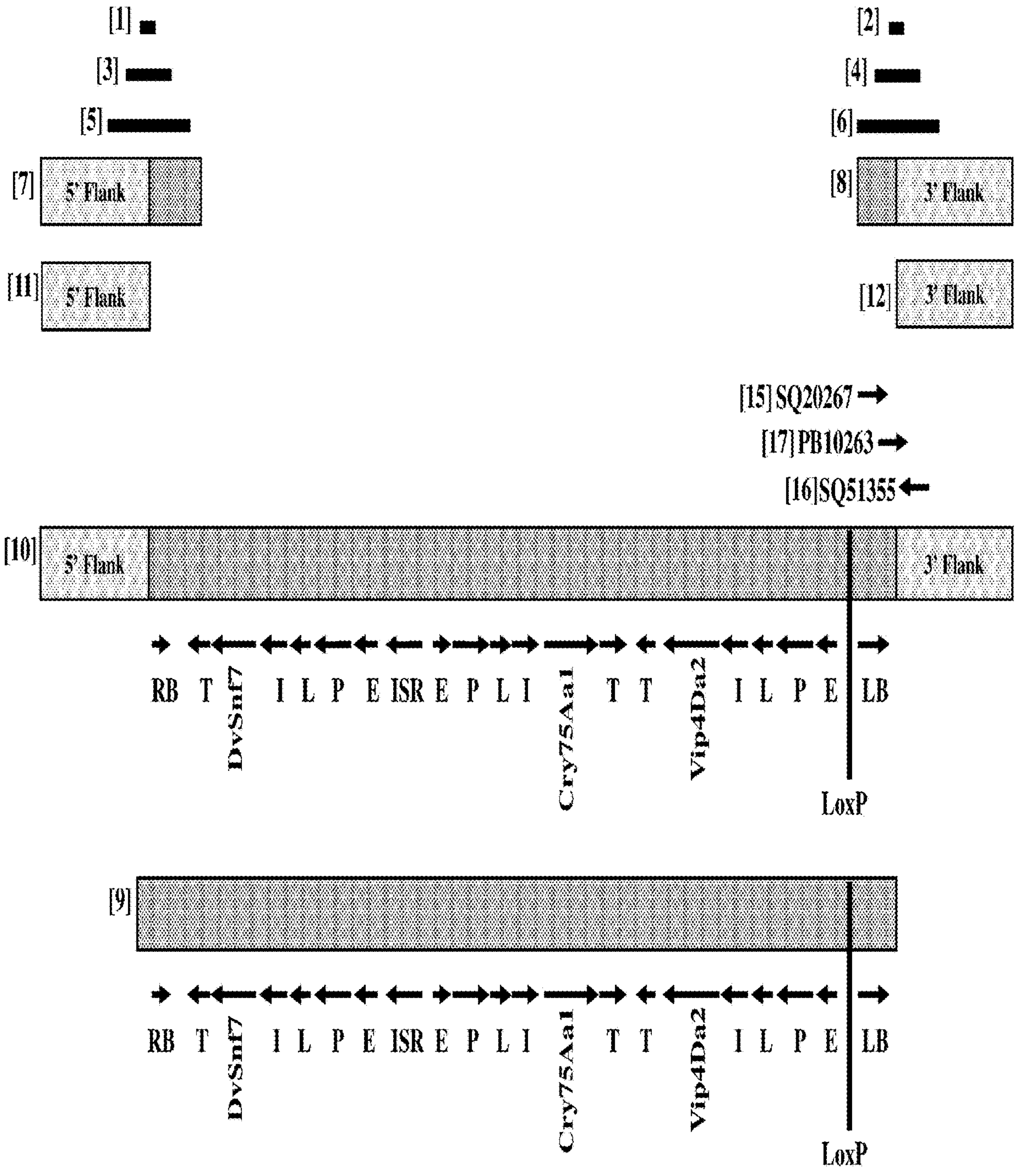
FIG. 1 is a graphical depiction of the orientation and alignment of the DNA elements/segments that are present within the nucleotide sequence shown in SEQ ID NO: 10, which is the sequence of the inserted transgenic DNA and the corresponding adjacent 5' and 3' sequences of the corn genome present within the corn event MON95275. [1] (SEQ ID NO:1) and [2] (SEQ ID NO: 2) each graphically represent the approximate positions of the sequences of the 50 consecutive nucleotide segments referred to respectively as a 5' or 3' junction sequence, respectively the arbitrarily assigned left, 5' end, and the right, 3' end junction sequences of [9] that consist respectively of 25 consecutive nucleotides of corn genome DNA (ends of lighter gray shaded segment of [10]) and 25 consecutive nucleotides of adjacent inserted transgenic DNA (darker gray shaded segment of [10]); [3] (SEQ ID NO:3) and [4] (SEQ ID NO:4) each graphically represent 100 consecutive nucleotide segments of DNA at the 5' and 3' junction positions, are respectively a 5' or 3' junction sequence, and each contain 50 consecutive nucleotides of corn genome DNA and 50 consecutive nucleotides of adjacent inserted transgenic DNA; [5] (SEQ ID NO: 5) and [6] (SEQ ID NO:6) each graphically represent 200 consecutive nucleotide segments of DNA at the junction positions, are respectively a 5' or 3' junction sequence, and each contain 100 consecutive nucleotides of corn genome DNA and 100 consecutive nucleotides of adjacent inserted transgenic DNA; [7] (SEQ ID NO:7) is representative of the 5' junction region of corn genomic DNA and the inserted transgenic DNA and contains 1,073 consecutive nucleotides of the corn genome DNA and 153 consecutive nucleotides of the adjacent inserted transgenic DNA; [8] (SEQ ID NO: 8) is representative of the 3' junction region of corn genomic DNA and the inserted transgenic DNA containing 101 consecutive nucleotides of the inserted transgenic DNA and 1,006 consecutive nucleotides of the adjacent corn genome DNA; [9] (SEQ ID NO:9) represents the length and structure of the inserted DNA, and the arrows and labels below each arrow represent the expression elements in the three cassettes within the inserted DNA in which RB/LB represent the positions of the right and left borders of the *Agrobacterium* double border mediated transformation vector, LoxP represents the position of the residual Cre-recombinase recognition site remaining in the inserted DNA after marker excision, the three letter E's represent the positions of enhancer elements in the respective constructs, the three letter P's represent the positions of the promoter elements in the respective constructs, the three letter L's represent the positions of leader sequences (5' untranslated regions, 5'UTR) in the respective constructs, the three letter I's represent the positions of the intron sequences in the respective constructs, the three letter T's represent the positions of the transcription termination sequences (3' untranslated regions, 3'UTR) in the respective constructs, and ISR represents the position of an intergenic sequence region (ISR4). The three constructs from right to left on the page of the drawing encode the coleopteran pest toxic Vip4Da2 and Cry75Aa1 toxins, and the segment encoding an RNA molecule capable of folding into a hairpin shaped double stranded molecule that is designed for suppression of transcripts from and thus reduction of the translated protein, Snf7, a protein that is essential for survival of corn rootworm larvac. [11] (SEQ ID NO:11) is representative of the position of the corn genome DNA flanking the 5' end of the inserted DNA, and [12] (SEQ ID NO:12) is representative of the position of the corn genome DNA flanking the 3' end of the inserted DNA. [15] (SEQ ID NO:15, primer SQ51355), and [16] (SEQ ID NO:16, primer SQ51355) are representative of the position of a primer pair that can be used in a thermal amplification reaction to produce an amplicon of 74 nucleotides containing the right insert/genome junction, the arrows showing the direction in which the amplification would proceed to form the amplicon from the respective positions within [10]. (SEQ ID NO:17, PB10263) is representative of a probe and the position to which the probe would bind (or hybridize to) the amplicon produced using primers [16] and [17], for detecting the presence of the MON95275 Event in a sample.

SEQ ID NO:1 is a 50 nucleotide sequence representing the 5' junction region of corn genomic DNA and the integrated transgenic expression cassette (25 nucleotides corn genome DNA at 5' end of SEQ ID NO:1, 25 nucleotides transgenic inserted DNA at 3' end of SEQ ID NO: 1), and can be identified within SEQ ID NO:10 at nucleotide positions 1,049-1,098.

SEQ ID NO:2 is a 50 nucleotide sequence representing the 3' junction region of the integrated transgenic expression cassette and the corn genomic DNA (25 nucleotides transgenic inserted DNA at 5' end of SEQ ID NO:2, 25 nucleotides corn genome DNA at 3' end of SEQ ID NO: 2), and can be identified within SEQ ID NO: 10 at nucleotide positions 15,731-15,780.

SEQ ID NO:3 is a 100 nucleotide sequence representing the 5' junction region of corn genomic DNA and the integrated transgenic expression cassette (50 nucleotides corn genome DNA at 5' end of SEQ ID NO:3, 50 nucleotides transgenic inserted DNA at 3' end of SEQ ID NO: 3), and can be identified within SEQ ID NO: 10 at nucleotide positions 1,024-1,123.

SEQ ID NO:4 is a 100 nucleotide sequence representing the 3' junction region of the integrated transgenic expression cassette and the corn genomic DNA (50 nucleotides transgenic inserted DNA at 5' end of SEQ ID NO:4, 50 nucleotides corn genome DNA at 3' end of SEQ ID NO: 4), and can be identified within SEQ ID NO:10 at nucleotide positions 15,706-15,805.

SEQ ID NO:5 is a 200 nucleotide sequence representing the 5' junction region of corn genomic DNA and the integrated transgenic expression cassette (100 nucleotides corn genome DNA at 5' end of SEQ ID NO:5, 100 nucleotides transgenic inserted DNA at 3' end of SEQ ID NO: 5), and can be identified within SEQ ID NO: 10 at nucleotide positions 974-1,173.

SEQ ID NO:6 is a 200 nucleotide sequence representing the 3' junction region of the integrated transgenic expression cassette and the corn genomic DNA (100 nucleotides transgenic inserted DNA at 5' end of SEQ ID NO:6, 100 nucleotides corn genome DNA at 3' end of SEQ ID NO: 6), and can be identified within SEQ ID NO: 10 at nucleotide positions 15,656-15,855.

SEQ ID NO:7 is a 1,226 nucleotide sequence representing the 5' junction region of corn genomic DNA and the integrated transgenic expression cassette (1,073 nucleotides corn genome DNA at 5' end of SEQ ID NO:5, 153 nucleotides transgenic inserted DNA at 3' end of SEQ ID NO: 5), and can be identified within SEQ ID NO: 10 at nucleotide positions 1-1,226.

SEQ ID NO:8 is a 1,207 nucleotide sequence representing the 3' junction region of the integrated transgenic expression cassette and the corn genomic DNA (101 nucleotides transgenic inserted DNA at 5' end of SEQ ID NO:8, 1,106 nucleotides corn genome DNA at 3' end of SEQ ID NO: 8), and can be identified within SEQ ID NO:10 at nucleotide positions 15,655-16,861.

SEQ ID NO:9 is a 14,682 nucleotide sequence corresponding to the transgenic inserted T-DNA of corn event MON95275, and can be identified within SEQ ID NO:10 at nucleotide positions 1,074-15,755.

SEQ ID NO: 10 is a 16,861 nucleotide sequence corresponding to the contiguous nucleotide sequence of the 5' genomic flanking DNA nucleotide sequence, the inserted T-DNA nucleotide sequence in event MON95275, and the 3' genomic flanking DNA nucleotide sequence; and includes SEQ ID NO:11 (nucleotides 1-1,073), SEQ ID NO:9 (nucleotides 1,074-15,755), and SEQ ID NO:12 (nucleotides 15,756-16,861).

SEQ ID NO:11 is a 1,073 nucleotide sequence representing the corn genomic DNA flanking the 5' end of the inserted T-DNA, and can be identified within SEQ ID NO:10 at nucleotide positions 1-1,073.

SEQ ID NO:12 is a 1,106 nucleotide sequence representing the corn genomic DNA flanking the 3' end of the inserted T-DNA, and can be identified within SEQ ID NO:10 at nucleotide positions 15,756-16,861.

SEQ ID NO:13 is a 19,612 nucleotide sequence representing the transgene cassette comprised within the binary plant transformation plasmid vector used to transform corn to produce corn event MON95275.

SEQ ID NO:14 is a 35 nucleotide LoxP sequence representing used for Cre-mediated excision and recombination, and the residual sequence can be identified within SEQ ID NO: 10 at nucleotide positions 15,444-15,478.

SEQ ID NO:15 is a 27 nucleotide sequence corresponding to a thermal amplification primer referred to as SQ20267 which can be used to identify corn event MON95275 DNA in a sample or which can be used to detect an insertion event that, when subjected to Cre-recombinase marker excision, results in event MON95275 DNA. SEQ ID NO:15 is identical to the nucleotide sequence corresponding to positions 15,706-15,732 of SEQ ID NO:10.

SEQ ID NO:16 is a 24 nucleotide sequence corresponding to a thermal amplification primer referred to as SQ51355 used to identify corn event MON95275 DNA in a sample or which can be used to detect an insertion event that, when subjected to Cre-recombinase marker excision, results in event MON95275 DNA. SEQ ID NO:16 is identical to the reverse compliment of the nucleotide sequence corresponding to positions 15,756-15,779 of SEQ ID NO:10.

SEQ ID NO:17 is a 19 nucleotide sequence corresponding to a probe referred to as PB10263 used to identify corn event MON95275 DNA in a sample or which can be used to detect an insertion event that, when subjected to Cre-recombinase marker excision, results in event MON95275 DNA. SEQ ID NO:17 is identical to the nucleotide sequence corresponding to positions 15,734-15,752 of SEQ ID NO:10, and as a probe can bind to a polynucleotide segment having the reverse complement of the nucleotides at this position.

SEQ ID NO:18 is a 24 nucleotide sequence corresponding to a thermal amplification primer referred to as SQ20222 used as an internal control for the event and zygosity assay for corn event MON95275 and hybridizes to a region of the corn genome.

SEQ ID NO:19 is a 28 nucleotide sequence corresponding to a thermal amplification primer referred to as SQ20221 used as an internal control for the event and zygosity assay for corn event MON95275 and hybridizes to a region of the corn genome.

SEQ ID NO:20 is a 17 nucleotide sequence corresponding to a probe referred to as PB50298 used as an internal control for the event and zygosity assay for corn event MON95275 and hybridizes to a region of the corn genome.

SEQ ID NO:21 is a 20 nucleotide sequence corresponding to a thermal amplification primer referred to as PNEG95275_F used in the zygosity assay for corn event MON95275 and hybridizes to a region of corn genomic DNA which was deleted when the T-DNA used to produce event MON95275 inserted into the corn genome. An amplicon produced in a thermal amplification reaction using the combination of primers PNEG95275_F and PNEG95275_R (SEQ ID NO: 22) and native corn DNA as template is diagnostic for the wild-type allele lacking the MON95275 inserted T-DNA.

SEQ ID NO:22 is a 20 nucleotide sequence corresponding to a thermal amplification primer referred to as PNEG95275_R used in the zygosity assay for corn event MON95275 and hybridizes to a region of corn genomic DNA which was deleted when the T-DNA used to produce event MON95275 inserted into the corn genome. An amplicon produced in a thermal amplification reaction using the combination of primers PNEG95275_F (SEQ ID NO:21) and PNEG95275_R and native corn DNA as template is diagnostic for the wild-type allele lacking the MON95275 inserted T-DNA.

SEQ ID NO:23 is a 17 nucleotide sequence corresponding to a probe referred to as PRBNEG95275 used in the zygosity assay for confirming the absence of corn event MON95275 and hybridizes to a region of native corn genomic DNA which was deleted when the T-DNA used to produce event MON95275 inserted into the corn genome.

SEQ ID NO:24 is a DNA sequence that functions in plants as an expression enhancer segment.

SEQ ID NO:25 is a plant functional promoter operably linked to an untranslated leader sequence.

SEQ ID NO:26 is a DNA sequence that functions in plants as an expression enhancer segment.

DETAILED DESCRIPTION

The present invention provides a transgenic corn event—MON95275—that achieves insecticidal control over Coleopteran pests of corn by expression of Cry75Aa1, Vip4Da2, and a dsRNA targeting for suppression the native and essential corn rootworm DvSnf7. Specifically, corn event MON95275 provides resistance to the Coleopteran insect pests Western Corn Rootworm (*Diabrotica virgifera virgifera*, WCR) and Northern Corn Rootworm (*Diabrotica barberi*, NCR). Corn event MON95275 will meet a great need for control of these insects in corn agricultural production where corn rootworms are present, because chemical insecticides often do not provide adequate control of these insects, or because multiple applications of such chemistries are required to be applied throughout the growing season, increasing the labor requirements, carbon footprint, and input of chemical pesticides in the environment as well as adding significantly to the cost of corn production. Reference to corn event MON95275 herein is intended as being equivalent to a reference to MON 95275, event MON95275, event MON 95275, MON95275 event, MON 95275 event; the references are interchangeable.

The resistance to infestation by Coleopteran species provided by event MON95275 arises in connection with the expression of a DNA segment encoding two insecticidal proteins and a double-stranded RNA (dsRNA) capable of interfering with a corn root worm essential gene, that are operably and covalently linked within the inserted transgenic DNA that in part defines the corn event MON95275. The two insecticidal proteins in the MON95275 event are a Cry75Aa1 protein (United States Patent Application Publication No. 2016-0319302A2, SEQ ID NO:25, coding sequence, SEQ ID NO:37) and a Vip4Da2 protein (U.S. Pat. No. 10,100,330, SEQ ID NO: 2, coding sequence, SEQ ID NO:3). The dsRNA produced in the event MON95275 targets for suppression a gene referred to as DvSnf7, in Western Corn Rootworm (*Diabrotica virgifera virgifera*) when ingested by a rootworm (see, for example, U.S. Pat. No. 7,943,818, SEQ ID NO:818). These two insecticidal proteins and dsRNA are expressed from the three expression cassettes within the inserted transgenic DNA construct as set forth in SEQ ID NO:9 and illustrated in FIG. 1.

The Cry75Aa1 protein in corn event MON95275 is expressed by a *Tripsacum dactyloides* RCc3 promoter (U.S. Pat. No. 9,617,553, SEQ ID NO:13) and leader, operably linked to an enhancer derived from a Dalia mosaic virus promoter, Genbank accession EF513491, nucleotides 1 through 322; and a *Setaria italica* 14-3-3C protein gene intron (United States Patent Application Publication No. 2013-0031672 A2, SEQ ID NO:151).

The Vip4Da2 protein in corn event MON95275 is expressed by a *Zea mays* Lipid Transfer Protein promoter and leader, enhanced with rearranged enhancer derived from multiple public Dahlia mosaic virus promoters and a *Setaria italica* Actin 4 gene intron (United States Patent Application No. 2013-0031672 A2, SEQ ID NO:627). The Dahlia mosaic virus (DaMV) enhancer operably linked to the *Zea mays* Lipid Transfer Protein promoter and leader is a re-arranged composite of fragments derived from several public DaMV Genbank accessions, and is presented as SEQ ID NO:24. A first fragment is derived from the promoter of the DaMV-Holland (DaMV-H) strain, Genbank accession EU090957, nucleotides 1177-1494. This fragment is operably linked to a second fragment derived from the DaMV-H promoter, nucleotides 1003-1176. Within the first fragment, relative to SEQ ID NO:24, nucleotides 287 through 288, and nucleotides 319 through 322 were changed to sequences in analogous locations of a DaMV promoter within Genbank accession JX272320. In the native DaMV promoter configuration, the second fragment would precede the first fragment. The re-arrangement of these two fragments resulted in higher expression relative to the native fragment and was therefore selected for use in event MON95275.

The sequence encoding DvSnf7 specific dsRNA in corn event MON95275 is driven by a promoter and leader derived from Cauliflower mosaic virus (CaMV) isolate NY8153 (presented as SEQ ID NO:25), which is enhanced by an enhancer derived from the promoter of the pIIG gene encoding the physical impedance induced protein from *Zea mays*; and a *Zea mays* hsp70 intron. The CaMV promoter/leader is derived from Genbank accession M90541, nucleotides 6,907 through 7,482. Relative to SEQ ID NO:25, the second nucleotide was changed from a threonine (T) to an adenine (A) to remove a potential start codon in the operably linked cassette configuration. This CaMV promoter/leader comprised a longer leader sequence relative to the CaMV promoter and leader in corn event MON87411. This longer leader increased the expression levels of the DvSNF7 dsRNA in MON95275 relative to MON87411.

The expression of the Cry75Aa1 and Vip4Da2 transgene cassettes in MON95275 are oriented in a convergent manner as demonstrated in FIG. 1. The DvSnf7 transgene cassette in MON95275 is oriented in the divergent direction relative to the Cry75Aa1 transgene cassette, as demonstrated in FIG. 1. The DvSnf7 and the Cry75Aa1 transgene cassettes are separated from each other by an Intergenic Sequence Region (ISR4, U.S. Provisional Application Ser. No. 62/875,752). FIG. 1 shows the relative positions of each element-enhancer (E), promoter (P), 5' UTR or leader (L), intron (I), 3' UTR (T), ISR4 (ISR), DvSnf7, Cry75Aa1, and Vip4Da2-comprised within SEQ ID NO:9 and SEQ ID NO: 10.

Figure 2:
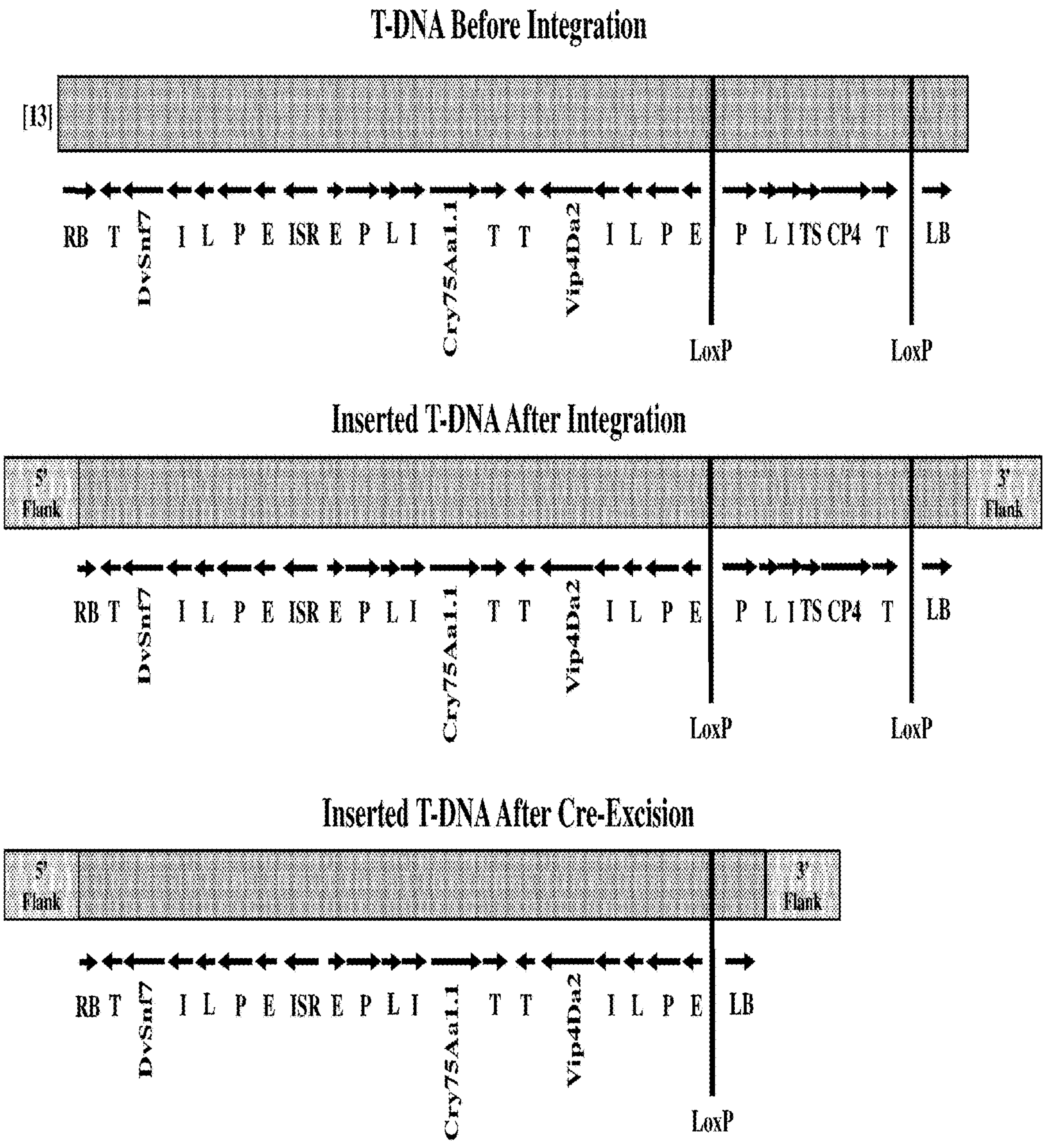
FIG. 2 illustrates the T-DNA cassette in the plasmid vector used to transform corn. One insertion event, when subjected to Cre-recombinase marker excision, resulted in event MON95275. [13] (SEQ ID NO:13) illustrates the DNA in the plasmid vector before integration (the “T-DNA Before Integration”). The arrows below [13] represent the individual genetic elements comprised within the three transgene cassettes designed to express the result effective coleopteran toxic agents. The CP4 EPSPS selectable marker cassette is flanked between the two LoxP segments which are recognized by the Cre-recombinase and which is capable of excising the selectable marker from the insertion event containing [13]. The insertion event DNA is represented by [14], differing from only by the fact that the segment [13] has been inserted into the corn genome, and is now depicted as being flanked 5' and 3' by the corn genome segments labeled as 5' Flank and 3' Flank. [18] represents the segment shown in FIG. 1 as [10].

As described herein, numerous constructs which varied in the use of expression elements, toxin coding sequences and orientation were evaluated. The construct used to create corn event MON95275 shown in FIG. 2 and presented as SEQ ID NO:13, provided superior performance relative to other constructs when evaluated for resistance to Coleopteran insect pest infestation. In addition, corn event MON95275 is free of the markers used for selection of the transformed plant cell as a result of excision using Cre-recombinase. The CP4 selection cassette is shown in FIG. 2 and comprised within SEQ ID NO:13. The CP4 selection cassette is flanked by two LoxP sites. Excision using Cre-recombinase resulted in the loss of the CP4 selection cassette after breeding with a Cre expressing transgenic corn event. The resulting progeny were evaluated for the absence of the selection cassette as well as the absence of the Cre-recombinase expression cassette, and those progeny lacking both were selected for further evaluation, resulting in selection of the marker-free corn event MON95275.

The event MON95275 was selected based on comparisons to thousands of different independent transgenic events, each transformed with a construct comprising the transgene cassette presented as SEQ ID NO:13, or other constructs comprising the same or different toxins. The events generated expressing the insect toxins were compared to non-transgenic corn control plants of the same variety. The results as illustrated in the Examples show that the event MON95275 displayed superior properties due to expression of the Cry75Aa1 and Vip4Da2 protein, and the DvSnf7 specific dsRNA. The plurality of transgenic events produced using the construct used for generating the event MON95275 were each more likely than other events produced with other constructs to exhibit efficacious control of Coleopteran insect pests.

MON95275 was created through plant transformation techniques used to insert heterologous DNA (also known as transgenic DNA) randomly into a chromosome of the genome of a corn cell to produce a genetically engineered corn cell, also referred to as a "transgenic" or "recombinant" corn cell. Using this technique, many individual cells are transformed, each resulting in a unique "transgenic event" or "event" due to the random insertion of the foreign DNA into the genome. A transgenic plant is then regenerated from each individual transgenic cell. This results in every cell of the transgenic plant containing the uniquely inserted transgenic event as a stable part of its genome. This transgenic plant can then be used to produce seed which are then planted and grown into progeny plants, each containing the unique transgenic event.

Corn event MON95275 was produced by an *Agrobacterium*-mediated transformation process of corn immature embryos with a single T-DNA binary system. In this system, an *Agrobacterium* strain employing one binary plasmid vector with a single T-DNA was utilized. The T-DNA construct comprised three transgene cassettes for the expression of the insect toxin coding sequences encoding Cry75Aa, Vip4Da2 and the dsRNA encoding sequence encoding DvSnf7, and a transgene cassette used for the selection of transformed corn cells using glyphosate selection (CP4). The T-DNA construct is SEQ ID NO: 13 and illustrated in FIG. 2 ("T-DNA Before Integration"). During integration, a single nucleotide was changed from a guanine (G) to a threonine (T) at nucleotide (nt) position 5,300 of SEQ ID NO:13 (nt 4,986 of SEQ ID NO:9 and nt 6,059 of SEQ ID NO:10) in a region that is not within any of the coding sequences or expression elements. Also, during integration, six (6) nucleotides were inserted between the inserted T-DNA and 3' genomic flanking DNA and seven hundred forty-six (746) nucleotides were deleted from the wild-type genomic DNA. The glyphosate selection cassette was flanked on both sides with LoxP recognition sites which are recognized by Cre-recombinase, derived from Enterobacteria phage P1 (Larry Gilbertson (2003) *Cre-lox recombination: Cre-active tools for plant biotechnology. TRENDS in Biotechnology,* 21:12, 550-555).

As specifically described herein, corn event MON95275 was produced by a complex research and development process in which: (1) over one hundred sixty (160) plasmid vector constructs—which varied with respect to the coding sequences for the insecticidal proteins, the coding sequences for the transcriptional regulatory elements, and number and orientation of the cassettes within the constructs—were developed and transformed into corn cells to create thousands of events that were tested and analyzed, resulting in the selection of the construct used to generate event MON95275; (2) thousands of corn cells were transformed with the construct used to generate event MON95275, creating a population of transgenic plants in which each plant contained a unique transgenic event that was regenerated and tested; (3) the final event MON95275 was selected after a rigorous multi-year event selection process involving the testing and analysis of molecular characteristics, efficacy, protein expression, and agronomic properties in a variety of genetic backgrounds; and (4) the glyphosate selection cassette in corn event MON95275 was removed through in vivo Cre-excision to create a "marker-free" final event MON95275. Corn event MON95275 was thus produced and selected as a uniquely superior event useful for broad-scale agronomic purposes.

The plasmid DNA inserted into the genome of corn event MON95275 was characterized by detailed molecular analysis. This analysis included: the insert number (number of integration sites within the corn genome), the genomic insert location (the specific site in the corn genome where the insertion occurred), the copy number (the number of copies of the T-DNA within one locus), and the integrity of the transgenic inserted DNA. The detailed molecular analysis demonstrated that the integrated T-DNA containing the Cry75Aa1, Vip4Da2, and DvSnf7 expression cassettes remained intact after integration and Cre-excision of the glyphosate (CP4) selection cassette. As used herein, an "expression cassette" or "cassette" is a recombinant DNA molecule comprising a combination of distinct elements that are to be expressed by a transformed cell. Table 1 provides a list of the elements contained in SEQ ID NO:10, the DNA sequence that corresponds to corn event MON95275.

TABLE 1

Description of corn event MON95275

| Element | Position in SEQ ID NO: 10 | Description |
|---|---|---|
| 5' Flanking DNA | 1-1073 | DNA sequence flanking the 5' end of the transgenic insert. |
| Right Border Region | 1074-1090 | DNA region from *Agrobacterium tumefaciens* containing the right border sequence. |
| T-Ps.RbcS2-E9-1:1:6 | 1196-1828 | 3' untranslated region from a ribulose bisphosphate carboxylase small subunit gene from *Pisum sativum*. |
| DvSnf7 | 1858-2478 | Partial coding sequences of the Snf7 gene designed to match that from *Diabrotica virgifera virgifera* encoding the SNF7 subunit of the ESCRT-III complex forming a dsRNA to suppress the Snf7 gene transcript. |
| I-Zm.DnaK:1 | 2524-3327 | Intron and flanking exon sequence of the hsp70 gene from *Zea mays* encoding the heat shock protein 70 (HSP70). |
| L-CaMV.35S-1:1:14 | 3334-3384 | 5' untranslated region derived from the 35S RNA of Cauliflower mosaic virus isolate NY8153. |
| P-CaMV.35S-1:1:67 | 3385-3909 | Promoter derived from the 35S RNA of Cauliflower mosaic virus isolate NY8153. |
| E-Zm.PIIG1:1:1 | 3910-4824 | Enhancer derived from the promoter of the pIIG gene encoding the physical impedance induced protein from *Zea mays*. |
| IG-Des.Isr4:1 | 4832-6050 | Intergenic Sequence Region |
| E-DaMV.FLT-1:1:2 | 6072-6393 | Enhancer sequence derived from a Dalia mosaic virus promoter, Genbank accession EF513491, nucleotides 1 through 322. |
| P-Td.RCc3_1:1 | 6407-7146 | Promoter derived from an RCc3 gene from *Tripsacum dactyloides*. |
| L-Td.RCc3_1:1 | 7147-7237 | 5' untranslated region derived from an RCc3 gene from *Tripsacum dactyloides*. |
| I-SETit.14-3-3C-5-1:1:2 | 7238-7342 | Intron derived from a 14-3-3C protein gene from *Setaria italica*. |
| Cry75Aa1 | 7364-8521 | Coding sequence of a Cry75Aa1 insect toxin. |
| T-Cl.Hsp16.9_2:1 | 8269-8829 | 3' untranslated region derived from a heat shock protein 16.9 gene from *Coix lacryma-jobi*. |
| T-SETit.Ams1:1 | 8856-9290 | 3' untranslated region derived from an S-adenosylmethionine synthetase 1 gene from *Setaria italica*. |
| Vip4Da2 | 9298-12111 | Coding sequence of a Vip4Da2 insect toxin. |
| I-SETit.Act4-1:1:2 | 12138-13502 | Intron derived from an Actin 4 gene from *Setaria italica*. |
| L-Zm.Ltp-1:1:3 | 13511-13603 | 5' untranslated region derived from a Lipid transfer protein gene from *Zea mays*. |
| P-Zm.Ltp-1:1:2 | 13604-14804 | Promoter derived from a Lipid transfer protein gene from *Zea mays*. |
| E-DaMV.H-Flt:1 | 14805-15300 | Enhancer sequence derived from multiple ORF6 promoters of Dahlia mosaic virus isolates. |
| Lox-P | 15444-15478 | A recognition sequence for a site-specific recombinase from *Enterobacteria* phage P1. |
| Left Border Region | 15514-15755 | DNA region from *Agrobacterium tumefaciens* containing the left border sequence. |

TABLE 1-continued

| Description of corn event MON95275 | | |
|---|---|---|
| Element | Position in SEQ ID NO: 10 | Description |
| 3' Flanking DNA | 15756-16861 | DNA sequence flanking the 3' end of the transgenic insert. |

Corn event MON95275 is characterized as an insertion into a single locus in the corn genome, resulting in two new loci or junction sequences (e.g., sequences set forth in SEQ ID NO:1, SEQ ID NO:2, SEQ IDNO: 3, SEQ ID NO:4, SEQ ID NO:5, SEQ ID NO:6, SEQ ID NO:7, and SEQ ID NO:8) between the inserted DNA and the corn genome DNA that are not known to appear naturally in the corn genome or other transgenic corn events-they are unique to event MON95275. These junction sequences are useful in detecting the presence of the event MON95275 in corn cells, corn tissue, corn seed, and corn plants or corn plant products, such as corn commodity products. DNA molecular probes and primer pairs are described herein that have been developed for use in identifying the presence of these various junction segments in biological samples containing or suspected of containing corn cells, corn seed, corn plant parts, or corn plant tissue that contain the event MON95275.

A sample is intended to refer to a composition that is either substantially pure corn DNA or a composition that contains corn DNA. In either case, the sample is a biological sample, i.e., it contains biological materials, including but not limited to DNA obtained or derived from, either directly or indirectly, from the genome of corn event MON95275. “Directly” refers to the ability of the skilled artisan to directly obtain DNA from the corn genome by fracturing corn cells (or by obtaining samples of corn that contain fractured corn cells) and exposing the genomic DNA for the purposes of detection. “Indirectly” refers to the ability of the skilled artisan to obtain the target or specific reference DNA, i.e., a novel and unique junction segment described herein as being diagnostic for the presence of the event MON95275 in a particular sample, by means other than by direct via fracturing of corn cells or obtaining a sample of corn that contains fractured corn cells. Such indirect means include, but are not limited to, amplification of a DNA segment that contains the DNA sequence targeted by a particular probe designed to bind with specificity to the target sequence, or amplification of a DNA segment that can be measured and characterized, i.e., measured by separation from other segments of DNA through some efficient matrix such as an agarose or acrylamide gel or the like, or characterized by direct sequence analysis of the amplicons, or cloning of the amplicon into a vector and direct sequencing of the inserted amplicon present within such vector.

Detailed molecular analysis also demonstrated that event MON95275 contains a single T-DNA insertion with one copy of each of the Cry75Aa1, Vip4Da2, and DvSnf7 specific dsRNA expression cassettes. No additional elements from the transformation construct other than portions of the *Agrobacterium tumefaciens* left and right border regions used for transgenic DNA transfer from the plant transformation plasmid to the corn genome were identified in event MON95275. Further, thermal amplification producing specific amplicons diagnostic for the presence of event MON95275 in a sample and DNA sequence analyses were performed to determine the arbitrarily assigned 5' and 3' insert-to-plant genome junctions, confirm the organization of the elements within the insert, and determine the complete DNA sequence of the inserted transgenic DNA (SEQ ID NO: 9). SEQ ID NO: 11 is a sequence representing the one thousand seventy-three (1,073) base-pair (bp) 5' LH244 corn genomic DNA sequence flanking the inserted T-DNA sequence presented as SEQ ID NO:9. SEQ ID NO: 12 is a sequence representing the one thousand one hundred six (1,106) bp 3' LH244 corn genomic DNA sequence flanking the inserted T-DNA sequence presented as SEQ ID NO:9. SEQ ID NO:7 is a sequence representing the one thousand two hundred twenty-six (1,226) base-pair (bp) 5' LH244 corn genomic DNA sequence flanking the inserted T-DNA sequence combined with one hundred fifty-three (153) bp of inserted T-DNA sequence presented as SEQ ID NO:9. SEQ ID NO:8 is a sequence representing one hundred one (101) bp of inserted T-DNA sequence with the one thousand one hundred six (1,106) bp 3' LH244 corn genomic DNA sequence flanking the inserted T-DNA sequence presented as SEQ ID NO:9. SEQ ID NO: 10 corresponds to corn event MON95275 and contains a contiguous sequence (contig) comprising the 5' LH244 flanking sequence, the transgene insert of MON95275, and the 3' LH244 flanking sequence, and thus contains the insert-to-plant genome junction sequences.

Unless otherwise noted herein, terms are to be understood according to conventional usage by those of ordinary skill in the relevant art. Definitions of common terms in molecular biology may be found in Rieger et al., Glossary of Genetics: Classical and Molecular, 5$^{th}$ edition, Springer-Verlag: New York, 1991; and Lewin, Genes V, Oxford University Press: New York, 1994, along with other sources known to those of ordinary skill in the art. As used herein, the term “corn” means species belong to the genus *Zea*, preferably *Zea mays* and includes all plant varieties that can be bred with corn plants containing event MON95275, including wild corn species as well as those plants belonging to the genus *Zea* that permit breeding between species.

Transgenic plants which have been transformed with a DNA construct that contains expression cassettes expressing toxic amounts of the insecticidal proteins Cry75Aa1 and Vip4Da2, and toxic amounts of the insecticidal dsRNA specific for suppression of DvSnf7 are provided. What is meant by toxic amount is an efficacious amount, an insecticidal amount, an insecticidally-effective amount, a target insect suppressive amount, an efficacious pesticidal amount, an amount in the diet of insects in the order of Coleoptera that is insecticidal, and other similar terms to be understood according to conventional usage by those of ordinary skill in the relevant art. Corn plants transformed according to the methods and with the DNA construct disclosed herein are resistant to Colcopteran insect pests.

A transgenic “plant” is produced by transformation of a plant cell with heterologous DNA, i.e., a polynucleic acid construct that includes a number of efficacious features of interest, regeneration of a plant resulting from the insertion of the transgene into the genome of the plant cell, and selection of a particular plant characterized by insertion into a particular genome location and the number of efficacious features of the regenerated transgenic plant. The term "event" refers to DNA from the original transformant comprising the inserted DNA and flanking genomic sequences immediately adjacent to the inserted DNA. Such DNA is unique and would be expected to be transferred to a progeny that receives the inserted DNA, including the transgene of interest, as the result of a sexual cross of parental line that includes the inserted DNA (e.g., the original transformant and progeny resulting from selfing) and a second parental line, for instance, a parental line that does not contain the inserted DNA. The present invention also provides the original transformant plant and progeny of the transformant that include the heterologous DNA. Such progeny may be produced by a sexual outcross between plants comprising the event and another plant wherein the progeny includes the heterologous DNA. Even after repeated back-crossing to a recurrent parent, the event is present in the progeny of the cross at the same chromosomal location.

As used herein, the term "recombinant" refers to a non-natural DNA, protein, or organism that would not normally be found in nature and was created by human intervention. A "recombinant DNA molecule" is a DNA molecule comprising a combination of DNA molecules that would not naturally occur together and is the result of human intervention. For example, a DNA molecule that is comprised of a combination of at least two DNA molecules heterologous to each other, such as a DNA molecule that comprises a transgene and the plant genomic DNA adjacent to the transgene, is a recombinant DNA molecule.

The terms "DNA" and "DNA molecule" referred to herein refer to a deoxyribonucleic acid (DNA) molecule. A DNA molecule may be of genomic or synthetic origin, and is by convention from the 5' (upstream) end to the 3' (downstream) end. As used herein, the term "DNA sequence" refers to the nucleotide sequence of the DNA molecule. By convention, the DNA sequences of the invention and fragments thereof are disclosed with reference to only one strand of the two-strand complementary DNA sequence strands. By implication and intent, the complementary sequences of the sequences provided here (the sequences of the complementary strand), also referred to in the art as the reverse complementary sequences, are within the scope of the invention and are expressly intended to be within the scope of the subject matter claimed.

As used herein, the term "fragment" refers to a smaller piece of the whole. For example, fragments of SEQ ID NO:10 would include sequences that are at least about 12 consecutive nucleotides, at least about 13 consecutive nucleotides, at least about 14 consecutive nucleotides, at least about 15 consecutive nucleotides, at least about 16 consecutive nucleotides, at least about 17 consecutive nucleotides, at least about 18 consecutive nucleotides, at least about 19 consecutive nucleotides, at least about 20 consecutive nucleotides, at least about 25 consecutive nucleotides, at least about 30 consecutive nucleotides, at least about 35 consecutive nucleotides, at least about 40 consecutive nucleotides, at least about 45 consecutive nucleotides, at least about 50 consecutive nucleotides, at least about 60 consecutive nucleotides, at least about 70 consecutive nucleotides, at least about 80 consecutive nucleotides, at least about 90 consecutive nucleotides, or at least about 100 consecutive nucleotides of the complete sequence of SEQ ID NO:10.

Reference in this application to an "isolated DNA molecule" or an equivalent term or phrase is intended to mean that the DNA molecule is one that is present alone or in combination with other compositions, but not within its natural environment. For example, nucleic acid elements such as a coding sequence, intron sequence, untranslated leader sequence, promoter sequence, transcriptional termination sequence, and the like, that are naturally found within the DNA of the genome of an organism are not considered to be "isolated" so long as the element is within the genome of the organism and at the location within the genome in which it is naturally found. However, each of these elements, and subparts of these elements, would be "isolated" within the scope of this disclosure so long as the element is not within the genome of the organism and at the location within the genome in which it is naturally found. Similarly, a nucleotide sequence encoding an insecticidal protein or any naturally occurring insecticidal variant of that protein would be an isolated nucleotide sequence so long as the nucleotide sequence was not within the DNA of the bacterium from which the sequence encoding the protein is naturally found. A synthetic nucleotide sequence encoding the amino acid sequence of the naturally occurring insecticidal protein would be considered to be isolated for the purposes of this disclosure. For the purposes of this disclosure, any transgenic nucleotide sequence, i.e., the nucleotide sequence of the DNA inserted into the genome of the cells of a plant or bacterium, or present in an extrachromosomal vector, would be considered to be an isolated nucleotide sequence whether it is present within the plasmid vector or similar structure used to transform cells, within the genome of the plant or bacterium, or present in detectable amounts in tissues, progeny, biological samples or commodity products derived from the plant or bacterium. In any circumstance, the isolated DNA molecule is a chemical molecule, regardless of whether it is referred to as a nucleic acid, a nucleic acid sequence, a polynucleotide sequence, a construct, a cassette, and the like. It is a novel, inventive molecule that exhibits industrial applicability both when present in a plant cell or in a plant genome, and when present outside of a plant cell, and therefore, exhibits and is intended to exhibit such utility regardless of where the molecule is located.

The DNA sequence of the region spanning the connection by phosphodiester bond linkage of one end of the transgenic insert to the flanking corn genomic DNA is referred to as a "junction." A junction is the connection point of the transgenic insert and flanking DNA as one contiguous molecule. One junction is found at the 5' end of the transgenic insert and the other is found at the 3' end of the transgenic insert, referred to herein as the 5' and 3' junction, respectively. A "junction sequence" refers to a DNA sequence of any length that spans the 5' or 3' junction of an event. Junction sequences of corn event MON95275 are apparent to one of skill in the art using SEQ ID NO: 10. Examples of junction sequences of MON95275 are provided as SEQ ID NOs: 1-8. FIG. 1 illustrates the physical arrangement of the junction sequences, arranged from 5' to 3', relative to SEQ ID NO:10. The junction sequences of MON95275 may be present as part of the genome of a plant, seed, or cell containing MON95275. The identification of any one or more of the junction sequences in a sample containing DNA from a corn plant, corn plant part, corn seed, or corn cell indicates that the DNA was obtained from corn containing event MON95275 and is diagnostic for the presence of corn event MON95275.

The junction sequences for MON95275 may be represented by a sequence from the group consisting of SEQ ID NO:1, SEQ ID NO:2, SEQ ID NO:3, SEQ ID NO:4, SEQ ID NO:5, SEQ ID NO: 6, SEQ ID NO:7, SEQ ID NO:8, and SEQ ID NO:10. For example, the junction sequences may be arbitrarily represented by the nucleotide sequences provided as SEQ ID NO: 1 (5' junction sequence) and SEQ ID NO:2 (3' junction sequence). Alternatively, the junction sequences may be arbitrarily represented by the nucleotide sequences provided as SEQ ID NO:3 (5' junction sequence) and SEQ ID NO:4 (3' junction sequence). Alternatively, the junction sequences may be arbitrarily represented by the nucleotide sequences provided as SEQ ID NO:5 (5' junction sequence) and SEQ ID NO:6 (3' junction sequence). Alternatively, the junction sequences may be arbitrarily represented by the nucleotide sequences provided as SEQ ID NO:7 (5' junction sequence) and SEQ ID NO:8 (3' junction sequence). These nucleotide sequences are connected by phosphodiester linkage, and in corn event MON95275 are present as part of the recombinant plant cell genome.

These junction sequences are diagnostic for the presence of event MON95275, or the construct comprised therein. Thus, the identification of one or more of SEQ ID NO: 1, SEQ ID NO: 2, SEQ ID NO:3, SEQ ID NO:4, SEQ ID NO:5, SEQ ID NO:6, SEQ ID NO:7, SEQ ID NO:8, and SEQ ID NO: 10 in a sample derived from a corn plant, corn seed, or corn plant part is diagnostic that the DNA was obtained from corn event MON95275. The invention thus provides a DNA molecule that contains at least one of the nucleotide sequences provided as SEQ ID NO:1, SEQ ID NO: 2, SEQ ID NO:3, SEQ ID NO:4, SEQ ID NO:5, SEQ ID NO:6, SEQ ID NO:7, SEQ ID NO: 8, SEQ ID NO:9, and SEQ ID NO: 10. Any segment of DNA derived from transgenic corn event MON95275 that is sufficient to include at least one of the sequences provided as SEQ ID NO: 1, SEQ ID NO:2, SEQ ID NO:3, SEQ ID NO:4, SEQ ID NO:5, SEQ ID NO:6, SEQ ID NO:7, SEQ ID NO:8, SEQ ID NO:9, and SEQ ID NO: 10 is within the scope of the invention. In addition, any polynucleotide comprising a sequence complementary to any of the sequences described within this paragraph is within the scope of the invention.

The invention provides exemplary DNA molecules that can be used either as primers or probes for detecting the presence of DNA derived from a corn plant comprising event MON95275 DNA in a sample. Such primers or probes are specific for a target nucleic acid sequence and, as such, are useful for the identification of corn event MON95275 nucleic acid sequence by the methods of the invention described herein.

It is intended by use of the word "derived" that a particular DNA molecule is in the corn plant genome, or is capable of being detected in corn plant DNA. "Capable of being detected" refers to the ability of a particular DNA segment to be amplified and its size or sequence characterized or elucidated by DNA sequence analysis, i.e., the target DNA segment, and the subsequent ability to detect the binding of the probe to the target. The particular DNA segment or target DNA segment of the present invention is present within corn that contains the insertion event MON95275.

A "probe" is a nucleic acid molecule that is complementary to (the reverse complement of) a strand of target nucleic acid and is useful in hybridization methods. A probe may be attached to a conventional detectable label or reporter molecule, e.g., a radioactive isotope, ligand, chemiluminescent agent, or enzyme. Such a probe is complementary to a strand of a target nucleic acid and, in the case of the present invention, to a strand of DNA from MON95275 whether from a MON95275 containing plant or from a sample that includes MON95275 DNA. Thus, the probes for use herein may comprise DNA molecules or polynucleotide segments of sufficient length to function under stringent hybridization conditions as defined herein to bind to a particular unique segment of DNA present within and diagnostic for event MON95275 in a sample. Such a probe can be designed to bind only to a single junction or other novel sequence present only in the corn event MON95275, or two or more such single junction segments. Probes according to the present invention include not only deoxyribonucleic or ribonucleic acids, but also polyamides and other probe materials that bind specifically to a target DNA sequence and can be used to detect the presence of that target DNA sequence. An exemplary DNA sequence useful as a probe for detecting corn event MON95275 is provided as SEQ ID NO: 17 (PB 10263).

A "primer" is typically a DNA molecule that is designed for use in specific annealing or hybridization methods that involve thermal amplification. Primers may comprise pairs of different oligonucleotides or polynucleotide segments for use in a thermal amplification reaction which amplifies a particular DNA target segment. Each primer in the pair is designed to bind to a rather specific segment of DNA within or near a segment DNA of interest for amplification. The primers bind in such a way that these then act as localized regions of nucleic acid sequence polymerization resulting in the production of one or more amplicons (amplified target segments of DNA). The amplicon produced from such reaction would have a DNA sequence corresponding to sequence of the template DNA located between the two sites where the primers hybridized to the template. In certain embodiments, use of primers designed to bind to unique segments of corn event MON95275 and that amplify particular amplicons containing one or more of the junction sequences described herein, and the detection and/or characterization of such amplicons upon completion or termination of polymerase reaction, is diagnostic for the presence of corn event MON95275 in a particular sample. The skilled artisan is well familiar with this amplification method and no recitation of the specifics of amplification is necessary here.

A primer is typically designed to hybridize to a complementary target DNA strand to form a hybrid between the primer and target DNA strand, and the presence of the primer is a point of recognition by a polymerase to begin extension of the primer (i.e., polymerization of additional nucleotides into a lengthening nucleotide molecule) using as a template the target DNA strand. Primer pairs refer to use of two primers binding opposite strands of a double stranded nucleotide segment for the purpose of amplifying linearly the polynucleotide segment between the positions targeted for binding by the individual members of the primer pair, typically in a thermal amplification reaction or other conventional nucleic-acid amplification methods. Exemplary DNA molecules useful as primers are provided as SEQ ID NO:15, SEQ ID NO: 16, SEQ ID NO:18, SEQ ID NO: 19, SEQ ID NO:21, and SEQ ID NO:22.

The primer pair SEQ ID NO:15 and SEQ ID NO: 16 are useful as a first DNA molecule and a second DNA molecule that is different from the first DNA molecule, and both are each of sufficient length of contiguous nucleotides of SEQ ID NO:10 to function as DNA primers that, when used together in a thermal amplification reaction with template DNA derived from corn event MON95275, to produce an amplicon diagnostic for corn event MON95275 DNA in a sample. The primer pair SEQ ID NO:18 and SEQ ID NO:19 are useful as a first DNA molecule and a second DNA molecule that is different from the first DNA molecule, and both are each of sufficient length of contiguous nucleotides of a locus within the corn genome to function as DNA primers that, when used together in a thermal amplification reaction with template DNA derived from corn event MON95275, to produce an amplicon that serves as an internal control for both the diagnosis of corn event MON95275, as well as the zygosity of corn event MON95275 DNA in a sample. The primer pair SEQ ID NO:21 and SEQ ID NO:22 are useful as a first DNA molecule and a second DNA molecule that is different from the first DNA molecule, and both are each of sufficient length of contiguous nucleotides of a locus within the corn genome to function as DNA primers that, when used together in a thermal amplification reaction with template DNA derived from corn event MON95275, to produce an amplicon diagnostic for non-inserted wild-type corn genomic DNA not comprising event MON95275.

DNA probes and DNA primers are generally eleven (11) polynucleotides or more in length, often eighteen (18) polynucleotides or more, twenty-four (24) polynucleotides or more, or thirty (30) polynucleotides or more. Such probes and primers are selected to be of sufficient length to hybridize specifically to a target sequence under high stringency hybridization conditions. Preferably, probes and primers according to the present invention have complete sequence similarity with the target sequence, although probes differing from the target sequence that retain the ability to hybridize to target sequences may be designed by conventional methods.

The nucleic acid probes and primers of the present invention hybridize under stringent conditions to a target DNA molecule. Any conventional nucleic acid hybridization or amplification method can be used to identify the presence of DNA from a transgenic plant in a sample. Polynucleic acid molecules also referred to as nucleic acid segments or fragments thereof are capable of specifically hybridizing to other nucleic acid molecules under certain circumstances.

As used herein, two polynucleic acid molecules are said to be capable of specifically hybridizing to one another if the two molecules are capable of forming an anti-parallel, double-stranded nucleic acid structure. A nucleic acid molecule is said to be the "complement" of another nucleic acid molecule if they exhibit complete complementarity. As used herein, molecules are said to exhibit "complete complementarity" when every nucleotide of one of the molecules is complementary to a nucleotide of the other. Two molecules are said to be "minimally complementary" if they can hybridize to one another with sufficient stability to permit them to remain annealed to one another under at least conventional "low-stringency" conditions. Similarly, the molecules are said to be "complementary" if they can hybridize to one another with sufficient stability to permit them to remain annealed to one another under conventional "high-stringency" conditions. Conventional stringency conditions are described by Sambrook et al., 1989, and by Hames et al., In: Nucleic Acid Hybridization, A Practical Approach, IRL Press, Washington, DC (1985). Departures from complete complementarity are therefore permissible, as long as such departures do not completely preclude the capacity of the molecules to form a double-stranded structure. In order for a nucleic acid molecule to serve as a primer or probe it need only be sufficiently complementary in sequence to be able to form a stable double-stranded structure under the particular solvent and salt concentrations employed.

As used herein, a substantially homologous sequence is a nucleic acid sequence that will specifically hybridize to the complement of the nucleic acid sequence to which it is being compared under high stringency conditions. Appropriate stringency conditions that promote DNA hybridization, for example, 6.0× sodium chloride/sodium citrate (SSC) at about 45° C., followed by a wash of 2.0×SSC at 50° C., are known to those skilled in the art or can be found in *Current Protocols in Molecular Biology*, John Wiley & Sons, N.Y. (1989), 6.3.1-6.3.6. For example, the salt concentration in the wash step can be selected from a low stringency of about 2.0×SSC at 50° C. to a high stringency of about 0.2×SSC at 50° C. In addition, the temperature in the wash step can be increased from low stringency conditions at room temperature, about 22° C., to high stringency conditions at about 65° C. Both temperature and salt may be varied, or either the temperature or the salt concentration may be held constant while the other variable is changed. In a preferred embodiment, a polynucleic acid of the present invention will specifically hybridize to one or more of the nucleic acid molecules set forth in SEQ ID NO: 1, SEQ ID NO:2, SEQ ID NO:3, SEQ ID NO:4, SEQ ID NO:5, SEQ ID NO:6, SEQ ID NO:7, SEQ ID NO:8, SEQ ID NO:9, or SEQ ID NO:10, or complements thereof or fragments of either under moderately stringent conditions, for example at about 2.0×SSC and about 65° C. In a particularly preferred embodiment, a nucleic acid of the present invention will specifically hybridize to one or more of the nucleic acid molecules set forth in SEQ ID NO: 1, SEQ ID NO:2, SEQ ID NO:3, SEQ ID NO:4, SEQ ID NO:5, SEQ ID NO:6, SEQ ID NO:7, SEQ ID NO:8, SEQ ID NO:9, or SEQ ID NO: 10, or complements or fragments of either under high stringency conditions. In one aspect of the present invention, a preferred marker nucleic acid molecule of the present invention has the nucleic acid sequence set forth in SEQ ID NO:1, or SEQ ID NO:2, or SEQ ID NO:3, or SEQ ID NO:4, or SEQ ID NO:5, or SEQ ID NO:6, or SEQ ID NO:7, or SEQ ID NO:8, or SEQ ID NO:9, or SEQ ID NO: 10, or complements thereof, or fragments of either. The hybridization of the probe to the target DNA molecule can be detected by any number of methods known to those skilled in the art, these can include, but are not limited to, fluorescent tags, radioactive tags, antibody-based tags, and chemiluminescent tags.

Regarding the amplification of a target nucleic acid sequence (e.g., by PCR) using a particular amplification primer pair, "stringent conditions" are conditions that permit the primer pair to hybridize only to the target nucleic acid sequence to which a primer having the corresponding wild-type sequence (or its complement) would bind and preferably to produce a unique amplification product, the amplicon, in a DNA thermal amplification reaction.

The term "specific for (a target sequence)" indicates that a probe or primer hybridizes under stringent hybridization conditions only to the target sequence in a sample comprising the target sequence.

As used herein, "amplified DNA" or "amplicon" refers to the product of polynucleic acid amplification method directed to a target polynucleic acid molecule that is part of a polynucleic acid template. For example, to determine whether a corn plant resulting from a sexual cross contains transgenic plant genomic DNA from a corn plant comprising event MON95275 of the present invention, DNA that is extracted from a corn plant tissue sample may be subjected to a polynucleic acid amplification method using a primer pair that includes a first primer derived from a genomic DNA sequence in the region flanking the heterologous inserted DNA of event MON95275 and is elongated by polymerase 5' to 3' in the direction of the inserted DNA. The second primer is derived from the heterologous inserted DNA molecule is elongated by the polymerase 5' to 3' in the direction of the flanking genomic DNA from which the first primer is derived. The amplicon may range in length from the combined length of the primer pair plus one nucleotide base pair, or plus about fifty nucleotide base pairs, or plus about two hundred-fifty nucleotide base pairs, or plus about four hundred-fifty nucleotide base pairs or more. Alternatively, a primer pair can be derived from genomic sequence on both sides of the inserted heterologous DNA so as to produce an amplicon that includes the entire insert polynucleotide sequence (e.g., a forward primer isolated from the genomic portion on the 5' end of SEQ ID NO: 10 and a reverse primer isolated from the genomic portion on the 3' end of SEQ ID NO: 10 that amplifies a DNA molecule comprising the inserted DNA sequence (SEQ ID NO:9) identified herein in the event MON95275 genome). A member of a primer pair derived from the plant genomic sequence adjacent to the inserted transgenic DNA is located a distance from the inserted DNA sequence, this distance can range from one nucleotide base pair up to about twenty thousand nucleotide base pairs. The use of the term "amplicon" specifically excludes primer dimers that may be formed in the DNA thermal amplification reaction.

For practical purposes, one should design primers which produce amplicons of a limited size range, for example, between 100 to 1000 bases. Smaller (shorter polynucleotide length) sized amplicons in general are more reliably produced in thermal amplification reactions, allow for shorter cycle times, and can be easily separated and visualized on agarose gels or adapted for use in endpoint TAQMAN®-like assays. Smaller amplicons can be produced and detected by methods known in the art of DNA amplicon detection. In addition, amplicons produced using the primer pairs can be cloned into vectors, propagated, isolated, and sequenced or can be sequenced directly with methods well established in the art. Any primer pair derived from the combination of SEQ ID NO: 11 and SEQ ID NO:9 or the combination of SEQ ID NO: 12 and SEQ ID NO:9 that are useful in a DNA amplification method to produce an amplicon diagnostic for MON95275 or progeny thereof is an aspect of the invention. Any single isolated DNA polynucleotide primer molecule comprising at least 15 contiguous nucleotides of SEQ ID NO:11, or its complement that is useful in a DNA amplification method to produce an amplicon diagnostic for MON95275 or progeny thereof is an aspect of the invention. Any single isolated DNA polynucleotide primer molecule comprising at least 15 contiguous nucleotides of SEQ ID NO: 12, or its complement that is useful in a DNA amplification method to produce an amplicon diagnostic for plants comprising MON95275 or progeny thereof is an aspect of the invention. Any single isolated DNA polynucleotide primer molecule comprising at least 15 contiguous nucleotides of SEQ ID NO:9, or its complement that is useful in a DNA amplification method to produce an amplicon diagnostic for MON95275 or progeny thereof is an aspect of the invention.

Polynucleic acid amplification can be accomplished by any of the various polynucleic acid amplification methods known in the art, including the polymerase chain reaction (PCR). Amplification methods are known in the art and are described, inter alia, in U.S. Pat. Nos. 4,683,195 and 4,683,202 and in *PCR Protocols: A Guide to Methods and Applications*, ed. Innis et al., Academic Press, San Diego, 1990. PCR amplification methods have been developed to amplify up to 22 kb (kilobase) of genomic DNA and up to 42 kb of bacteriophage DNA (Cheng et al., *Proc. Natl. Acad. Sci. USA* 91:5695-5699, 1994). These methods as well as other methods known in the art of DNA amplification may be used in the practice of the present invention. The sequence of the heterologous DNA insert or flanking genomic DNA sequence from corn event MON95275 can be verified (and corrected if necessary) by amplifying such DNA molecules from corn seed containing event MON95275 DNA or corn plants grown from the corn seed containing event MON95275 DNA deposited with the ATCC having accession No. PTA-126049, using primers derived from the sequences provided herein, followed by standard DNA sequencing of the PCR amplicon or cloned DNA fragments thereof.

The diagnostic amplicon produced by these methods may be detected by a plurality of techniques. One such method is Genetic Bit Analysis (Nikiforov, et al. Nucleic Acid Res. 22:4167-4175, 1994) where a DNA oligonucleotide is designed that overlaps both the adjacent flanking genomic DNA sequence and the inserted DNA sequence. The oligonucleotide is immobilized in wells of a microtiter plate. Following PCR of the region of interest (using one primer in the inserted sequence and one in the adjacent flanking genomic sequence), a single-stranded PCR product can be hybridized to the immobilized oligonucleotide and serve as a template for a single base extension reaction using a DNA polymerase and labeled dideoxynucleotide triphosphates (ddNTPs) specific for the expected next base. Readout may be fluorescent or ELISA-based. A signal indicates presence of the transgene/genomic sequence due to successful amplification, hybridization, and single base extension.

Another method is the Pyrosequencing technique as described by Winge (Innov. Pharma. Tech. 00:18-24, 2000). In this method, an oligonucleotide is designed that overlaps the adjacent genomic DNA and insert DNA junction. The oligonucleotide is hybridized to single-stranded PCR product from the region of interest (one primer in the inserted sequence and one in the flanking genomic sequence) and incubated in the presence of a DNA polymerase, ATP, sulfurylase, luciferase, apyrase, adenosine 5' phosphosulfate and luciferin. DNTPs are added individually and the incorporation results in a light signal that is measured. A light signal indicates the presence of the transgene/genomic sequence due to successful amplification, hybridization, and single or multi-base extension.

Fluorescence Polarization as described by Chen, et al., (Genome Res. 9:492-498, 1999) is a method that can be used to detect the amplicon of the present invention. Using this method an oligonucleotide is designed that overlaps the genomic flanking and inserted DNA junction. The oligonucleotide is hybridized to single-stranded PCR product from the region of interest (one primer in the inserted DNA and one in the flanking genomic DNA sequence) and incubated in the presence of a DNA polymerase and a fluorescent-labeled ddNTP. Single base extension results in incorporation of the ddNTP. Incorporation can be measured as a change in polarization using a fluorometer. A change in polarization indicates the presence of the transgene/genomic sequence due to successful amplification, hybridization, and single base extension.

Real-time Polymerase Chain Reaction (PCR) is the ability to monitor the progress of the PCR as it occurs (i.e., in real time). Data is collected throughout the PCR process, rather than at the end of the PCR. In real-time PCR, reactions are characterized by the point in time during cycling when amplification of a target is first detected rather than the amount of target accumulated after a fixed number of cycles. In a real-time PCR assay, a positive reaction is detected by accumulation of a fluorescent signal. The higher the starting copy number of the nucleic acid target, the sooner a significant increase in fluorescence is observed. The cycle threshold (Ct value) is defined as the number of cycles required for the fluorescent signal to cross the threshold (i.e., exceeds background level). Ct levels are inversely proportional to the amount of target nucleic acid in the sample (i.e., the lower the Ct value, the greater the amount of target nucleic acid in the sample).

Taqman® (PE Applied Biosystems, Foster City, CA) is described as a method of detecting and quantifying the presence of a DNA sequence using real-time PCR and is fully understood in the instructions provided by the manufacturer. Briefly, a FRET oligonucleotide probe is designed that overlaps the genomic flanking and insert DNA junction. The FRET probe and PCR primers (one primer in the insert DNA sequence and one in the flanking genomic sequence) are cycled in the presence of a thermalstable polymerase and dNTPs. Hybridization of the FRET probe results in cleavage and release of the fluorescent moiety away from the quenching moiety on the FRET probe. A fluorescent signal indicates the presence of the transgene/genomic sequence due to successful amplification and hybridization.

Molecular Beacons have been described for use in sequence detection as described in Tyangi, et al. (Nature Biotech. 14:303-308, 1996). Briefly, a FRET oligonucleotide probe is designed that overlaps the flanking genomic and insert DNA junction. The unique structure of the FRET probe results in it containing secondary structure that keeps the fluorescent and quenching moieties in close proximity. The FRET probe and PCR primers (one primer in the insert DNA sequence and one in the flanking genomic sequence) are cycled in the presence of a thermalstable polymerase and dNTPs. Following successful PCR amplification, hybridization of the FRET probe to the target sequence results in the removal of the probe secondary structure and spatial separation of the fluorescent and quenching moieties. A fluorescent signal results. A fluorescent signal indicates the presence of the flanking/transgene insert sequence due to successful amplification and hybridization.

DNA detection kits that are based on DNA amplification methods contain DNA primer molecules that hybridize specifically to a target DNA and amplify a diagnostic amplicon under the appropriate reaction conditions. The kit may provide an agarose gel based detection method or any number of methods of detecting the diagnostic amplicon that are known in the art. DNA detection kits can be developed using the compositions disclosed herein and are useful for identification of corn event MON95275 DNA in a sample and can be applied to methods for breeding corn plants containing event MON95275 DNA. A kit that contains DNA primers that are homologous or complementary to any portion of the corn genomic region as set forth in SEQ ID NO:10 and to any portion of the inserted transgenic DNA as set forth in SEQ ID NO:10 is an object of the invention. The DNA molecules can be used in DNA amplification methods (PCR) or as probes in polynucleic acid hybridization methods, i.e., southern analysis, northern analysis.

Probes and primers according to the invention may have complete sequence identity with the target sequence, although primers and probes differing from the target sequence that retain the ability to hybridize preferentially to target sequences may be designed by conventional methods. In order for a nucleic acid molecule to serve as a primer or probe it need only be sufficiently complementary in sequence to be able to form a stable double-stranded structure under the particular solvent and salt concentrations employed. Any conventional nucleic acid hybridization or amplification method can be used to identify the presence of transgenic DNA from corn event MON95275 in a sample. Probes and primers are generally at least about 11 nucleotides, at least about 18 nucleotides, at least about 24 nucleotides, or at least about 30 nucleotides or more in length. Such probes and primers hybridize specifically to a target DNA sequence under stringent hybridization conditions. Conventional stringency conditions are described by Sambrook et al., 1989, and by Hames et al., In: *Nucleic Acid Hybridization, A Practical Approach*, IRL Press, Washington, DC (1985).

Any number of methods well known to those skilled in the art can be used to isolate and manipulate a DNA molecule, or fragment thereof, disclosed in the invention, including thermal amplification methods. DNA molecules, or fragments thereof, can also be obtained by other techniques such as by directly synthesizing the fragment by chemical means, as is commonly practiced by using an automated oligonucleotide synthesizer.

The DNA molecules and corresponding nucleotide sequences provided herein are therefore useful for, among other things, identifying corn event MON95275, detecting the presence of DNA derived from the transgenic corn event MON95275 in a sample, and monitoring samples for the presence and/or absence of corn event MON95275 or plant parts derived from corn plants comprising event MON95275.

By reference to corn it is intended that corn plants, corn plant cells, corn seeds, corn plant parts, corn progeny plants, and corn commodity products are within the scope of the invention, so long as each embodiment contains a detectable amount of DNA corresponding to any one, two, or more of the segments described herein as being diagnostic for the presence of corn event MON95275 (e.g., such as a polynucleotide having at least one of the sequences provided as SEQ ID NO: 1, SEQ ID NO:2, SEQ ID NO:3, SEQ ID NO:4, SEQ ID NO:5, SEQ ID NO:6, SEQ ID NO: 7, SEQ ID NO:8, SEQ ID NO:9, and SEQ ID NO:10). Corn plants, plant cells, seeds, plant parts, and progeny plants of the invention may also contain one or more additional transgenes. Such additional transgene may be any nucleotide sequence encoding a protein or RNA molecule conferring a desirable trait including but not limited to increased insect resistance, increased water use efficiency, increased yield performance, increased drought resistance, increased seed quality, and/or increased herbicide tolerance.

The invention provides corn plants, corn plant cells, corn seeds, corn plant parts (such as pollen, ovule, silk, spike, anther, cob, root tissue, stalk tissue, leaf tissue as well as seed), corn progeny plants derived from a transgenic corn plant containing MON95275 DNA. A representative sample of corn seed containing event MON95275 DNA has been deposited according to the Budapest Treaty with the American Type Culture Collection (ATCC®). The ATCC repository has assigned the Patent Deposit Designation PTA-126049 to the seed containing event MON95275 DNA.

The invention provides a microorganism comprising a DNA molecule having at least one sequence selected from SEQ ID NO:1, SEQ ID NO:2, SEQ ID NO:3, SEQ ID NO:4, SEQ ID NO: 5, SEQ ID NO:6, SEQ ID NO:7, SEQ ID NO:8, SEQ ID NO:9, and SEQ ID NO: 10 present in its genome. A microorganism is intended to include any microscopic cell, whether prokaryote or eukaryote or otherwise that contains DNA within a genome or chromosome or an extra-chromosomal DNA structure more commonly referred to as a plasmid or vector. Microscopic organisms include bacteria (prokaryotes) and cells corresponding to higher life forms (eukaryotes) which are beneath the visual range of the average human. An example of such a microorganism is a transgenic plant cell.

Microorganisms, such as a plant cell of the invention, are useful in many industrial applications, including but not limited to: (i) use as research tool for scientific inquiry or industrial research; (ii) use in culture for producing endogenous or recombinant carbohydrate, lipid, nucleic acid, or protein products or small molecules that may be used for subsequent scientific research or as industrial products; and (iii) use with modern plant tissue culture techniques to produce transgenic plants or plant tissue cultures that may then be used for agricultural research or production. The production and use of microorganisms such as transgenic plant cells utilizes modern microbiological techniques and human intervention to produce a man-made, unique microorganism. In this process, recombinant DNA is inserted into a plant cell's genome to create a transgenic plant cell that is separate and unique from naturally occurring plant cells. This transgenic plant cell can then be cultured much like bacteria and yeast cells using modern microbiology techniques and may exist in an undifferentiated, unicellular state. The transgenic plant cell's new genetic composition and phenotype is a technical effect created by the integration of the heterologous DNA into the genome of the cell. Another aspect of the invention is a method of using a microorganism of the invention. Methods of using microorganisms of the invention, such as transgenic plant cells, include (i) methods of producing transgenic cells by integrating recombinant DNA into the genome of the cell and then using this cell to derive additional cells possessing the same heterologous DNA; (ii) methods of culturing cells that contain recombinant DNA using modern microbiology techniques; (iii) methods of producing and purifying endogenous or recombinant carbohydrate, lipid, nucleic acid, or protein products from cultured cells; and (iv) methods of using modern plant tissue culture techniques with transgenic plant cells to produce transgenic plants or transgenic plant tissue cultures.

Plants of the invention may pass along the event MON95275 DNA, including transgene inserted in corn event MON95275, to progeny. As used herein, "progeny" includes any plant, plant cell, seed, and/or regenerable plant part containing the event MON95275 DNA derived from an ancestor plant and/or comprising a DNA molecule having at least one sequence selected from SEQ ID NO:1, SEQ ID NO:2, SEQ ID NO:3, SEQ ID NO:4, SEQ ID NO:5, SEQ ID NO:6, SEQ ID NO: 7, SEQ ID NO:8, SEQ ID NO:9, and SEQ ID NO: 10. Plants, progeny, and seeds may be homozygous or heterozygous for the transgene of event MON95275. Progeny may be grown from seed produced by a corn event MON95275 containing plant and/or from seed produced by a plant fertilized with pollen from a corn event MON95275 containing plant.

Progeny plants may be self-pollinated (also known as "selfing") to generate a true breeding line of plants, i.e., plants homozygous for the transgene. Selfing of appropriate progeny can produce plants that are homozygous for both added exogenous genes.

Alternatively, progeny plants may be out-crossed, e.g., bred with another unrelated plant, to produce a varietal or a hybrid seed or plant. The other unrelated plant may be transgenic or non-transgenic. A varietal or hybrid seed or plant of the invention may thus be derived by sexually crossing a first parent that lacks the specific and unique DNA of the corn event MON95275 with a second parent comprising corn event MON95275, resulting in a hybrid comprising the specific and unique DNA of the corn event MON95275. Each parent can be a hybrid or an inbred/varietal, so long as the cross or breeding results in a plant or seed of the invention, i.e., a seed having at least one allele containing the DNA of corn event MON95275 and/or a DNA molecule having at least one sequence selected from SEQ ID NO:1, SEQ ID NO:2, SEQ ID NO:3, SEQ ID NO:4, SEQ ID NO:5, SEQ ID NO:6, SEQ ID NO:7, SEQ ID NO:8, SEQ ID NO:9, and SEQ ID NO: 10. Two different transgenic plants may thus be crossed to produce hybrid offspring that contain two independently segregating, added, exogenous genes. For example, MON95275 containing Cry75Aa1, Vip4Da2, and DvSnf7 specific dsRNA conferring insect resistance to corn can be crossed with other transgenic corn plants to produce a plant having the characteristics of both transgenic parents. One example of this would be a cross of MON95275 containing Cry75Aa1, Vip4Da2, and DvSnf7 specific dsRNA mediated gene suppression, conferring Coleopteran resistance to corn with a plant having one or more additional traits such as herbicide tolerance, insect resistance, or drought tolerance, resulting in a progeny plant or seed that has resistance to Colcopteran insect pests and has at least one or more additional traits. Back-crossing to a parental plant and out-crossing with a non-transgenic plant are also contemplated, as is vegetative propagation. Descriptions of other breeding methods that are commonly used for different traits and crops can be found in one of several references, e.g., Fehr, in *Breeding Methods for Cultivar Development*, Wilcox J. ed., American Society of Agronomy, Madison WI (1987).

Plants, progeny, seed, cells and plant parts of the invention may also contain one or more additional corn trait(s) or transgenic events, particularly those introduced by crossing a corn plant containing corn event MON95275 with another corn plant containing the additional trait(s) or transgenic events. Such trait(s) or transgenic events include, but are not limited to, increased insect resistance, herbicide tolerance, increased water use efficiency, increased yield performance, increased drought resistance, increased seed quality, improved nutritional quality, hybrid seed production, or disease or fungal resistance. Corn transgenic events are known to those of skill in the art. For example, a list of such traits is provided by the United States Department of Agriculture's (USDA) Animal and Plant Health Inspection Service (APHIS) and can be found on the website aphis.usda.gov on the worldwide web. Two or more transgenic events may thus be combined in a progeny seed or plant by crossing two parent plants each comprising one or more transgenic events, collecting the progeny seed, and selecting for progeny seed or plants that contain the two or more transgenic events. These steps may be repeated until the desired combination of transgenic events in a progeny is achieved. Back-crossing to a parental plant and out-crossing with a non-transgenic plant are also contemplated, and is vegetative propagation.

A plant part that is derived from corn plants comprising event MON95275 is also provided. As used herein, a "plant part" refers to any part of a plant which is comprised of material derived from a corn plant comprising event MON95275. Plant parts include but are not limited to seed, pollen, ovule, silk, spike, anther, cob, root tissue, stalk tissue, and leaf tissue. Plant parts may be viable, nonviable, regenerable, and/or nonregenerable.

Further provided is a commodity product that is derived from corn plants comprising event MON95275 and that contains a detectable amount of a nucleic acid specific for event MON95275. As used herein, a "commodity product" refers to any composition or product which is comprised of material derived from a corn plant, whole or processed corn seed, or one or more plant cells and/or plant parts containing the corn event MON95275 DNA. Nonviable commodity products include but are not limited to nonviable seeds, whole or processed seeds, seed parts, and plant parts; animal feed comprising corn, corn oil, corn meal, corn flour, corn flakes, corn bran, pasta made with corn, corn biomass, and fuel products produced using corn and corn parts. Viable commodity products include but are not limited to seeds, plants, and plant cells. The corn plants comprising event MON95275 can thus be used to manufacture any commodity product typically acquired from corn. Any such commodity product that is derived from corn plants comprising event MON95275 may contain at least a detectable amount of the specific and unique DNA corresponding to corn event MON95275, and specifically may contain a detectable amount of a polynucleotide comprising a DNA molecule having at least one sequence selected from SEQ ID NO: 1, SEQ ID NO:2, SEQ ID NO:3, SEQ ID NO:4, SEQ ID NO:5, SEQ ID NO:6, SEQ ID NO:7, SEQ ID NO:8, SEQ ID NO:9, and SEQ ID NO: 10. Any standard method of detection for nucleotide molecules may be used, including methods of detection disclosed herein. A commodity product is with the scope of the invention if there is any detectable amount of a DNA molecule having at least one sequence selected from SEQ ID NO:1, SEQ ID NO:2, SEQ ID NO:3, SEQ ID NO: 4, SEQ ID NO:5, SEQ ID NO:6, SEQ ID NO:7, SEQ ID NO:8, SEQ ID NO:9, and SEQ ID NO: 10 in the commodity product.

The corn plants, corn plant cells, corn seed, corn plant parts (such as pollen, ovule, silk, spike, anther, cob, root tissue, stalk tissue, leaf tissue), corn progeny plants, and commodity products of the invention are therefore, useful for, among other things, growing plants for the purpose of producing seed and/or plant parts comprising corn event MON95275 for agricultural purposes, producing progeny comprising corn event MON95275 for plant breeding and research purposes, use with microbiological techniques for industrial and research applications, and sale to consumers.

Methods for producing an insect resistant corn plant comprising the DNA sequences specific and unique to event MON95275 of the invention are provided. Transgenic plants used in these methods may be homozygous or heterozygous for the transgene. Progeny plants produced by these methods may be varietal or hybrid plants; may be grown from seed produced by corn event MON95275 containing plant and/or from seed produced by a plant fertilized with pollen from a corn event MON95275 containing plant; and may be homozygous or heterozygous for the transgene. Progeny plants may be subsequently self-pollinated to generate a true breeding line of plants, i.e., plants homozygous for the transgene, or alternatively may be out-crossed, e.g., bred with another unrelated plant, to produce a varietal or a hybrid seed or plant.

Methods of detecting the presence of DNA derived from a corn cell, corn tissue, corn seed, or corn plant comprising corn event MON95275 in a sample are provided. One method comprises (i) extracting a DNA sample from at least one corn cell, corn tissue, corn seed, or corn plant; (ii) contacting the DNA sample with at least one primer that is capable of producing DNA sequence specific to event MON95275 DNA under conditions appropriate for DNA sequencing; (iii) performing a DNA sequencing reaction; and then (iv) confirming that the nucleotide sequence comprises a nucleotide sequence specific for event MON95275, of the construct comprised therein, such as one selected from the group consisting of SEQ ID NO:1, SEQ ID NO:2, SEQ ID NO: 3, SEQ ID NO:4, SEQ ID NO:5, SEQ ID NO:6, SEQ ID NO:7, SEQ ID NO:8, SEQ ID NO:9, and SEQ ID NO:10. Another method comprises (i) extracting a DNA sample from at least one corn cell, corn tissue, corn seed, or corn plant; (ii) contacting the DNA sample with a primer pair that is capable of producing an amplicon from event MON95275 DNA under conditions appropriate for DNA amplification; (iii) performing a DNA amplification reaction; and then (iv) detecting the amplicon molecule and/or confirming that the nucleotide sequence of the amplicon comprises a nucleotide sequence specific for event MON95275, such as one selected from the group consisting of SEQ ID NO:1, SEQ ID NO:2, SEQ ID NO:3, SEQ ID NO:4, SEQ ID NO:5, and SEQ ID NO:6. The amplicon should be one that is specific for event MON95275, such as an amplicon that comprises SEQ ID NO:1, or SEQ ID NO:2, or SEQ ID NO:3, or SEQ ID NO:4, or SEQ ID NO:5, or SEQ ID NO:6. The detection of a nucleotide sequence specific for event MON95275 in the amplicon is determinative and/or diagnostic for the presence of the corn event MON95275 specific DNA in the sample. An example of a primer pair that is capable of producing an amplicon from event MON95275 DNA under conditions appropriate for DNA amplification is provided as SEQ ID NO:15 and SEQ ID NO:16. Other primer pairs may be readily designed by one of skill in the art and would produce an amplicon comprising SEQ ID NO: 1, or SEQ ID NO:2, or SEQ ID NO:3, or SEQ ID NO:4, or SEQ ID NO:5, or SEQ ID NO:6, wherein such a primer pair comprises at least on primer within the genomic region flanking the insert and a second primer within the insert. Another method of detecting the presence of DNA derived from a corn cell, corn tissue, corn seed, or corn plant comprising corn event MON95275 in a sample consists of (i) extracting a DNA sample from at least one corn cell, corn tissue, corn seed, or corn plant; (ii) contacting the DNA sample with a DNA probe specific for event MON95275 DNA; (iii) allowing the probe and the DNA sample to hybridize under stringent hybridization conditions; and then (iv) detecting hybridization between the probe and the target DNA sample. An example of the sequence of a DNA probe that is specific for event MON95275 is provided as SEQ ID NO:17. Other probes may be readily designed by one of skill in the art and would comprise at least one fragment of genomic DNA flanking the insert and at least one fragment of insert DNA such as sequence provided in, SEQ ID NO: 1, SEQ ID NO:2, SEQ ID NO:3, SEQ ID NO:4, SEQ ID NO:5, SEQ ID NO:6, SEQ ID NO:7, SEQ ID NO:8, and SEQ ID NO:10. Detection of probe hybridization to the DNA sample is diagnostic for the presence of corn event MON95275 specific DNA in the sample. Absence of hybridization is alternatively diagnostic of the absence of corn event MON95275 specific DNA in the sample.

DNA detection kits are provided that are useful for the identification of corn event MON95275 DNA in a sample and can also be applied to methods for breeding corn plants containing the appropriate event DNA. Such kits contain DNA primers and/or probes comprising fragments of SEQ ID NO: 1, SEQ ID NO:2, SEQ ID NO:3, SEQ ID NO:4, SEQ ID NO:5, SEQ ID NO: 6, SEQ ID NO:7, SEQ ID NO:8, SEQ ID NO:9, and SEQ ID NO: 10. One example of such a kit comprises at least one DNA molecule of sufficient length of continuous nucleotides of SEQ ID NO: 10 to function as a DNA probe useful for detecting the presence and/or absence of DNA derived from transgenic corn plants comprising event MON95275 in a sample. The DNA derived from transgenic corn plants comprising event MON95275 would comprise a DNA molecule having at least one sequence selected from SEQ ID NO:1, SEQ ID NO:2, SEQ ID NO:3, SEQ ID NO: 4, SEQ ID NO:5, SEQ ID NO:6, SEQ ID NO:7, SEQ ID NO:8, SEQ ID NO:9, and SEQ ID NO: 10. A DNA molecule sufficient for use as a DNA probe is provided that is useful for determining, detecting, or diagnosing the presence and/or absence of corn event MON95275 DNA in a sample is provided as SEQ ID NO: 17. Other probes may be readily designed by one of skill in the art and should comprise at least 15, at least 16, at least 17, at least 18, at least 19, at least 20, at least 21, at least 22, at least 23, at least 24, at least 25, at least 26, at least 27, at least 28, at least 29, at least 30, at least 31, at least 32, at least 33, at least 34, at least 35, at least 36, at least 37, at least 38, at least 39, or at least 40 contiguous nucleotides of SEQ ID NO:10 and be sufficiently unique to corn event MON95275 DNA in order to identify DNA derived from the event.

Another type of kit comprises a primer pair useful for producing an amplicon useful for detecting the presence and/or absence of DNA derived from transgenic corn event MON95275 in a sample. Such a kit would employ a method comprising contacting a target DNA sample with a primer pair as described herein, then performing a nucleic acid amplification reaction sufficient to produce an amplicon comprising a DNA molecule having at least one sequence selected from SEQ ID NO: 1, SEQ ID NO:2, SEQ ID NO:3, SEQ ID NO:4, SEQ ID NO:5, SEQ ID NO:6, SEQ ID NO: 7, SEQ ID NO:8, SEQ ID NO:9, and SEQ ID NO: 10 and then detecting the presence and/or absence of the amplicon. Such a method may also include sequencing the amplicon or a fragment thereof, which would be determinative of, i.e., diagnostic for, the presence of the corn event MON95275 specific DNA in the target DNA sample. Other primer pairs may be readily designed by one of skill in the art and should comprise at least 15, at least 16, at least 17, at least 18, at least 19, at least 20, at least 21, at least 22, at least 23, at least 24, at least 25, at least 26, at least 27, at least 28, at least 29, or at least 30 contiguous nucleotides of sequences provided in, but not limited to SEQ ID NO:1, SEQ ID NO:2, SEQ ID NO:3, SEQ ID NO:4, SEQ ID NO:5, SEQ ID NO:6, SEQ ID NO:7, SEQ ID NO:8, SEQ ID NO:9, and SEQ ID NO: 10, and be sufficiently unique to corn event MON95275 DNA in order to identify DNA derived from the event.

The kits and detection methods of the invention are useful for, among other things, identifying corn event MON95275, selecting plant varieties or hybrids comprising corn event MON95275, detecting the presence of DNA derived from the transgenic corn plant comprising event MON95275 in a sample, and monitoring samples for the presence and/or absence of corn plants comprising event MON95275, or plant parts derived from corn plants comprising event MON95275.

The sequences of the heterologous DNA insert, junction sequences, or flanking sequence from corn event MON95275 can be verified (and corrected if necessary) by amplifying such sequences from the event using primers derived from the sequences provided herein followed by standard DNA sequencing of the amplicon or of the cloned DNA.

Methods of detecting the zygosity of the transgene allele of DNA derived from a corn cell, corn tissue, corn seed, or corn plant comprising corn event MON95275 in a sample are provided. One method comprises (i) extracting a DNA sample from at least one corn cell, corn tissue, corn seed, or corn plant; (ii) contacting the DNA sample with a primer pair that is capable of producing a first amplicon diagnostic for event MON95275; (iii) contacting the DNA sample with a primer pair that is capable of producing a second amplicon diagnostic for native corn genomic DNA not comprising event MON95275; (iv) performing a DNA amplification reaction; and then (v) detecting the amplicons, wherein the presence of only the first amplicon is diagnostic of a homozygous event MON95275 DNA in the sample, and the presence of both the first amplicon and the second amplicon is diagnostic of a corn plant heterozygous for event MON95275 allele. An exemplary set of primers pairs are presented as SEQ ID NO:15 and SEQ ID NO:16 which produce an amplicon diagnostic for event MON95275; and SEQ ID NO:21 and SEQ ID NO:22 which produces an amplicon diagnostic for the wild-type corn genomic DNA not comprising event MON95275. A set of probes can also be incorporated into such an amplification method to be used in a real-time PCR format using the primer pair sets described above. An exemplary set of probes are presented as SEQ ID NO: 17 (diagnostic for the amplicon for the event MON95275) and SEQ ID NO:23 (diagnostic for the amplicon for wild-type corn genomic DNA not comprising event MON95275).

Another method for determining zygosity comprises (i) extracting a DNA sample from at least one corn cell, corn tissue, corn seed, or corn plant; (ii) contacting the DNA sample with a probe set which contains at least a first probe that specifically hybridizes to event MON95275 DNA and at least a second probe that specifically hybridizes to corn genomic DNA that was disrupted by insertion of the heterologous DNA of event MON95275 and does not hybridize to event MON95275 DNA; (iii) hybridizing the probe set with the sample under stringent hybridization conditions, wherein detecting hybridization of only the first probe under the hybridization conditions is diagnostic for a homozygous allele of event MON95275 DNA in the sample; and wherein detecting hybridization of both the first probe and the second probe under the hybridization conditions is diagnostic for a heterozygous allele of event MON95275 in a DNA sample.

Yet another method for determining zygosity comprises (i) extracting a DNA sample from at least one corn cell, corn tissue, corn seed, or corn plant; (ii) contacting the DNA sample with a primer pair that is capable of producing an amplicon diagnostic for the allele of event MON95275; (iii) contacting the DNA sample with a primer pair that is capable of producing an amplicon of an internal standard known to be single-copy and homozygous in the corn plant; (iv) contacting the DNA sample with a probe set which contains at least a first probe that specifically hybridizes to the allele of event MON95275, and at least a second probe that specifically hybridizes to the internal standard genomic DNA known to be single-copy and homozygous in the corn plant; (v) performing a DNA amplification reaction using real-time PCR and determining the cycle thresholds (Ct values) of the amplicon corresponding to the toxin coding sequence and the single-copy, homozygous internal standard; (vi) calculating the difference ($\Delta$Ct) between the Ct value of the single-copy, homozygous internal standard amplicon and the Ct value of the toxin coding sequence amplicon; and (vii) determining zygosity, wherein a $\Delta$Ct of around zero (0) indicates homozygosity of the inserted T-DNA and a $\Delta$Ct of around one (1) indicates heterozygosity of the inserted T-DNA. Heterozygous and homozygous events are differentiated by a $\Delta$Ct value unit of approximately one (1). Given the normal variability observed in real-time PCR due to multiple factors such as amplification efficiency and ideal annealing temperatures, the range of "about one (1)" is defined as a $\Delta$Ct of 0.75 to 1.25. Primer pairs and probes for the above method for determining zygosity can amplify and detect amplicons from the allele of event MON95275 and internal standard. Exemplary primer pairs for the detection of the amplicons corresponding to the allele of event MON95275 and internal standard are presented as SEQ ID NO:15 combined with SEQ ID NO:16 (allele of event MON95275) and SEQ ID NO:18 combined with SEQ ID NO:19 (internal standard). The accompanying exemplary probes are presented as SEQ ID NO: 17 (allele of event MON95275) and SEQ ID NO:20 (internal standard).

Deposit Information

A deposit of a representative sample of corn seed containing event MON95275 was made on Aug. 21, 2019, according to the Budapest Treaty with the American Type Culture Collection (ATCC) having an address at 10801 University Boulevard, Manassas, Virginia USA, Zip Code 20110. The deposit was accepted and assigned ATCC Accession No. PTA-126049. Access to the deposits will be available during the pendency of the application to the Commissioner of Patents and Trademarks and persons determined by the Commissioner to be entitled thereto upon request. Upon issuance of the patent, all restrictions upon availability to the public will be irrevocably removed. The deposit will be maintained in the depository for a period of thirty (30) years, or five (5) years after the last request, or for the effective life of the patent, whichever is longer, and will be replaced as necessary during that period.

EXAMPLES

The following Examples are included to more fully describe the invention, resulting from the construction and testing of 163 constructs, the production of about 2,300 events, and the analysis of hundreds of thousands of individual plants over 6 years through the rigorous molecular, agronomic, and field testing required for the creation and selection of corn event MON95275.

Those of skill in the art should, in light of the present disclosure, appreciate that many changes can be made in the specific embodiments that are disclosed and still obtain a like or similar result without departing from the spirit and scope of the invention.

Example 1

Expression Cassette Testing, Construct Design, Plant Testing and Construct Selection It is often necessary to create and screen a large number of gene expression constructs and transformation events in order to identify a construct, and then an event, which demonstrates optimal expression of the introduced genes of interest, while also not producing agronomic or phenotypic off-types.

For these reasons, the development of a transgenic corn plant producing insecticidal proteins active against Coleopteran insects without any negative effects on agronomics, yield, or stacking viability, required extensive research, development, and analysis. Specifically, over a 6 year period, over 4,531 proof of concept and commercial transgenic events derived from 163 different plasmid vector constructs were developed, tested, and analyzed.

This Example describes the design and testing in corn plants of 163 different constructs, to identify the preferred construct for event creation. Each construct varied with respect to the coding sequences for the insecticidal proteins and the transcriptional regulatory elements, and these were tested to select the preferred construct for use in expressing the insecticidal proteins in plants. Each construct had a unique configuration, varying by expression cassette composition (both insecticidal proteins, dsRNAs, and expression elements), orientation, and whether or not proteins were targeted for insertion into chloroplasts.

In an initial proof of concept and developmental stage, 160 constructs comprising different combinations of 26 distinct promoters, 14 distinct enhancers, 14 distinct introns, 16 distinct insect toxin coding sequences, 16 distinct dsRNA encoding sequences, and 14) distinct 3' UTRs were used to generate over 2,000 transformed events. After initial molecular characterization for the presence of the transgene(s), 1,875 single transformed corn events were selected for further characterization and efficacy testing. These events were evaluated for phenotypic or agronomic off-types, the level of expression of the insect toxin proteins, and efficacy against selected Coleopteran insect pest species. The resulting efficacy and protein expression data, along with any information regarding phenotypic and agronomic off-types, was used to eliminate inefficacious proteins, expression elements, and combinations, and was used to design a smaller number of binary commercial transformation plasmid constructs to be used in the next phase of development. This proof of concept testing stage in the development of MON95275 is identified as "POC Transformation and Assay" in the timeline presented in FIG. 3.

In the next phase of development, 3 new constructs were created. These constructs comprised combinations of 1 to 2 insect toxin transgene expression cassettes and 1 dsRNA expression cassette in different orientations (convergent or divergent). These 3 constructs were used to generate transformed events (also referred to as "transformants"). After shoot formation in culture, a subset of the transformed events were selected based upon visual characteristics and early molecular analysis. After initial transformation, 2,531 transformants were transferred to soil. 1,496 events were discarded after initial molecular characterization. Of the remaining 1,035 events 427 were eliminated based upon observations of plant health. The remaining 608 events were transplanted to pots and grown in the greenhouse (GH) for further assay. Leaf samples of each event were used to measure expression of DvSnf7 specific dsRNA using a QuantiGene® assay and expressed as femtograms DvSnf7 RNA per total micrograms RNA (fg DvSnf7/ug RNA). A range of expression of 1,000-3,000 fg DvSnf7 dsRNA/ug RNA was used to select events for further study. Of the remaining 608 events, 425 events were found to express DvSnf7 dsRNA with the range of expression of 1,000-3,000 fg DvSnf7 dsRNA/ug RNA. 19 of the remaining 425 events were eliminated based upon lack of expression of the insect toxin proteins, resulting in a total of 406 events for further assay and characterization. The $R_0$ events were allowed to self-pollinate and produce $R_1$ seed. Based upon observations of plant health and seed return, 152 events were discarded, leaving a total of 254 events for further study. After further molecular characterization, 102 events were discarded, leaving a total of 152 events for $R_1$ nursery for efficacy studies, additional molecular characterization, expression studies, and seed return and segregation analysis. This commercial transformation and $R_0$ screen stage in the development of event MON95275 is identified as "Comm. TFN $R_0$ Screen" in the timeline presented in FIG. 3.

Since corn rootworm plant assays are destructive assays, requiring the plant to be removed from the pot in order to assess overall root damage, the $R_0$ plants are used to produce $R_1$ seed so that there are sufficient seed to continue generations of each selected event for further efficacy and agronomic assessments, as well as further molecular characterization. Plants derived from the $R_1$ seed were assayed for efficacy against Western Corn Rootworm (*Diabrotica virgifera virgifera*, WCR) and Northern Corn Rootworm (*Diabrotica barberi*, NCR). Based upon the efficacy studies, additional molecular characterization, expression studies, and seed return and segregation analysis, 57 events derived from the 3 constructs were advanced for further analysis. This $R_1$ stage efficacy/molecular screen is identified as "GH/Mol. Screen" in FIG. 3. After the $R_1$ stage efficacy/molecular screen, events derived from one construct (Construct-2 in Table 2) were discarded based upon decisions regarding the construct configuration and toxin expression cassettes.

Table 2 shows the number of events remaining corresponding to each construct for each step of selection described above corresponding to each construct. Plasmid construct pM95275 was the construct used in transformation that produced corn event MON95275.

Vip4Da2 toxins, and 7 events were discarded based upon the assays, leaving a total of 130 for the $R_0$ screen. After the $R_0$ screen, 52 events were discarded due to poor seed return or plant health, leaving a total of 78 for further molecular characterization. After molecular characterization there were 56 remaining events.

The remaining 56 events were sent to the $R_1$ nursery for further testing. From the $R_1$ nursery, an additional 8 events were discarded due to poor seed return and segregation analysis and 21 events were discarded due to concerns regarding protein expression and molecular characterization, leaving 19 events.

The remaining 19 events advanced to the R2/F1 Cre crossing phase in which the CP4 marker cassette was removed through breeding. During the R2/F1 Cre crossing phase, 12 events were discarded, 7 due to additional molecular characterization and 5 based upon concerns regarding agronomic performance and other molecular studies.

TABLE 2

Events per construct selected for continued study.

| Construct | Events to Soil | Passed Initial Molecular Quality | $R_0$ Transpl. GH | DvSnf7 dsRNA Exp. | GOI | Seed Return/Plant Health | $R_0$ After Molecular | R1 GH/Mol. Screen |
|---|---|---|---|---|---|---|---|---|
| Construct-1 | 1126 | 539 | 306 | 172 | 168 | 99 | 54 | 18 |
| Construct-2 | 771 | 262 | 162 | 116 | 108 | 77 | 42 | 20 |
| Construct pM95275 | 634 | 234 | 140 | 137 | 130 | 78 | 56 | 19 |
| Total | 2531 | 1035 | 608 | 425 | 406 | 254 | 152 | 57 |

The 2017 US field efficacy trials reduced the collective number of events to 14 from Construct-1 and Construct pM95275 based upon efficacy, phenotypic observations, and molecular studies such as insertion site integration.

Events derived from Construct-1 in Table 2 were discarded based upon decisions regarding insecticidal protein expression.

Thus, numerous rounds of testing and comparison of various constructs revealed that events produced using the transgene cassette provided as SEQ ID NO: 13, Construct pM95275, provided preferred efficacy against the Coleopteran pest species Western Corn Rootworm (*Diabrotica virgifera virgifera*, WCR) and Northern Corn Rootworm (*Diabrotica barberi*, NCR), and preferred molecular characterization and agronomic performance.

Example 2

Field Trials, Molecular Testing and Event Selection

This Example describes the molecular characterization, analysis, and testing in field trials of events created with Construct pM95275 in multiple locations over several years, which lead to the selection of the final event, MON95275.

Table 3 illustrates the process used to select the event MON95275. At the commercial transformation $R_0$ screen, one hundred forty (140) $R_0$ transformed events from Construct pM95275 were derived and selected for growth. After quantification of the DvSnf7 expression, 3 events were discarded which did not meet the criteria for an expression range of 1,000-3,000 fg DvSnf7 dsRNA/ug RNA, leaving a total of 137 events for further assay. The remaining 137 events were assayed for expression of the Cry75Aa1 and The remaining 7 events proceeded to the 2017 U.S. field trials. After the field trials, 3 of the remaining 7 events were discarded, 1 as a result of an off phenotype observed in the field and 2 which performed less well than the others with respect to efficacy and agronomics, leaving 4 events for the 2018 U.S. field trials. During the 2018 US field trials, 1 event was discarded due to an incorrect transcription pattern from the DvSnf7 dsRNA expression cassette and 1 due to agronomic performance, leaving 2 events, Event 1 and event MON95275. After further analysis of the agronomics of the events from multiple field trials in the U.S. and Argentina, event MON95275 was selected as the event for commercialization because it ranked dsRNA higher than Event 1 when all the characteristics of molecular characterization, protein and DvSnf7 dsRNA expression, efficacy and agronomics of each event were compared.

TABLE 3

MON95275 event selection.

| Stage | Assay | Events Removed | Events Remaining 140 |
|---|---|---|---|
| Comm. TFN $R_0$ Screen | Expression-RNAi | 3 | 56 |
| | Expression-GOI | 7 | |
| | Seed Return/plant health | 52 | |
| | Molecular | 22 | |
| $R_1$ GH/Mol. Screen | Nursery return/Segregation | 8 | 19 |
| | Efficacy | 0 | |
| | Expression + Molecular | 21 | |

TABLE 3-continued

| MON95275 event selection. | | | |
|---|---|---|---|
| Stage | Assay | Events Removed | Events Remaining 140 |
| R2/F1 Cre Crossing | Efficacy | 0 | 7 |
| | Pre-GSS molecular | 7 | |
| | Expression | 0 | |
| | Agronomics + Molecular | 5 | |
| 2017 US Field | Agronomics | 0 | 4 |
| | Phenotype | 1 | |
| | Efficacy | 0 | |
| | Lesser Performer for GSS | 2 | |
| 2018 US Field | DvSnf7 dsRNA Transcription Issue | 1 | 2 |
| | Agronomics | 1 | |
| 2018-2019 Arg Field | Agronomics | 0 | 2 |
| | GSS | 0 | |
| | Events remaining | 0 | |
| Commercial | Further analysis of molecular characterization, protein and DvSnf7 dsRNA expression, efficacy and agronomics from multiple field trials | 1 | MON95275 |

Example 3

Cre-excision of the Glyphosate Selection Cassette in Corn Event MON95275

This Example describes the removal of the glyphosate selection cassette from corn event MON95275 through in vivo Cre-excision. The glyphosate selection cassette was used to select transformed events. By removal of the selection cassette, a "marker-free" event was created wherein only the insecticidal protein expression cassettes remained in the final event.

Corn variety LH244 immature embryos were transformed using an *Agrobacterium*-mediated transformation process with Construct pM95275 (presented as SEQ ID NO:13 and illustrated in FIG. 2). Construct pM95275 contains 4 expression cassettes: 2 expression cassettes for the expression of the insecticidal proteins Cry75Aa1 and Vip4Da2, 1 expression cassette for the expression of the DvSnf7 dsRNA, and a single cassette used for the selection of transformed plant cells using glyphosate selection. The selection cassette was flanked on both sides with Cre-recombinase LoxP recognition sequences.

After transformation, the $R_0$ transformants were self-pollinated for 2 generations, during which time many events were removed based upon various assays such as efficacy, DvSnf7 expression, protein expression, seed return and plant health, and molecular characterization. By the $R_2$ generation, 19 events remained from the initial 140 events. The 19 homozygous $R_2$ generation events were bred with an elite line of transformed corn plants expressing Cre-recombinase enzyme, derived from Enterobacteria phage P1.

Figure 3:
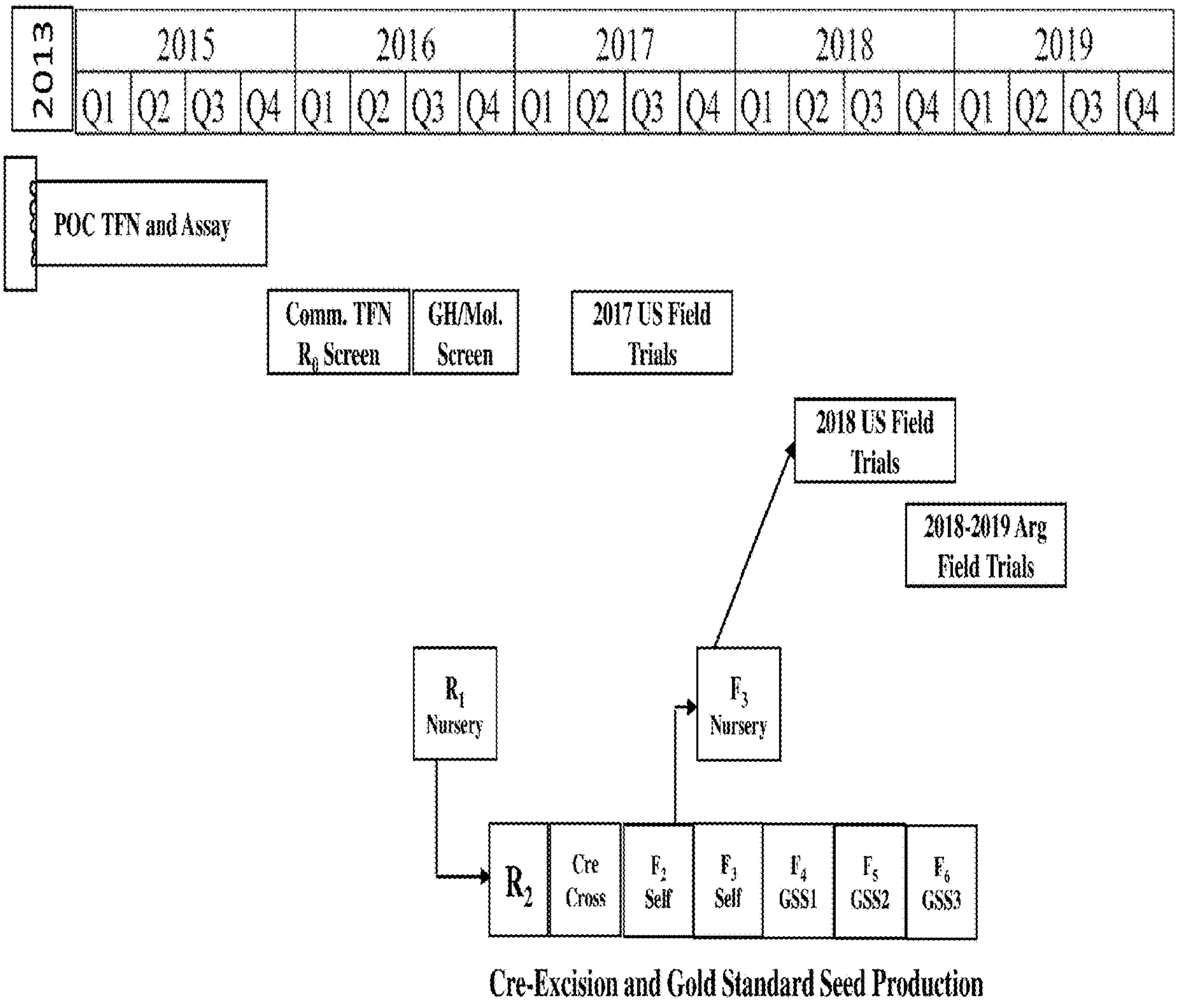
FIG. 3 is a diagrammatic representation of the timeline for the research, testing, and development that was relied upon in order to select the corn event MON95275.

This stage in which $R_2$ generation events were bred with plants expressing Cre-recombinase is identified as "Cre Cross" in the timeline presented in FIG. 3. Specifically, in this stage, de-tasseled (female) $R_2$ generation plants homozygous for SEQ ID NO:13 were cross-pollinated with transgenic corn plants (male) homozygous for a transgene cassette used for expression of Cre-recombinase enzyme. The Cre-recombinase expressing male donor pollen germinates after landing on the silk tissue of the female plant comprising SEQ ID NO:13. Once the pollen tube enters the embryo sac, the pollen tube ruptures, setting free the two sperms of the Cre-recombinase expressing male donor. The nucleus of one sperm fuses with the egg nucleus, forming the zygote. The other sperm nucleus fuses with one of the two polar nuclei which in turn fuses with the other polar nucleus, thereby establishing the primary endosperm nucleus.

Thus, in using the Cre-recombinase expressing plant as the male pollen donor, both the embryo and endosperm of the resulting cross will express Cre-recombinase as the cells divide and develop and become a corn kernel (i.e., seed). The Cre-recombinase binds to inverted repeats in the LoxP site and catalyzes a crossover in an eight-base pair spacer region of the two LoxP sites that flank the expression cassette, resulting in the excision of the marker cassette with one LoxP site remaining in the integrated T-DNA due to recombination (see FIG. 2, "Inserted T-DNA After Cre-Excision").

The $F_1$ progeny resulting from the Cre Cross were selected for the absence of the CP4 selection cassette and allowed to self-pollinate. This stage in which $F_1$ progeny were allowed to self-pollinate is identified as "$F_1$ Self" in the timeline presented in FIG. 3. Through this process, the two alleles—the Cre-recombinase allele and the allele for the T-DNA used to generate event MON95275—segregate in the resulting $F_2$ population, resulting in progeny homozygous or heterozygous for one or both alleles.

The $F_2$ progeny which demonstrated the absence of the Cre-recombinase allele and homozygosity for SEQ ID NO:9, the transgenic inserted T-DNA after Cre-excision, were selected. These selected $F_2$ progeny were self-pollinated, giving rise to an $F_3$ generation homozygous for SEQ ID NO:9. This stage in which $F_2$ progeny were allowed to self-pollinate is identified as "$F_2$ Self" in the timeline presented in FIG. 3.

A further self-pollination resulted in $F_3$ progeny seed ($F_4$ seed) which were assayed for purity and were designated as "Gold Standard Seed." $F_4$ was the first generation of gold standard seed. Gold Standard Seed is seed that has been assayed for purity to assure the absence of events other than MON95275. This stage in which $F_3$ progeny were allowed to self-pollinate is identified as "$F_3$ Self" in the timeline presented in FIG. 3.

Excision of the glyphosate selection marker cassette did not affect the expression of Cry75Aa1, Vip4Da2, and DvSnf7 dsRNA. Removing the glyphosate selection cassette from corn event MON95275 through Cre-excision provided a transgenic corn event which is resistant to Coleopteran pests without adding tolerance to glyphosate in the final event. This "marker-free" event assures flexibility when building corn breeding stacks with other corn transgenic events to provide a multiplicity of products incorporating event MON95275 and allowing multiple options for providing additional traits in the final commercial breeding stacks.

Example 4

Corn Event MON95275 Demonstrates Resistance to the Coleopteran Insect Pests Western Corn Rootworm and Northern Corn Rootworm This Example describes the activity of the corn event MON95275 against Coleopteran insect pests. The insect toxin proteins Cry75Aa1 and Vip4Da2 and the DvSnf7 dsRNA, when expressed together in corn event MON95275, provide resistant to Western Corn Rootworm (*Diabrotica virgifera virgifera*, WCR) and Northern Corn Rootworm (*Diabrotica barberi*, NCR).

MON95275 Demonstrates Resistance to Western Corn Rootworm in the Greenhouse and in the Field After transformation and insertion of Construct pM95275, $R_0$ stage events were transferred to the greenhouse and allowed to self-pollinate and produce seed. Selected $R_1$ seed was planted in pots and grown in the greenhouse. Eggs from Western Corn Rootworm (WCR) were incubated for approximately 10 days to allow hatching within 4 days after inoculation. 6 plants for each event were assayed. The plants were inoculated at approximately V2 to V3 stage. Each pot was inoculated with about 2,000 eggs. The plants were grown after infestation for approximately 28 days. The plants were then removed from the pots and the roots were carefully washed to remove all soil. The damage to the roots of each plant were assessed using a damage rating scale of 0-3, as presented in Table 4. Comparison was made to a negative wild-type control of the same variety as the transformants. A root damage rating (RDR) of 0-0.75 represents good efficacy, an RDR of 0.76-1.5 represents medium efficacy, and an RDR of 1.6-3.0 represents low or poor efficacy.

TABLE 4

$R_1$ root damage rating scores.

| Root Damage Rating (RDR) | Description |
|---|---|
| 0 | No visible feeding |
| 0.01-0.09 | Feeding scars and tracks |
| 0.1-0.9 | Root pruning, but less than a full node |
| 1.0-1.9 | At least a full node (or equivalent) destroyed to within 1.5 inches of plant |
| 2.0-2.9 | Two or more nodes gone |
| 3 | Three or more nodes gone |

As can be seen in Table 5, corn event MON95275 demonstrated significant efficacy when compared to the negative control.

TABLE 5

Average $R_1$ Root Damage (RDR) for corn event MON95275.

| Event | Number of Plants | Average RDR | Std Dev |
|---|---|---|---|
| Wild Type | 6 | 2.33 | 0.23 |
| MON95275 | 6 | 0.05 | 0.00 |

Field efficacy trials were conducted in the United States to assess corn event MON95275 resistance against WCR. Field trials were conducted at 8 separate locations know to have WCR infestations; Colesburg, IA, Fairbank, IA, Independence, IA, Leigh, NE, Pilger, NE, Roanoke, IL, Rowan, IA, and Shelby, NE. Hybrid plants produced by crossing inbred corn event MON95275 (LH244) with corn variety 93IDI3 were grown in the WCR infested fields. Corn event MON95275 still comprised the CP4 marker cassette in this field trial. In addition, two negative controls were also grown; (1) corn hybrid MON89034 (93IDI3)×LH244 which is Lepidopteran resistant, and (2) non-transgenic corn hybrid 93IDI3×LH244.

The trials in each location were planted as a randomized complete block design. The plots were blocked by rep and within that block, plot location was randomized. Both MON95275 and controls were represented once within each block. Block dimensions such as number of columns per row by number of ranges deep varied by location, depending on the size and shape of the field. Each entry was evenly distributed across the field to compensate for any differences in WCR pressure that might occur. Approximately 10 plants each for MON95275 and the controls were dug up at around VT stage. The roots were carefully washed and a Root Damage Ratings (RDR) from 0.1-3.00 was assigned to each plant and is presented in Table 6.

TABLE 6

Field Root Damage Rating (RDR) scale.

| Economic Damage | Root Damage Rating (RDR) | Description |
|---|---|---|
| Non-economic damage | 0.01 | No visible feeding scars. |
| | 0.05 | visible feeding scars and/or tracks. |
| | 0.08 | Severe feeding scars. |
| | 0.10 | Pruning of 10% of roots on a single node to within 1.5 inches (4 cm) of stalk or soil line. |
| | 0.20 | Pruning of 20% of roots on a single node (or equivalent*) to within 1.5 inches (4 cm) of stalk or soil line. |
| May be economic damage under heat stress and reduced rainfall | 0.30 | Pruning of 30% of roots on a single node (or equivalent*) to within 1.5 inches (4 cm) of stalk or soil line. |
| | 0.40 | Pruning of 40% of roots on a single node (or equivalent*) to within 1.5 inches (4 cm) of stalk or soil line. |
| | 0.50 | Pruning of 50% of roots on a single node (or equivalent*) to within 1.5 inches (4 cm) of stalk or soil line. |
| Probably economic damage under heat stress and reduced rainfall | 0.60 | Pruning of 60% of roots on a single node (or equivalent*) to within 1.5 inches (4 cm) of stalk or soil line. |
| | 0.70 | Pruning of 70% of roots on a single node (or equivalent*) to within 1.5 inches (4 cm) of stalk or soil line. |
| | 0.80 | Pruning of 80% of roots on a single node (or equivalent*) to within 1.5 inches (4 cm) of stalk or soil line. |
| | 0.90 | Pruning of 90% of roots on a single node (or equivalent*) to within 1.5 inches (4 cm) of stalk or soil line. |
| Likely economic unless conditions for root growth are favorable after damage | 1.00 | Pruning of one full node (or equivalent*) to within 1.5 inches (4 cm) of stalk or soil line. |
| | 1.25 | Pruning of one full node plus 25% of another node to within 1.5 inches (4 cm) of stalk or soil line. |
| | 1.50 | Pruning of one full node plus 50% of another node to within 1.5 inches (4 cm) of stalk or soil line. |
| | 1.75 | Pruning of one full node plus 75% of another node to within 1.5 inches (4 cm) of stalk. |
| Economic damage | 2.00 | Pruning of two full nodes to within 1.5 inches (4 cm) of stalk or soil line. |
| | 2.25 | Pruning of two full nodes plus 25% of another node to within 1.5 inches (4 cm) of stalk or soil line. |
| Severe damage, lodging and goose-necking are common | 2.50 | Pruning of two full nodes plus 50% of another node to within 1.5 inches (4 cm) of stalk or soil line. |
| | 2.75 | Pruning of two full nodes plus 75% of another node to within 1.5 inches (4 cm) of stalk or soil line. |

TABLE 6-continued

Field Root Damage Rating (RDR) scale.

| Economic Damage | Root Damage Rating (RDR) | Description |
|---|---|---|
| Devastating damage, lodging and goose-necking are almost certain | 3.00 | Pruning of three full nodes to within 1.5 inches (4 cm) of stalk or soil line. |

*For example, if two nodes show 20% and 30% root pruning, the root would be scored as having a root damage rating of 0.50, or if one node shows 10% and two other nodes show 10% each, the root would be scored as having a root damage rating of 0.30, or if two nodes are each missing 50% of their roots, the root would be scored as having a root damage rating of 1.00, etc.

Tables 7 and 8 show the average Root Damage Ratings for corn event MON95275 and the two negative controls corresponding to each field location.

TABLE 7

Average WCR Root Damage Ratings for MON95275 and controls from Colesburg, IA, Fairbank, IA, Independence, IA, and Leigh, NE

| | Colesburg | | | Fairbank | | | Independence | | | Leigh | | |
|---|---|---|---|---|---|---|---|---|---|---|---|---|
| Event | Plots | N | RDR | Plots | N | RDR | Plots | N | RDR | Plots | N | RDR |
| 93IDI3 × LH244 | 3 | 29 | 1.79 | 3 | 28 | 1.75 | 3 | 30 | 0.98 | 3 | 28 | 1.48 |
| MON 89034(93IDI3) × LH244 | 6 | 60 | 2.05 | 6 | 54 | 2.15 | 6 | 55 | 1.05 | 6 | 56 | 1.20 |
| MON95275(LH244) × 93IDI3 Marker | 3 | 27 | 0.08 | 3 | 28 | 0.06 | 3 | 30 | 0.10 | 3 | 29 | 0.08 |

TABLE 8

Average WCR Root Damage Ratings for MON95275 and controls from Pilger, NE, Roanoke, IL, Rowan, IA, and Shelby, NE

| | Pilger | | | Roanoke | | | Rowan | | | Shelby | | |
|---|---|---|---|---|---|---|---|---|---|---|---|---|
| Event | Plots | N | RDR | Plots | N | RDR | Plots | N | RDR | Plots | N | RDR |
| 93IDI3 × LH244 | 3 | 30 | 0.88 | 3 | 29 | 0.28 | 3 | 28 | 0.62 | 3 | 30 | 0.61 |
| MON 89034(93IDI3) × LH244 | 6 | 60 | 0.96 | 6 | 58 | 0.53 | 6 | 59 | 0.64 | 6 | 59 | 0.98 |
| MON95275(LH244) × 93IDI3 Marker | 3 | 30 | 0.06 | 3 | 30 | 0.06 | 3 | 30 | 0.10 | 3 | 30 | 0.08 |

As can be seen in Tables 7 and 8, corn event MON95275 provided resistance to WCR when compared to the negative controls. While in most cases the controls experienced damage that could potentially lead to economic losses based upon the RDR scale presented in Table 6, corn event MON95275 demonstrated resistance to WCR and only experienced damage that would be considered non-economic across all locations.

In the summer of 2018 field efficacy trials were conducted in 5 U.S. locations known to have WCR infestations to assess corn event MON95275 resistance to WCR; Dundee, IA, Leigh, NE, Oneida, IA, Pilger, NE, and Kingsley, IA. Field trials were conducted and Root Damage Ratings were performed as described above. Both marker-positive and marker-free corn event MON95275 were assayed along with the two negative controls previously described. Tables 9 and 10 show the average Root Damage Ratings for marker and marker-free corn event MON95275 and the two negative controls corresponding to each field location.

TABLE 9

Average WCR Root Damage Ratings for MON95275 and controls from Dundee, IA, Leigh, NE, and Oneida, IA.

| | Dundee | | | Leigh | | | Oneida | | |
|---|---|---|---|---|---|---|---|---|---|
| Event | Plots | N | RDR | Plots | N | RDR | Plots | N | RDR |
| 93IDI3 × LH244 | 3 | 29 | 1.17 | 3 | 25 | 1.86 | 3 | 29 | 1.37 |
| MON 89034(93IDI3) × LH244 | 9 | 86 | 1.20 | 8 | 74 | 1.87 | 9 | 86 | 1.51 |
| MON95275(LH244) × 93IDI3 Marker | 3 | 30 | 0.06 | 3 | 26 | 0.20 | 3 | 30 | 0.06 |
| MON95275(LH244) × 93IDI3 Marker-Free | 3 | 30 | 0.08 | 3 | 27 | 0.15 | 3 | 29 | 0.11 |

TABLE 10

Average WCR Root Damage Ratings for MON95275 and controls from Pilger, NE and Kingsley, IA.

| | Pilger | | | Kingsley | | |
|---|---|---|---|---|---|---|
| Event | Plots | N | RDR | Plots | N | RDR |
| 93IDI3 × LH244 | 3 | 28 | 1.60 | 6 | 56 | 2.12 |
| MON 89034(93IDI3) × LH244 | 9 | 89 | 1.24 | 18 | 172 | 2.17 |
| MON95275(LH244) × 93IDI3 Marker | 3 | 22 | 0.59 | 6 | 60 | 0.07 |
| MON95275(LH244) × 93IDI3 Marker-Free | 3 | 23 | 0.96 | 3 | 30 | 0.07 |

As can be seen in Tables 9 and 10, both marker-positive and marker-free corn event MON 95275 demonstrated resistance to WCR relative to the negative controls. In all but one location, damage to the marker and marker-free corn event MON95275 was non-economic. Damage in Pilger, NE was higher, but still much lower than damage to the negative controls at that location.

Corn event MON95275 provides resistance to Wester Corn Rootworm (*Diabrotica virgifera virgifera*) as demonstrated in the greenhouse and two U.S. field trials.

MON95275 Provides Resistance to Northern Corn Rootworm in the Field

In the summer of 2017, a single field trial was conducted in Hawkeye, IA, in a field known to be infested with Northern Corn Rootworm (NCR). Marker-positive hybrid corn event MON95275 and the two negative controls as described above were grown on multiple plots in the field in a similar manner as that performed for Western Corn Rootworm. Root Damage Rating were assessed for event MON95275 and the two negative controls using the same scale as that presented in Table 6. Table 11 shows the Average Root Damage Ratings and RDR ranges for the marker-positive corn event MON95275 and the negative controls.

TABLE 11

Average NCR Root Damage Ratings for MON95275 and controls from Hawkeye, IA.

| | Hawkeye | | | |
|---|---|---|---|---|
| Event | Plots | N | Range | RDR |
| 93IDI3 × LH244 | 4 | 38 | 0.09-0.57 | 0.14 |
| MON89034(93IDI3) × LH244 | 8 | 77 | 0.34-0.98 | 0.51 |
| MON95275(LH244) × 93IDI3 Marker | 4 | 38 | 0.05-0.7 | 0.07 |

As can be seen in Table 11 above, the average RDR for marker-positive MON95275 was lower than the MON89034 (93IDI3)×LH244 negative control. The average RDR was low for the non-transgenic control, suggesting NCR pressure was low in the field.

In the summer of 2018, field trials were conducted in three (3) separate locations known to be infested with NCR, Belmond, IA, Benson, MN, and Colton, SD. Field trials were conducted as previously described. Tables 12 and 13 show the average RDR and RDR range for the three (3) locations.

TABLE 12

Average NCR Root Damage Ratings for MON95275 and controls from Belmond, IA and Benson, MN.

| | Belmond | | | | Benson | | | |
|---|---|---|---|---|---|---|---|---|
| Event | Plots | N | Range | RDR | Plots | N | Range | RDR |
| 93IDI3 × LH244 | 4 | 40 | 0.13-0.96 | 0.37 | 4 | 39 | 1.30-2.78 | 2.04 |
| MON89034(93IDI3) × LH244 | 10 | 99 | 0.15-1.26 | 0.50 | 10 | 95 | 1.20-2.28 | 1.98 |
| MON95275(LH244) × 93IDI3 Marker | 4 | 38 | 0.06-0.08 | 0.07 | 4 | 35 | 0.07-0.17 | 0.10 |

TABLE 13

Average NCR Root Damage Ratings for MON95275 and controls from Colton, SD.

| | Colton | | | |
|---|---|---|---|---|
| Event | Plots | N | Range | RDR |
| 93IDI3 × LH244 | 4 | 40 | 0.16-1.33 | 0.69 |
| MON89034(93IDI3) × LH244 | 10 | 88 | 0.17-2.45 | 1.29 |
| MON95275(LH244) × 93IDI3 Marker | 4 | 39 | 0.09-0.21 | 0.14 |

As can be seen in Tables 12 and 13, corn event MON95275 provided resistance to NCR. For example, in Benson, MN, NCR pressure was high as can be seen in the high average RDRs of the negative controls, but the average RDR was below economic damage in corn event MON95275. In all three (3) locations, MON95275 demonstrated resistance to NCR relative to the two negative controls.

MON95275 provides resistance to Northern Corn Rootworm (*Diabrotica barberi*).

Example 5

Corn Event MON95275 Provides Consistent Yield and Similar Agronomics to Untransformed LH244 Corn Plants This Example demonstrates that transgenic corn event MON95275 provides consistent yields and similar agronomics in the field to untransformed LH244 corn plants.

Field trials were conducted with plants corresponding to MON95275 prior to Cre-excision of the glyphosate selection cassette and after Cre-excision to determine various aspects of yield and agronomics in comparison to control plants. Measurements of yield were calculated and expressed as bushels per acre (bu/acre). Plant height and ear height were measured in inches (in). 50% pollen shed and 50% silking were expressed as days after planting (DAP).

In the growing season of 2017 in the United States, yield and agronomic measures were determined for MON95275 inbreds and hybrids pre-Cre-excision of the glyphosate maker cassette. Tables 14 and 15 show the yield and agronomic characteristics measured for MON95275 inbreds and hybrids, respectively. The negative control plants for the inbred comparisons was untransformed variety LH244. Hybrids containing MON95275 were created by cross pollinating the inbred MON95275 with corn variety 93IDI3, and the control was a MON 89034 (93IDI3)×LH244 cross.

TABLE 14

Yield and agronomics for MON95275 inbreds relative to non-transgenic controls.

| Event | Yield (bu/acre) | Plant Height (in) | Ear Height (in) | 50% Pollen Shed (DAP) | 50% Silking (DAP) |
|---|---|---|---|---|---|
| MON95275(LH244) marker | 104.3 | 79 | 35.9 | 60.8 | 62.1 |
| LH244 | 110.7 | 80.6 | 36.6 | 60.6 | 61.5 |

TABLE 15

Yield and agronomic for MON95275 hybrids relative to non-transgenic controls.

| Event | Yield (bu/acre) | Plant Height (in) | Ear Height (in) | 50% Pollen Shed (DAP) | 50% Silking (DAP) |
|---|---|---|---|---|---|
| MON95275(LH244) × 93IDI3 Marker | 223.2 | 101.3 | 44.6 | 55.8 | 56.1 |
| MON 89034(93IDI3) × LH244 | 216.7 | 98.8 | 46.3 | 54.9 | 55.2 |

As can be seen in Tables 15 and 16, the yield and other agronomic measures for MON95275 in the 2017 United States field trials were relatively the same for both inbreds and hybrids relative to the controls. The variability between the inbreds and hybrids and their respective controls was within acceptable limits and demonstrate there were no negative impacts on yield and other agronomic characteristics caused by insertion of the T-DNA into the corn genome of event MON95275.

In the growing season of 2018 in the United States, yield and agronomic measures were determined for MON95275 inbreds and hybrids pre-Cre-excision and post-Cre-excision of the glyphosate maker cassette. Tables 16 and 17 show the yield and agronomic characteristics measured for MON95275 marker-positive and marker-free inbreds and hybrids, respectively.

TABLE 16

Yield and agronomics for MON95275 inbreds relative to non-transgenic controls.

| Event | Yield (bu/acre) | Plant Height (in) | Ear Height (in) | 50% Pollen Shed (DAP) | 50% Silking (DAP) |
|---|---|---|---|---|---|
| MON95275(LH244) Marker | 114.3 | 83.1 | 37.7 | 62.0 | 63.1 |
| LH244 | 122.4 | 82.7 | 38.6 | 62.0 | 63.1 |
| MON95275(LH244) Marker-free | 139.0 | 84.0 | 36.5 | 61.8 | 63.0 |
| LH244 | 128.1 | 84.5 | 38.6 | 61.8 | 62.8 |

TABLE 17

Yield and agronomics for MON95275 hybrids relative to non-transgenic controls.

| Event | Yield (bu/acre) | Plant Height (in) | Ear Height (in) | 50% Pollen Shed (DAP) | 50% Silking (DAP) |
|---|---|---|---|---|---|
| MON95275(LH244) × 93IDI3 Marker | 208.1 | 99.5 | 45.5 | 57.7 | 58.9 |
| MON89034(93IDI3) × LH244 | 201.4 | 98.5 | 44.6 | 57.5 | 58.9 |
| MON95275(LH244) × 93IDI3 Marker-free | 212.6 | 100.6 | 46.9 | 57.8 | 59.0 |
| MON89034(93IDI3) × LH244 | 221.5 | 99.3 | 44.9 | 58.1 | 59.2 |

As can be seen in Tables 16 and 17, the yield and other agronomic measures for MON95275, both marker-positive and marker-free, in the 2018 United States field trials were relatively the same for both inbreds and hybrids relative to the controls. The variability between the inbreds and hybrids and their respective controls was within acceptable limits and demonstrate there were no negative impacts on yield and other agronomic characteristics caused by insertion of the T-DNA into the corn genome of event MON95275.

Yield and agronomics were also studied in Argentina during the 2018 to 2019 growing season for MON95275 marker-free inbreds. Table 18 shows the yield and agronomic characteristics measured for MON95275 marker-free inbreds.

TABLE 18

Yield and agronomics for MON95275 inbreds relative to non-transgenic controls.

| Event | Yield (bu/acre) | Plant Height (in) | Ear Height (in) | 50% Pollen Shed (DAP) | 50% Silking (DAP) |
|---|---|---|---|---|---|
| MON95275(LH244) Marker-free | 101.6 | 74.4 | 37.5 | 70.5 | 70 |
| LH244 | 105.2 | 73.5 | 34.3 | 70.3 | 69.8 |

As can be seen in Table 18, the yield and other agronomic measures were relatively the same for marker-free inbreds and controls from the 2018-2019 Argentina field trials. The variability between the inbreds and the control was within acceptable limits and demonstrate there were no negative impacts on yield and other agronomic characteristics caused by insertion of the T-DNA into the corn genome of event MON95275.

Example 6

Corn Event MON95275 Event-Specific Endpoint TAQMAN® Assays

The following Example describes methods useful in identifying the presence of MON95275 in a corn sample. A pair of PCR primers and a probe were designed for the purpose of identifying the unique junction formed between the corn genomic DNA and the inserted DNA of MON95275 in an event-specific endpoint TAQMAN® PCR. Examples of conditions utilized for identifying the presence of MON95275 in a corn sample in an event-specific endpoint TAQMAN® PCR are described in Table 19 and Table 20.

The sequence of the oligonucleotide forward primer SQ20267 (SEQ ID NO: 15) is identical to the nucleotide sequence corresponding to positions 15,706-15,732 of SEQ ID NO: 10. The sequence of the oligonucleotide reverse primer SQ51355 (SEQ ID NO:16) is identical to the reverse complement of the nucleotide sequence corresponding to positions 15,756-15,779 of SEQ ID NO: 10. The sequence of the oligonucleotide probe PB10263 (SEQ ID NO:17) is identical to the nucleotide sequence corresponding to positions 15,734-15,752 of SEQ ID NO:10. The primers SQ20267 (SEQ ID NO:15) and SQ51355 (SEQ ID NO:16) with probe PB 10263 (SEQ ID NO:17), which may be fluorescently labeled (e.g., a 6-FAM™ fluorescent label), can be used in an endpoint TAQMAN® PCR assay to identify the presence of DNA derived from MON95275 in a sample.

In addition to SQ20267 (SEQ ID NO:15), SQ51355 (SEQ ID NO:16), and PB 10263 (SEQ ID NO: 17), it should be apparent to persons skilled in the art that other primers and/or probes can be designed to either amplify or hybridize to sequences within SEQ ID NO:10 which are unique to, and useful for, detecting the presence of DNA derived from MON95275 in a sample.

Following standard molecular biology laboratory practices, PCR assays for event identification were developed for detection of MON95275 in a sample. Parameters of either a standard PCR assay or a TAQMAN® PCR assay were optimized with each set of primer pairs and probes (e.g., probes labeled with a fluorescent tag such as 6-FAM™) used to detect the presence of DNA derived from MON95275 in a sample. A control for the PCR reaction includes internal control primers and an internal control probe (e.g., VIC®-labeled) specific to a region within the corn genome that is used as an internal control, and are primers SQ20222 (SEQ ID NO:18), SQ20221 (SEQ ID NO:19), and VIC® labeled probe PB50298 (SEQ ID NO:20).

Generally, the parameters which were optimized for detection of MON95275 in a sample included primer and probe concentration, amount of templated DNA, and PCR amplification cycling parameters. The controls for this analysis include a positive control from corn containing MON95275. a negative control from non-transgenic corn, and a negative control that contains no template DNA.

TABLE 19

MON95275 event-specific endpoint TAQMAN ® PCR reaction components.

| Step | Reagent | Stock Concentration (μM) | Volume (μl) | Final Concentration (μM) | Comments |
|---|---|---|---|---|---|
| | Reaction volume | | 5 | | |
| 1 | Master Mix | | 2.28 | | 1× final concentration |
| 2 | Event Specific Primer SQ51355 | 100 | 0.05 | 0.9 | |
| 3 | Event Specific Primer SQ20267 | 100 | 0.05 | 0.9 | |
| 4 | Event Specific 6FAM ™ probe PB10263 | 100 | 0.01 | 0.2 | Probe is light sensitive |
| 5 | Internal Control Primer SQ20222 | 100 | 0.05 | 0.9 | |
| 6 | Internal Control Primer SQ20221 | 100 | 0.05 | 0.9 | |
| 7 | Internal Control VIC ® probe PB50298 | 100 | 0.01 | 0.2 | Probe is light sensitive |
| 8 | Extracted DNA (template):<br>Leaf Samples to be analyzed<br>Negative control (non-transgenic DNA)<br>Negative water control (No template control)<br>Positive Qualitative control(s) MON95275 DNA | | 2.5 | | Separate reactions are made for each template. |

TABLE 20

| Endpoint TAQMAN ® thermocycler conditions. | | |
|---|---|---|
| Step No. | Number of Cycles | Settings |
| 1 | 1 | 95° C. 20 seconds |
| 2 | 35 | 95° C. 3 seconds<br>60° C. 20 seconds |
| 3 | 1 | 10° C. |

Example 7

Assays for Determining Zygosity for Corn Event MON95275 Using TAQMAN®

The following Example describes methods useful in identifying the zygosity of event MON95275. Pairs of PCR primers and a probe are designed for the purpose of identifying specific properties of alleles positive for the T-DNA insertion that gave rise to event MON95275 and pairs of PCR primers and a probe are designed as an internal control probe specific to a region within the corn genome that is used as an internal control which is represented in the corn genome as homozygous.

The pairs of PCR primers and probe specific to the MON95275 transgenic allele, described in Example 6, PCR primers SQ20267 (SEQ ID NO:15), SQ51355 (SEQ ID NO: 16), and 6-FAM™ labeled probe PB 10263 (SEQ ID NO:17) and the pairs of PCR primers and probe specific to the internal control, primers SQ20222 (SEQ ID NO:18), SQ20221 (SEQ ID NO:19), and VIC® labeled probe PB50298 (SEQ ID NO:20) are used in a real-time PCR reaction such as that described in Example 6.

After amplification, the cycle thresholds (Ct values) are determined for the amplicon corresponding to the MON95275 inserted allele and the single-copy, homozygous internal standard. The difference (ΔCt) between the Ct value of the single-copy, homozygous internal standard amplicon and the Ct value of the MON95275 inserted allele amplicon are determined. With respect to zygosity, a ΔCt of around zero (0) indicates homozygosity of the inserted MON95275 T-DNA and ΔCt of around one (1) indicated heterozygosity of the inserted MON95275 T-DNA. Lack of an amplicon corresponding to the MON95275 inserted allele indicates the sample is null for the inserted MON95275 T-DNA. The Ct values in the TAQMAN® thermal amplification method will have some variability due to multiple factors such as amplification efficiency and ideal annealing temperatures. Therefore, the range of "about one (1)" is defined as a ΔCt of 0.75 to 1.25.

Example 8

Assays for Determining Zygosity for Corn Event MON95275 Using TAQMAN®

The following Example describes a method useful in identifying the zygosity of event MON95275 in a corn sample.

A pair of PCR primers and a probe are designed for the purpose of identifying specific properties of alleles positive and negative for the T-DNA insertion that gave rise to event MON95275. Examples of conditions that may be used in an event-specific zygosity TAQMAN® PCR are provided in Tables 21 and 22. For this assay, four different primers and two different probes are mixed together with the sample. The DNA primer pairs used in the zygosity assay are (1) primers SQ20267 (SEQ ID NO:15) and SQ51355 (SEQ ID NO:16); and (2) primers PNEG95275_F (SEQ ID NO:21) and PNEG95275_R (SEQ ID NO:22). The probes used in the zygosity assay are 6FAM™-labeled probe PB10263 (SEQ ID NO:17) and VIC®-labeled probe PRBNEG95275 (SEQ ID NO:23). Primers SQ20267 (SEQ ID NO:15) and SQ51355 (SEQ ID NO: 16) produce a first amplicon that can be identified by binding to the 6FAM™-labeled probe PB10263 (SEQ ID NO:17), and detecting the binding of the probe to the amplicon is diagnostic for the presence of event MON95275 DNA in a sample containing corn DNA. The primers PNEG95275_F (SEQ ID NO:21) and PNEG95275_R (SEQ ID NO:22) produce a second amplicon that can be identified by binding to the VIC®-labeled probe PRBNEG95275 (SEQ ID NO:23), and detecting the binding of the probe to the amplicon is diagnostic for the absence of the MON95275 event DNA when there is no copy of MON95275 present in a sample containing corn DNA; i.e., this second primer and probe set is diagnostic for the wild type allele.

When the three primers and two probes are mixed together in a PCR reaction with DNA extracted from a plant that is heterozygous for event MON95275, a fluorescent signal is detectable from both the 6FAM™-labeled probe PB10263 (SEQ ID NO:17) and the VIC®-labeled probe PRBNEG95275 (SEQ ID NO:23), and detection of both flurophores from such a thermal amplification reaction is indicative of and diagnostic for a plant heterozygous for event MON95275. When the three primers and two probes are mixed together in a PCR reaction with DNA extracted from a plant that is homozygous for event MON95275, a fluorescent signal is detectable from only the 6FAM™-labeled probe PB10263 (SEQ ID NO:17) and not the VIC®-labeled probe PRBNEG95275 (SEQ ID NO:23). When the three primers and the two probes are mixed together in a PCR reaction with DNA extracted from a plant which is null for MON95275 (i.e., the wild-type), a fluorescent signal is detectable from only the VIC®-labeled probe PRB-NEG95275 (SEQ ID NO:23). The template DNA samples and controls for this analysis are a positive control from corn containing MON95275 DNA (from both a known homozygous and a known heterozygous sample), a negative control from non-transgenic corn and a negative control that contains no template DNA.

TABLE 21

| MON95275 zygosity TAQMAN ® PCR | | | | | |
|---|---|---|---|---|---|
| Step | Reagent | Stock Concentration (μl) | Volume (μl) | Final Concentration (μM) | Comments |
| | Reaction volume | | 5 | | |
| 1 | Master Mix | | 2.28 | | 1× final concentration |

TABLE 21-continued

MON95275 zygosity TAQMAN ® PCR

| Step | Reagent | Stock Concentration (μl) | Volume (μl) | Final Concentration (μM) | Comments |
|---|---|---|---|---|---|
| 2 | Event Specific Primer SQ51355 | 100 | 0.05 | 0.9 | |
| 3 | Event Specific Primer SQ20267 | 100 | 0.05 | 0.9 | |
| 4 | Event Specific 6FAM ™ probe PB10263 | 100 | 0.01 | 0.2 | Probe is light sensitive |
| 5 | WT allele Primer PNEG95275_F | 100 | 0.05 | 0.9 | |
| 6 | WT allele Primer PNEG95275_R | 100 | 0.05 | 0.9 | |
| 7 | WT allele VIC ® probe PRBNEG95275 | 100 | 0.01 | 0.2 | Probe is light sensitive |
| 8 | Extracted DNA (template): Leaf Samples to be analyzed Negative control (non-transgenic DNA) Negative water control (No template control) Positive Qualitative control(s) MON95275 DNA | | 2.5 | | Separate reactions are made for each template. |

TABLE 29

Zygosity TAQMAN ® thermocycler conditions

| Step No. | Number of Cycles | Settings |
|---|---|---|
| 1 | 1 | 95° C. 20 seconds |
| 2 | 40 | 95° C. 3 seconds<br>60° C. 20 seconds |
| 3 | 1 | 10° C. |

Example 9

Identification of Corn Event MON95275 in Any MON95275 Breeding Event

The following Example describes how one may identify the MON95275 event DNA within progeny of any breeding activity using corn event MON95275. For example, the MON95275 event could be stacked by breeding or by site directed introgression with other events known in the art to control corn rootworm pests such as any of the following corn events including but not limited to MON863, MON88017, DAS-59122-7, DP-004114-3, DP23211 and MIR604, The MON95275 event could also be stacked by breeding or by site directed introgression with other transgenic corn events known in the art to control pests other than corn rootworms, such as events including but not limited to include MON810, TC1507, MON89034, MON95379, and MIR162 among those that confer Lepidopteran resistance, or to events that are providing expression of proteins conferring tolerance to any number of herbicides that are known in the art.

DNA primer pairs are used to produce an amplicon diagnostic for corn event MON95275. An amplicon diagnostic for event MON95275 DNA comprises at least one junction sequence. The junction sequences for event MON95275 specific DNA are SEQ ID NO:1, SEQ ID NO:2, SEQ ID NO: 3, SEQ ID NO:4, SEQ ID NO:5, and SEQ ID NO:6 ([1], [2], [3], [4], [5], and [6], respectively in FIG. 1). SEQ ID NO:1 is a fifty (50) nucleotide sequence representing the 5' junction regions of corn genomic DNA and the integrated transgenic expression cassette. SEQ ID NO: 1 is positioned in SEQ ID NO:10 at nucleotide position 1,049-1,098. SEQ ID NO:2 is a fifty (50) nucleotide sequence representing the 3' junction regions of corn genomic DNA and the integrated transgenic expression cassette. SEQ ID NO:2 is positioned in SEQ ID NO:10 at nucleotide position 15,731-15,780. SEQ ID NO:3 is a one hundred (100) nucleotide sequence representing the 5' junction regions of corn genomic DNA and the integrated transgenic expression cassette. SEQ ID NO:3 is positioned in SEQ ID NO:10 at nucleotide position 1,024-1,123. SEQ ID NO: 4 is a one hundred (100) nucleotide sequence representing the 3' junction regions of corn genomic DNA and the integrated transgenic expression cassette. SEQ ID NO:4 is positioned in SEQ ID NO:10 at nucleotide position 15,706-15,805. SEQ ID NO:5 is a two hundred (200) nucleotide sequence representing the 5' junction regions of corn genomic DNA and the integrated transgenic expression cassette. SEQ ID NO:5 is positioned in SEQ ID NO:10 at nucleotide position 974-1,173. SEQ ID NO:6 is a two hundred (200) nucleotide sequence representing the 3' junction regions of corn genomic DNA and the integrated transgenic expression cassette. SEQ ID NO: 6 is positioned in SEQ ID NO: 10 at nucleotide position 15,656-15,855.

Primer pairs that will produce an amplicon diagnostic for event MON95275 include primer pairs based upon the flanking sequences (SEQ ID NO: 11 and SEQ ID NO: 12) and the inserted T-DNA (SEQ ID NO:9). To acquire a diagnostic amplicon in which SEQ ID NO:1, or SEQ ID NO: 3, or SEQ ID NO:5 is found, one would design a forward primer molecule based upon the 5' flanking corn genomic DNA (SEQ ID NO:11) from bases 1-1,073 and a reverse primer molecule based upon the inserted T-DNA (SEQ ID NO:9) from positions 1,074 through 15,755 in which the primer molecules are of sufficient length of contiguous nucleotides to specifically hybridize to SEQ ID NO:11 and SEQ ID NO:9. To acquire a diagnostic amplicon in which SEQ ID NO:2, or SEQ ID NO:4, or SEQ ID NO:6 is found, one would design a forward primer molecule based upon the inserted T-DNA (SEQ ID NO:9) from positions 1,074 through 15,755 and a reverse primer molecule based upon the 3' flanking corn genomic DNA (SEQ ID NO:12) from positions 15,756 through 16,861 in which the primer molecules are of sufficient length of contiguous nucleotides to specifically hybridize to SEQ ID NO:9 and SEQ ID NO:12.

For practical purposes, one should design primers which produce amplicons of a limited size range, preferably between 200 to 1000 bases. Smaller sized amplicons in general are more reliably produced in thermal amplification reactions, allow for shorter cycle times, and can be easily separated and visualized on agarose or acrylamide gels or adapted for use in endpoint TAQMAN®-like assays. In addition, amplicons produced using said primer pairs can be cloned into vectors, propagated, isolated and sequenced, or can be sequenced directly with methods well established in the art. Any primer pair derived from the combinations of SEQ ID NO:11 and SEQ ID NO: 9 or SEQ ID NO:12 and SEQ ID NO:9 that are useful in a DNA amplification method to produce an amplicon diagnostic for event MON95275 DNA or progeny thereof is an aspect of the present invention. Any single isolated DNA polynucleotide primer molecule comprising at least eleven (11) contiguous nucleotides of SEQ ID NO: 11, SEQ ID NO:9 or SEQ ID NO:12 or their complements that is useful in a DNA amplification method to produce an amplicon diagnostic for event MON95275 DNA or progeny containing such DNA thereof is an aspect of the present invention.

An example of the amplification conditions for this analysis is illustrated in Tables 19 and 20. Any modification of these methods or the use of DNA primers homologous or complementary to SEQ ID NO:11 or SEQ ID NO:12, or DNA sequences of the genetic elements contained in the transgene insert (SEQ ID NO:9) of event MON95275 DNA, that produce an amplicon diagnostic for event MON95275 DNA is within the art. A diagnostic amplicon comprises a DNA molecule homologous or complementary to at least one transgene/genomic junction DNA or a substantial portion thereof.

An analysis for a MON95275 event plant tissue sample should include a positive tissue control from a plant that contains event MON95275 DNA, a negative control from a corn plant that does not contain event MON95275 DNA (e.g., LH244), and a negative control that contains no corn genomic DNA. A primer pair will amplify an endogenous corn DNA molecule and will serve as an internal control for the DNA amplification conditions. Additional primer sequences can be selected from SEQ ID NO: 11, SEQ ID NO: 12, or SEQ ID NO: 9 by those skilled in the art of DNA amplification methods. Conditions selected for the production of an amplicon by the methods shown in Table 19 and Table 20 may differ but result in an amplicon diagnostic for event MON95275 DNA. The use of DNA primer sequences within or with modifications to the methods of Table 23 and Table 24 are within the scope of the invention. An amplicon produced by at least one DNA primer sequence derived from SEQ ID NO: 11, SEQ ID NO: 12, or SEQ ID NO:9 that is diagnostic for event MON95275 is an aspect of the invention.

DNA detection kits that contain at least one DNA primer of sufficient length of contiguous nucleotides derived from SEQ ID NO:11, SEQ ID NO: 12, or SEQ ID NO:9 that, when used in a DNA amplification method, produces an amplicon diagnostic for event MON95275 DNA or progeny containing such DNA is an aspect of the invention. A corn plant or seed, wherein its genome will produce an amplicon diagnostic for event MON95275 DNA, when tested in a DNA amplification method is an aspect of the invention. The assay for the MON95275 event amplicon can be performed by using an Applied Biosystems GeneAmp™ PCR System 9700, Stratagene Robocycler®, Eppendorf® Mastercycler® Gradient thermocycler or any other amplification system that can be used to produce an amplicon diagnostic for event MON95275 DNA as shown in Table 24.

All publications and published patent documents cited in this specification, and which are material to the invention, are incorporated herein by reference to the same extent as if each individual publication or patent application was specifically and individually indicated to be incorporated by reference.

Having illustrated and described the principles of the present invention, it should be apparent to persons skilled in the art that the invention can be modified in arrangement and detail without departing from such principles. All modifications that are within the spirit and scope of the appended claims are claimed.

What is claimed is:

1. A method of detecting the presence of a DNA segment diagnostic for corn event MON95275 DNA in a sample, said method comprising:

a) contacting said sample with a DNA probe that comprises the nucleotide sequence of SEQ ID NO:1 or SEQ ID NO:2;

b) subjecting said sample and said DNA probe to stringent hybridization conditions; and c) detecting hybridization of said DNA probe to said DNA segment diagnostic for corn event MON95275 DNA in said sample, wherein said detecting hybridization is diagnostic for the presence of said DNA segment diagnostic for corn event MON95275 DNA in said sample.

2. The method of claim 1, wherein the DNA probe comprises the nucleotide sequence of SEQ ID NO:1.

3. The method of claim 1, wherein the DNA probe comprises the nucleotide sequence of SEQ ID NO:2.

* * * * *

SEQUENCE LISTING

```
Sequence total quantity: 26
SEQ ID NO: 1            moltype = DNA  length = 50
FEATURE                 Location/Qualifiers
source                  1..50
                        mol_type = other DNA
                        note = A 50 nucleotide sequence representing the 5'
                         junction region of corn genomic DNA and the integrated
                         transgenic expression cassette.
                        organism = synthetic construct
SEQUENCE: 1
ttcaggtctg tagcagccgg cccgatcaaa cactgatagt ttcccggtaa            50

SEQ ID NO: 2            moltype = DNA  length = 50
FEATURE                 Location/Qualifiers
source                  1..50
                        mol_type = other DNA
                        note = A 50 nucleotide sequence representing the 3'
                         junction region of the integrated transgenic expression
                         cassette and the corn genomic DNA.
                        organism = synthetic construct
SEQUENCE: 2
```

```
atcatactca ttgctgatcc atgtaactat aacacagagg ctggccaacc            50

SEQ ID NO: 3           moltype = DNA  length = 100
FEATURE                Location/Qualifiers
source                 1..100
                       mol_type = other DNA
                       note = A 100 nucleotide sequence representing the 5'
                        junction region of corn genomic DNA and the integrated
                        transgenic expression cassette.
                       organism = synthetic construct
SEQUENCE: 3
ccgtcccttt tttggcgcat gaagtttcag gtctgtagca gccggcccga tcaaacactg  60
atagtttccc ggtaactata acggtcctaa ggtagcgact                        100

SEQ ID NO: 4           moltype = DNA  length = 100
FEATURE                Location/Qualifiers
source                 1..100
                       mol_type = other DNA
                       note = A 100 nucleotide sequence representing the 3'
                        junction region of the integrated transgenic expression
                        cassette and the corn genomic DNA.
                       organism = synthetic construct
SEQUENCE: 4
ctctttcttt ttctccatat tgaccatcat actcattgct gatccatgta actataacac  60
agaggctggc caacctggag gcgcagcggc gccacaaggt                        100

SEQ ID NO: 5           moltype = DNA  length = 200
FEATURE                Location/Qualifiers
source                 1..200
                       mol_type = other DNA
                       note = A 200 nucleotide sequence representing the 5'
                        junction region of corn genomic DNA and the integrated
                        transgenic expression cassette.
                       organism = synthetic construct
SEQUENCE: 5
gactccaatt ttttatgaag acgggtcaaa actcaacaaa tcaacggata ccgtcccttt  60
tttggcgcat gaagtttcag gtctgtagca gccggcccga tcaaacactg atagtttccc  120
ggtaactata acggtcctaa ggtagcgact taggctgagc ccgggcaggc ctacccataa  180
tacccataat agctgtttgc                                              200

SEQ ID NO: 6           moltype = DNA  length = 200
FEATURE                Location/Qualifiers
source                 1..200
                       mol_type = other DNA
                       note = A 200 nucleotide sequence representing the 3'
                        junction region of the integrated transgenic expression
                        cassette and the corn genomic DNA.
                       organism = synthetic construct
SEQUENCE: 6
ataacgctgc ggacatctac atttttgaat tgaaaaaaaa ttggtaatta ctctttcttt  60
ttctccatat tgaccatcat actcattgct gatccatgta actataacac agaggctggc  120
caacctggag gcgcagcggc gccacaaggt ccagatctcg ttcatcctgg ccacgttgct  180
cgcgactccg aggacgtgca                                              200

SEQ ID NO: 7           moltype = DNA  length = 1226
FEATURE                Location/Qualifiers
source                 1..1226
                       mol_type = other DNA
                       note = A 1,226 nucleotide sequence representing the 5'
                        junction region of corn genomic DNA and the integrated
                        transgenic expression cassette.
                       organism = synthetic construct
SEQUENCE: 7
gaacatttgg cggaagaaca tgttttaagg gctagtttgg aagctcaatt ttcccaagag  60
attcttattt tcccaaggga aaataaacta atttcccttg tgaaaatgaa aatcccttgg  120
aataacgtgg ttcccaaact aaacctaagg gctttttttt atcattgtgt caaacagttt  180
accagctaat tttagtacct taacatttaa ataggtcagc taaaaaagta gctaattgtt  240
agccgaagaa ctgataaatt atttgtccat tagctatttg accttactaa tagatattaa  300
taaatcatat aaatagtcaa gtcttcaaat ataccctgac taatatttgc tagttaatta  360
tttattttct gattaattat tagccactgc taaacaataa gtcagtacga cccaaacaag  420
gcctagttac tactcctatc cataaaaaaa agttgtttga ccattttgac gccaaattta  480
accggcttat attaccaaaa tatttgaaaa aacattaaaa acagttgctg gttaaagtaa  540
attgtatgat aaactaaatc ggaatgaaaa taaataatag ttataatttt ttaataagat  600
gagccagtca aatttgacaa aaagttaaac cgatattctt tctggaacgg aaggagtaga  660
ctgtgttaat gttatgatat tgtgagcaag agagaagggg gtcgatagca acgacccaag  720
tgagtgggag gaggaaggtt ggggcgacga tgttgtgggg agggtgaagg atgatctaaa  780
taatattgtt cgctggattt gagtgagtaa gagcaacccc aacagtttag atataaatcc  840
tagctaaatt tagagtcttg ccaagagatt tttatttttt caaaaaaata gtttattttt  900
ctttgggaaa tagaaatctc ttggaacaat agtgttttta aactagtctt ggcgtttgta  960
```

```
aagaagatag atagactcca attttttatg aagacgggtc aaaactcaac aaatcaacgg  1020
ataccgtccc ttttttggcg catgaagttt caggtctgta gcagccggcc cgatcaaaca  1080
ctgatagttt cccggtaact ataacggtcc taaggtagcg acttaggctg agcccgggca  1140
ggcctaccca taatacccat aatagctgtt tgccaatcgt tcttcttggc gcgccgttgt  1200
caatcaattg gcaagtcata aaatgc                                       1226

SEQ ID NO: 8            moltype = DNA  length = 1207
FEATURE                 Location/Qualifiers
source                  1..1207
                        mol_type = other DNA
                        note = A 1,207 nucleotide sequence representing the 3'
                         junction region of the integrated transgenic expression
                         cassette and the corn genomic DNA.
                        organism = synthetic construct
SEQUENCE: 8
aataacgctg cggacatcta catttttgaa ttgaaaaaaa attggtaatt actctttctt  60
tttctccata ttgaccatca tactcattgc tgatccatgt aactataaca cagaggctgg  120
ccaacctgga ggcgcagcgg cgccacaagg tccagatctc gttcatcctg gccacgttgc  180
tcgcgactcc gaggacgtgc aggccactcg tcgtagctct acctcggcag cctctgtcgc  240
gactccgagg acgtgcaggc cgcgcagctc gcgcgctcct tccgtgccct ctccggtttt  300
gtgattccct gcgccctctc cggcttcgcc gccgcatccg ggtttacgtg gtggtgggcc  360
accgcagtcc caccatccgc gaggcagcca gcagggcccc cgcgctcgac gataggctgc  420
tgaagcccct cgcccatcac cgtcttctgg ggcgtgccta ctgcgaggag gatggggtct  480
tccacaccat gccacaaggt gttcgacgct cgttccaact ccgacgcgca gcctgtctgc  540
tcgcccatca ccggccacct gtctggacgc gcagcctgct gcgtcaacat gctcagcagc  600
atcaactgct caagaagcta caccaacatc actcctcttc ctccacgggg gactggattc  660
gccattggta cctgctgctt catgctcaac caacaccctt cttgccaagg atgatggaga  720
ttatatgaac cggtgtttca gttggtgttg gaagtcccca tggttacatc cagatcagtc  780
ggaatttaga gacttcctcc aatggtcttc ttggcatttc caatttgtca ggtgcagagc  840
atcacagtta ccaattcctt ggccaccacc tataacattg cgtttggtta gagatgacct  900
tgttgtgatg ccagtgattc caagtatgct attgttatct cagtgctatt tcagtggagt  960
agaatgtgtg ctgacaacta tagatccatt attttctaaa ttttgtgctg agagagagct  1020
gttctggaag ccaccttggc aacctccagt tcctaacacc agatctgaga taccgttgtt  1080
gatagagttt gtccatctta ctacaggagt ctgtgatact ctgcatatgg ttactgaatt  1140
tcctaagcaa tactttgttg gcctgcttgt gctgattaca agggaatttt tcatgtctgg  1200
gagaata                                                            1207

SEQ ID NO: 9            moltype = DNA  length = 14682
FEATURE                 Location/Qualifiers
source                  1..14682
                        mol_type = other DNA
                        note = A 14,682 nucleotide sequence corresponding to the
                         transgenic inserted T-DNA of corn event MON95275.
                        organism = synthetic construct
SEQUENCE: 9
tcaaacactg atagtttccc ggtaactata acggtcctaa ggtagcgact taggctgagc  60
ccgggcaggc ctacccataa tacccataat agctgtttgc caatcgttct tcttggcgcg  120
ccgttgtcaa tcaattggca agtcataaaa tgcattaaaa aatattttca tactcaacta  180
caaatccatg agtataacta taattataaa gcaatgatta gaatctgaca aggattctgg  240
aaaattacat aaaggaaagt tcataaatgt ctaaaacaca agaggacata cttgtattca  300
gtaacatttg cagcttttct aggtctgaaa atatatttgt tgcctagtga ataagcataa  360
tggtacaact acaagtgttt tactcctcat attaacttcg gtcattagag gccacgattt  420
gacacatttt tactcaaaac aaaatgtttg catatctctt ataatttcaa attcaacaca  480
caacaaataa gagaaaaaac aaataatatt aatttgagaa tgaacaaaag gaccatatca  540
ttcattaact cttctccatc catttccatt tcacagttcg atagcgaaaa ccgaataaaa  600
aacacagtaa attacaagca caacaaatgg tacaagaaaa acagttttcc caatgccata  660
atactcaaac tcagtaggat tctggtgtgt gcgcaatgaa actgatgcat tgaacttgac  720
gaacgttgtc gaaaccgatg atacgaacga aagctaggcc tcagcgagta ccgctggcga  780
tctaatccat gatatcgtga acatcatcta cattcaaatt cttatgagct ttcttaaggg  840
catctgcagc atttttcata gaatctaata cagcagtatt tgtgctagct ccttcgaggg  900
cttccctctg catttcaata gttgtaaggg ttccatctat ttgtagttgg gtcttttcca  960
atcgtttctt ctttttgagg gcttggagtg caactctttt atttttcgac gcatttttct  1020
ttgcgctcct gcaggcggcc gcgtggatga ggagttaatc ggtcgtgtga gagtagtgat  1080
cgagtggatg tcgtcgagag tgatgagtgt tgatgttgtt agtgatatgt ggtagaaggt  1140
atcgtgataa agcgttaacg cgatcgcagt acttgcaaag aaaaatgcgt cgaaaaataa  1200
aagagttgca ctccaagccc tcaaaaagaa gaaacgattg gaaaagaccc aactacaaat  1260
agatggaacc cttacaacta ttgaaatgca gagggaagcc ctcgaaggag ctagcacaaa  1320
tactgctgta ttagattcta tgaaaaatgc tgcagatgcc cttaagaaag ctcataagaa  1380
tttgaatgta gatgatgttc acgatatcat ggatggtatc gcacagcgac tgctgaggga  1440
cgtcgagctc ccgcttggta tctgcattac aatgaaatga gcaaagacta tgtgagtaac  1500
actggtcaac actagggaga aggcatcgag caagatacgt atgtaaagag aagcaatata  1560
gtgtcagttg gtagatacta gataccatca ggaggtaagg agagcaacaa aaaggaaact  1620
ctttattttt aaattttgtt acaacaaaca agcagatcaa tgcatcaaaa tactgtcagt  1680
acttatttct tcagacaaca atatttaaaa caagtgcatc tgatcttgac ttatggtcac  1740
aataaaggag cagagataaa catcaaaatt tcgtcattta tatttattcc ttcaggcgtt  1800
aacaatttaa cagcacacaa acaaaaacag aataggaata tctaattttg gcaaataata  1860
agctctgcag acgaacaaat tattatagta tcgcctataa tatgaatccc tatactattg  1920
acccatgtag tatgaagcct gtgcctaaat taacagcaaa cttctgaatc caagtgccct  1980
ataacaccaa catgtgctta aataaatacc gctaagcacc aaattacaca tttctcgtat  2040
```

```
tgctgtgtag gttctatctt cgtttcgtac taccatgtcc ctatattttg ctgctacaaa  2100
ggacggcaag taatcagcac aggcagaaca cgatttcaga gtgtaattct agatccagct  2160
aaaccactct cagcaatcac cacacaagag agcattcaga gaaacgtggc agtaacaaag  2220
gcagagggcg gagtgagcgc gtaccgaaga cggtcgtacg gaaaatagag agagatagat  2280
ttgtagagag agactggtga tttcagcgtg tcctctccaa atgaaatgaa cttccttata  2340
tagaggaaga gtcttgcgaa ggatagtggg attgtgcgtc atcccttacg tcagtggaga  2400
tatcacatca atccacttgc tttgaagacg tggttggaac gtcttctttt tccacgatgc  2460
tcctcgtggg tgggggtcca tctttgggac cactgtcggc agaggcatct tgaacgatag  2520
cctttccttt atcgcaatga tggactttgt aggagccacc ttccttttct actgtccttt  2580
ccatgaagtg acagatagat gggcaatgga atccgaggag gtttcctgat attacccttt  2640
gttgaaaagt ctcaatagcc ctttggtctt ctgagactgt atctttgata ttcttggagt  2700
agacgagagt gtcgtgctcc accatgttga cgaagatttt cttcttgtca ttgagtcgta  2760
aaagactctg tatgaactgt ccgccagtct tcacggcgag ttctgttaga tcctcgatct  2820
gaatttttga ctccttgctg atggacggtg tggagggagg tgctttcgtg cttggcggca  2880
tgcacgggta atcggcaacg catgtgtgct ttgagcgttg cctggttgtc atgggataca  2940
ggacaacaac catcgtcatg tggagatcga tcgagatata ggatcggagc aagttgacaa  3000
atcatgtcaa aatcactcaa cgaggtagca tgttgtataa acagatcaat gcagaaatac  3060
attagtgcta gctggaattg ttccgatcag ctggcgctat tattatttta tcgaaactga  3120
tgcgtgtgcg tgctcgcctt attttgtgtt ctgcgggggc ggctcccgcg aatacctatt  3180
atttctgtga gcgctcccctt caaaagtgac atgattttat atatccctct acgatacgac  3240
gaccagatca agctaccact accaccgaaa tcaggacctc tgctaaccgg tggcccagac  3300
cggacaaaag ttattgcatt gtatatgggt agggtttatg tccattttac atcgcgcata  3360
gtacgcacaa tttctgttgg cccatcaata tataccgagt gtgctgcagc ctatagtgat  3420
agagttttac ttaattctaa gcctaggatc cgaacagtga ttggaaatcc ttagttacag  3480
tctgacagta taaaggtcac tctcactacc tggtagtaga gccatgaccc ggtgctgata  3540
tcactatcag gtacagccat aaccacagtg ctagtggaaa tatcactacg tactaggcca  3600
atctataatc tgatgagaac acatatagtt gacatagtcg atacgtaccc atgttatgag  3660
tcccgagtga ctgtcaagga catgatttga gttttggtaa gtgtgtgttg gacaaatcga  3720
agcatgagta gggttcatgg cctgtgattt gtactagtct aactaactaa attatcgtgt  3780
acaaccgttg atctgagagg gtcccgcgct gcaaatctat tgtaatactc cctgtcgtaa  3840
tactgtgtta atttgtgctc agtcggacgg ctcagacttt acggtgatat aaacctttac  3900
tgagctgaac tcgacctgga gatcgaatcg accccgcagg tgttccgaag cgtaccacgg  3960
cgagcgttag gtctaagcaa aagccacacc cttcacagaa cgaaggagtt tcgcgaagtc  4020
acgctgattt aaaaagagcg ggccactttt tccactcttg gtcaacagaa aaaggcggac  4080
gagttcagat ttaaggccag ctgcacgccg atcagcagat tcgacgttac ccgcggagag  4140
aaggctgcct gctacttccc agtcgaaagt ggtgtagttc aagtgatctc taaagctaag  4200
gctccgctgg tcctagtcgt taattaccga gcagctctcc ggcgtacaga accacgaagt  4260
tacttcttga ggtgaagcgt aagtggtggt gagggtaagt agttggaagc agaagcctta  4320
agtgatacaa tctggcttcc accttgtcgg aactcgttaa aatttccctt gattacaata  4380
taagtacctg cctgatcgtt ctggtagcct gatcgatttt tatttttggg ctacgggcaa  4440
ttgctcgcaa tttattgaag tcgcacgggc gcgaaagaag acgttgttct ctctgcttgc  4500
tagaagccgc ggataagcga ttctatccga tatttaagac ccgtgtagac cagcagacgt  4560
gagtgggccg tttccagaaa ccgtctctcc ttgcgacgat agatccgata gtaagtaact  4620
tcacccctga tcaacggcgt agtcgcctgt ctggttcgga tctgtataga tttggcggat  4680
tccgcttgcg aaatctttag cagcttaggt ccggagcccc cggtggatct ggctgttcag  4740
cggcacggtc caatctcctt agctcctctg tgaacagcag tcgaactcta agattcttga  4800
tacgcgcaac acgggccttg gcgagcctgg ggataactcg cgaggacgct ctcgccgcgc  4860
taaagcgtgc gatcacaccg ctccgacaag tgactttgcc aaatctagaa agagagacta  4920
cactgcttgc cggtgcagtc ttgatccacc ttggaggggc tgacgctaac taactaaggc  4980
gcgcctgcct actaggcctc gacccttgtt cgtcactgct gacgtctttt tctccattat  5040
tggaggatga gtcactgcaa gctgtaaagc ttgtattatt gctagtggag gccccacctg  5100
cacatgccga gcaattatga ttgtcggcca gtagcttttt gagctgtttg cagagcaata  5160
acttagtgga tgtccccacc attacatcgt tattgatgat gctttcttca aaggaagata  5220
agatgctgac atcctgtctg gagattgtcg ctccatagtg actcgtgatc aatactcttt  5280
catgtgagta attgattttt atctttgttt ctccgttgat ggcctactag gccaaatgga  5340
tgaaacaact tggaccaatc agagatggcc acgtcagctc ccgatcgtcg taaccgacca  5400
aacccgatcg ataacggttt aggctccaat acaccgtcgg taccacccgg tcgctatcat  5460
ctgccccccgt cccaacgcta ttggtatcgt ccgcccctat atcggtcggt agcccagtcc  5520
accgtcgggg ccaatcgtcc cctgctgcgt ccgctcgtgt cggtaccgat cgccaaaaac  5580
gccacgtcaa cggcactgcg gtaccgaccg ccgctggcac cggccttagc gggccacacg  5640
accgatcgct gttgtacgga cgtagaggtg aatcatgcga ttgaattttc gctagaggaa  5700
agttatcatc ttattatctc caaccctcct tcctacggct ggatccgacg aaaatttacc  5760
ctggacggtg ccagtaacaa ttgcaggtct cactcacgtg ctaaatccag caatcaaaca  5820
cgaaggaata tacgtgatct ggccagaaca tgcaagagaa taatacagta gtgttagagt  5880
acgaaaccta cacgattcaa cgaattaatc aatgggttca cgttcacggg tatgctcgcg  5940
cacgtccaaa atccaacgac atttttataa gcggcatgat ccagacgggc cagctcgagc  6000
accacatggc gtggctccat ctcgcatccc ccatcaccgc tataaatacc attggccatg  6060
cacacccgca ctcccacaca gcacaagcag cagcagcagc agcagctcga tcgaactagc  6120
ttagctacta cgtgcgcgtg caacaagcag ctcgatcgat cgccctcacg gtaatttctt  6180
ctcccaaaat aaacctaatc tttaatctgt tgcctgtcta ctcttcctat ctgttgctaa  6240
aaatttgaat ttggtatgtg caggaggact taattaaggg acccaccgcc atgtcatcca  6300
cggacgtgca agagcgcctg cgggacttgg cgcgcgaaga cgaggcggga acgttcaacg  6360
aggcttggaa caccaacttc aagccgtcgg acgagcagca attcagctac tcgccgacgg  6420
agggaattgt cttcctcacg ccgcctaaga acgtcatcgg tgagcggcgc atctcccagt  6480
acaaggtgaa caatgcctgg gcaactctgg agggctctcc caccgaggcg agcggtacgc  6540
cgttgtacgc gggcaagaat gtactggaca actcgaaagg cacaatggac caggagttgc  6600
ttacacccga gttcaactac acctacacgg agagcacgag caacacgacg acgcacggcc  6660
tcaaactcgg cgtgaagacc accgcgacca tgaagttccc tatcgctcaa ggctcgatgg  6720
aggcgagcac cgagtacaat ttccagaact cctccaccga taccaagacc aaacaagtgt  6780
```

```
cttacaagtc tccgagccag aagattaagg ttcctgcggg caagacgtac cgcgtgctgg  6840
cgtacctgaa caccggctct atctctggcg aggctaacct gtacgcgaac gtcggcggca  6900
tcgcgtggcg ggtctcgcca ggctatccta acggcggcgg cgtgaacatc ggcgctgtcc  6960
tgaccaagtg ccagcagaag ggttggggcg acttccgcaa cttccagccc tccgggcgcg  7020
acgtcatcgt gaagggtcag ggcaccttca agtccaacta cggcaccgac ttcatcctta  7080
agattgagga catcaccgac agcaagctcc gcaacaacaa cggctccggg acggtcgtac  7140
aggagatcaa ggtgccactc atccgcaccg agatttgata ggggtccccg gtccgatgaa  7200
gtgccatcat gccatggatg cggggtgaaa gctcgcggcg tcgaatataa tctccggttc  7260
cagtttcagc tactatggcg actcgtgtcg tgtgtgtgtg gttactctgc ttttgtatgt  7320
ttggtaatgg tgtgtgcgct gttgtccaga gtttcatggt ggtactgctt cctagcagtg  7380
ttgtgtacta gtctcggtac tttgcctgta tgttgagctc ggctcagtat gttctgggag  7440
tgaataaata aaaataaaaa aaaccagata ttgtagtata ctaactgccg ttgctctgtt  7500
tcatccacat acacagaatc ctatgaactg atctttgtgg ggacttggga gccatctgct  7560
cggatcttct tcatgggatt ctctcaattt ctcctcattt ttctaaggct gtgtgtttag  7620
atgtagggag aaaagttttt ggattgtaca tcgtgttggg tactaattta gtctactact  7680
ccgtccgtga atagatgaca ttttctttcg gtgttgttcg tcgtgccaca aagttttgaa  7740
tttatttata tgcaatcctg caggtgttta aacacctgca ggtctgcatg ttcagttagc  7800
acaagcaggt tgcagcttca ccaaacacat acagtcggcc attgctgctt caccaaacat  7860
aaacactacc tgttggagct acaccaaaca cttgcactga ccaaagaaca ttaatagatc  7920
atcaggactg ttcaagtaat cacgcatgac aagatagaaa gcagcaggtc cccttccttc  7980
tcaaagtagc ctgcagcttc attctttggt tcaccattac ataaacagca aaaccagaaa  8040
tagcagacaa taattcctcc tctaggtaaa taaccagaca cagtaatacc ctcacaagta  8100
ccacttatta ggacagtaca atacaaatga tagcaagggg cagatcaaga atcacaacac  8160
agaagccaca aaacatgata agcgcagcag accaaaagct tcttctcaaa gggcgcccgg  8220
accgtcagtt gttggtctgg ctgtacatga catccgactt ctgaatccac ttgtgtagca  8280
ccttcaggtc cttcccgccg accgtcgccc agagctctac gctagcatct ttcgtcgggt  8340
aggtcccgcc gttagggttc ttgagattaa acgtaatctg gaacaagaac gggctcggct  8400
tgctgacggt ctggaccttc ttgccgttca cgcggatctt gtagctcgac acgttgttgt  8460
agaagatgtc gggcagcttg tacaggctga ggccggagta caggtttgga ttctctgaga  8520
gataccacca gcctgagaat ttgtgggcgt cgatcataac tttctcgatc tcggactcgc  8580
caagctcagc gactttcact ttgaggttgt cgttcttctc gtcaacggcg tagagctcca  8640
taggcgtgat cgcagtgatg ctgccgtacg tcaccgtccg cttcccgttg gcgtccagag  8700
gcggcgcagg gatgatgcta ccgaggcggc cgttgatctt ccactggtat cggatcttgc  8760
tactcggcac gcgagtgaac gtggcaccga tcaccatctc gtcgttggag ccgaaggacc  8820
acttctcaaa gatgtgtttc ttctgcaggt tctcgttggt cttccactcg atcacggaga  8880
catcgtcgaa gtgcaggttg gcgttcccgt tattcttcag gccgatgatc ttgaagtatt  8940
cagggttatt gaacgtgttg aaggagaact ccgctatctt ccacttcccg ccggtcacct  9000
tcccggaaac cttcgcgcct tgcccgttgc cggagctgtt gtcagcgtag aagacgacct  9060
cgttgctccc agtggtgctg gcggtgcgca cgtacgcccg cacagtgtag gaggtgtatg  9120
gcttcagctg cgggtttgac atcgccgtgc cgtgcccgtc agtgccgatc cgcccgcgct  9180
tcttgccggt gtagcctccg gattcttggt aggtgtagta ccacaggttc tctgaggtct  9240
cgaagtcgta gtacttgatc gggacgtgta gcgtgatctt catgccgcgc ttccacttca  9300
cgtcgtacac cgtcttgccg ggcatctggt tcagctggcg ctcgatttct ttcttcgtgt  9360
tctcgtccgt gatgaggttg atggaaggct catcaatgaa gatgtccttc tcaccctggt  9420
ccgtgtagta cagtctgccg tccttctcct gagcgttaaa cgccttcttg atggcctcct  9480
tgatggtgat ctccggagtc ttgtcctccg gatcgttcat gttcttcgcc gcgacccggc  9540
gctcgaggct atccttgccc gtgccgaggt taagagtaag gctcccactg acagcgtcaa  9600
tgtttgtccg gatcgggtcc cactcgcctc cgggtatcac ctggcctttc tcgtcgagga  9660
taccgtactg gccgcggttc tgcgtagtct cgatgttgag aatctccgtg cccgcctgga  9720
tcttgtccag ctgctcggcg ttgatcgcta tcttcacggt gcccgcctcg ttggccttgt  9780
ctagggagat aggagcctgg cccttctgcg gataggtgtc gccggcaccg agcgagttgc  9840
cgatctggtt agggccggcg gtgatcgtgg tgatgctgtc gcctgagttc tggaagacga  9900
agttggtggt cggcttcagg tcgtagatgg gcgcggtgcc accattgtaa tagcgcacgt  9960
tcgcgttgag atacgccctc tcggcagtgt tgatccctat ctgcgaactc caggtagtag  10020
agtcggtgtc ggccacactt gtggacgacg accagctgtg ggtgtacttt ggtgagattg  10080
agaaactgaa gcccttgtcg ctgaagccca ggctgccgcc gatctcgacg gtgttggtcg  10140
tggtgtcggt cttagttgta gtcttgctct ttgtatccgc gttgccctcc gtcaccgtat  10200
cgttcttgct gaagtggagc ttctccattc cgacgccaac ggagggatag gcggccacta  10260
gaggatcgcg cgcctcatac ttcgtagcag cgggcatgtg cccagtcacc ttctcgaagt  10320
cggtgtacgg gtctttgacc gtacgggcgt ggtaagggtt gctcacgtac ttcttgtagc  10380
cttctgcact gtaggcgtcg ttccacggca cgatctgctg gttacggaag gtgtatcctt  10440
tctcttccca ttcatcaggg atgcagtcgt tgtcggtgtc caccggcgtg gacatcgact  10500
gcttctcgcc gttctcttgc tggcggtcga agaggttgta gttcgggaag aagctctggg  10560
tctccttctc cgcgagagag ttcgccttct cgctgaaatt cgggctcagt atgtacttct  10620
ccgggatctg ttccttctgc gcgttgttca tcgaccagaa gagctgtagg tccggcaggg  10680
tgttggaggt gttcctgtac tcgatcttaa tctcgtagac ctggtttgcc tctagtttga  10740
ggttcttctg gatgctcgcc tggttgatga ccgtctcgcc attgatctgg aggattacgt  10800
tctcgtcgga ggatgtggag aggcggtact cgccggtctg cgggctcttc aggttgccca  10860
tccaccgaat ggactggatc tgctgggcgt ccgtgttgat gcgagccttg ttcatgaggt  10920
tggacttctc gcccacctgg atgaacatga gctccttgaa ggttgagtcc ttgaagtaga  10980
agccgaccag gccgatgacc gtcgcttgct cactcttgga ggagacaatg ttctgcatgg  11040
tggtggccgg ccaagtaacg gtccgctacc ctgcaagagg tagcaaaaaa ggggtatcag  11100
ttaacagcaa gtgtatcctg ctagatagta gctgtacaag ggaaccagta agcatcgtaa  11160
acataaaagt tttgaaggca tatcaactga acctttatat ttgtgcatct ataagtcaat  11220
aaaaacaaca tatgtacaga gcttactgcc aggcaaaagt gggattcatt tcaccgacta  11280
ggctaatgtt gtactccctc cgttccaaat tgtaggtcgt tttgactttt ctagattcat  11340
agatattatt atgcacctag acatacacta tatctagatg cataataata tctatgaacc  11400
tacaaaagtc aaaacgacct acaatttgga acggagagag taagaaataa tctgataact  11460
tgcggactgt tgtttccaac atttataaaa atgtgtaaag taccataacc aaacattcgt  11520
```

```
ataactaaac atgataggaa aagactagca ttgctttgaa aaagtagtgt acatgtactg  11580
gccaatctaa caagcttttt tgttgtctaa aatgtgacct gcagagcaac aaaaatcaca  11640
tgctgaactt ttcagcctaa catttggtgc catgaaacat cactaagttg tcactaattt  11700
tgggtggtat gtgctcaata gctattcatg acaaggaaac atcctaacat gcagatatgc  11760
tttccaaata gctctctccg aatgaaccac acacggattt ttacactctg gtagttcaat  11820
cacaccaaat taactatccg cgactttcat ccaaccatgt taccagttac cgcaactatc  11880
tggacttgct agacagagca tcacgaagct ctcccagact cccagtcaag caggaaacta  11940
gaacgtcgga gctgggaagt agtcaagcag tcacacccca agggctcgtg catcgccagc  12000
aacacgtaag cgcattcagg cacatcacag tcaccattcc taggtacgta gctcagagag  12060
cctcctcgca cggcagtccc gcaaacacac atcaggcgtg cgcacaaaat cagacgcatc  12120
ggcacgcaga aacgctacag atcaggaaca ggacggagtt catcaagcac agacgtcaga  12180
cgaacaccct agcaccaacc acgaagcacg atccgctggc ggatcgcgcg gtacccgccc  12240
cggatctggc gggagcaccg gaggcaagtg accagaacgc atgagcaaac cgcagatctc  12300
gagccaggcc gctcagatct gagcgccaaa cactcgaaaa atgctggagc aggagctagt  12360
gcgtggggag atcgcgagta gaggggctcc agggagcgga ggggaggggg aggaggagat  12420
taccggggag gccggcctgc tgcagagtac agaaagcact tgcttgatca ctagcgcgaa  12480
gcagaggtgt gcctgccctt agtattaact gatcactaag cgcttgtgat ggttcgtggt  12540
ggcgcttgat tgttgcattt ataggagaac catcggcgca gtgccgatta ttgtaatagc  12600
agtgttgttg tgtgagttta cattcccgtg agcatgagtg catgtgaggg cgattattaa  12660
ttagatggct gatcaatgca gaacagcgca agtggccaag attgctccac tggtggatgc  12720
atgttgatgt ttgttctcgc ttgatggttg atcattttta ttcagtttag gacgaacttg  12780
tcatatgggt tggctgcttg tatctagtaa cgtgatcgag tgctaaacat cagcagaggt  12840
atcatggtga tgcatggacg gtggacgccc aagttgttga acagttgaag tattttttt  12900
tctgcacttc acgggatcca agcgcagagc tatgcataat tgcatatagc ggtgggtacg  12960
ggtgcaccct tgcatggtaa aactgaatgc gctcagaagg caattgcaat cactaaaatt  13020
tgctttagct ctgttcctga tcgggtcaag gtttattatg ttcagttgga acattcaaag  13080
ttagaggctt gaatttgctt aaaaagcatt cccacaaaca acggtgggtg cccttttttgt  13140
atgacgtact gttggctaga tggttccgct tgtttatgaa aaaagagtgt actaataaat  13200
ttacccgaac tcttcactac cgcagataac tcttttgccg agtgcttcat gcacttcaca  13260
aagtccagaa aacacttggc aagctccaag cttaagaaac ataaatgacg tgcataagtt  13320
caaaaatagt ttaatacaag actaagatgt ccaaaagaac ggtaaattat attaaaataa  13380
tacttcttat aatagatcaa tgctatcgaa tagcccactt cactctttaa gcatacataa  13440
attttcaatt atatcataaa atttctacgt cctactgcgt ttcaaccata tttcagcatg  13500
acaattatag taatacaaaa caagaattga attgcttgaa tgtaaatgtt caaagtaaag  13560
aaggattatt aatatgatga tgttttatcg agatatcaga gagtcaacac tcctcattga  13620
tccttgttag agcacccatg taagtgtgtc gctccccctt catccgtgca agcaggatca  13680
aatgctctct agaaggaacg tgggcatcta agagagggat gaatccgaac ataactggga  13740
tttttggagg attctgatga aaccatttac cctaacttga gataactgga gtaaaagatc  13800
cttactgtcc accatttctt gtgatgggtt aaaatccctc ttgccggaga gacctatctc  13860
tatcaggtga tatgcctggt agctgtttcc ttcttcccaa tctggcaggc ccttgttcgt  13920
cactgctgac gtctttttcc tcattattgg aggatgagtc actgcaagct gtaaagcttg  13980
tattattgct ggtggaggcc ccaccttcac atgctgagca tttatggttg tcggccaata  14040
atttcttcag ctgtttgcaa agcaataatt ttgtagatgt ccctacatca actttggcat  14100
gtgcaatgct ttcttcaaag gaagataaga tgtcaacatc ttgtctggag attggtgctc  14160
cgtagtgact catgatcaat accttttttct gtgcgtaatt gatcttgatt tttgtcttcc  14220
cgtcgatggc gcgccaagaa gaacgattgg caaacagcta ttatgggtat tatgggtagg  14280
cctgcccaaa ctagggataa cagggtaata ggtctcacgc ggcaaatcct accacctcat  14340
ttaaatagag tgaggttgat ttgcggccgc tataacttcg tataatgtat gctatacgaa  14400
gttatgtcga ctcgtggtgg ccgcatcgat cgtgaagttt ctcatctaag cccccatttg  14460
gacgtgaatg tagacacgtc gaaataaaga tttccgaatt agaataattt gtttattgct  14520
ttcgcctata aatacgacgg atcgtaattt gtcgttttat caaaatgtac tttcatttta  14580
taataacgct gcggacatct acatttttga attgaaaaaa aattggtaat tactctttct  14640
ttttctccat attgaccatc atactcattg ctgatccatg ta                     14682
```

```
SEQ ID NO: 10          moltype = DNA  length = 16861
FEATURE                Location/Qualifiers
source                 1..16861
                       mol_type = other DNA
                       note = A 16,861 nucleotide sequence corresponding to the
                        contig nucleotide sequence of the 5' genomic flanking DNA
                        nucleotide sequence, the inserted T-DNA nucleotide
                        sequence in event MON95275, and the 3' genomic flanking
                        nucleotide sequence.
                       organism = synthetic construct
SEQUENCE: 10
gaacatttgg cggaagaaca tgttttaagg gctagtttgg aagctcaatt ttcccaagag  60
attcttattt tcccaaggga aaataaacta atttcccttg tgaaaatgaa aatcccttgg  120
aataacgtgg ttcccaaact aaacctaagg gcttttttttt atcattgtgt caaacagttt  180
accagctaat tttagtacct taacatttaa ataggtcagc taaaaaagta gctaattgtt  240
agccgaagaa ctgataaatt atttgtccat tagctatttg accttactaa tagatattaa  300
taaatcatat aaatagtcaa gtcttcaaat ataccctgac taatatttgc tagttaatta  360
tttattttct gattaattat tagccactgc taaacaataa gtcagtacga cccaaacaag  420
gcctagttac tactcctatc cataaaaaaa agttgtttga ccattttgac gccaaattta  480
accggcttat attaccaaaa tatttgaaaa aacattaaaa acagttgctg gttaaagtaa  540
attgtatgat aaactaaatc ggaatgaaaa taaataatag ttataatttt ttaataagat  600
gagccagtca aatttgacaa aaagttaaac cgatattctt tctggaacgg aaggagtaga  660
ctgtgttaat gttatgatat tgtgagcaag agagaagggg gtcgatagca acgacccaag  720
tgagtgggag gaggaaggtt ggggcgacga tgttgtgggg agggtgaagg atgatctaaa  780
taatattgtt cgctggattt gagtgagtaa gagcaacccc aacagtttag atataaatcc  840
```

```
tagctaaatt tagagtcttg ccaagagatt tttatttttt caaaaaaata gtttattttt  900
ctttgggaaa tagaaatctc ttggaacaat agtgttttta aactagtctt ggcgtttgta  960
aagaagatag atagactcca attttttatg aagacgggtc aaaactcaac aaatcaacgg  1020
ataccgtccc ttttttggcg catgaagttt caggtctgta gcagccggcc cgatcaaaca  1080
ctgatagttt cccggtaact ataacggtcc taaggtagcg acttaggctg agcccgggca  1140
ggcctaccca taatacccat aatagctgtt tgccaatcgt tcttcttggc gcgccgttgt  1200
caatcaattg gcaagtcata aaatgcatta aaaaatattt tcatactcaa ctacaaatcc  1260
atgagtataa ctataattat aaagcaatga ttagaatctg acaaggattc tggaaaatta  1320
cataaaggaa agttcataaa tgtctaaaac acaagaggac atacttgtat tcagtaacat  1380
ttgcagcttt tctaggtctg aaaatatatt tgttgcctag tgaataagca taatggtaca  1440
actacaagtg ttttactcct catattaact tcggtcatta gaggccacga tttgacacat  1500
ttttactcaa aacaaaatgt ttgcatatct cttataattt caaattcaac acacaacaaa  1560
taagagaaaa aacaaataat attaatttga gaatgaacaa aaggaccata tcattcatta  1620
actcttctcc atccatttcc atttcacagt tcgatagcga aaaccgaata aaaaacacag  1680
taaattacaa gcacaacaaa tggtacaaga aaaacagttt tcccaatgcc ataatactca  1740
aactcagtag gattctggtg tgtgcgcaat gaaactgatg cattgaactt gacgaacgtt  1800
gtcgaaaccg atgatacgaa cgaaagctag gcctcagcga gtaccgctgg cgatctaatc  1860
catgatatcg tgaacatcat ctacattcaa attcttatga gctttcttaa gggcatctgc  1920
agcatttttc atagaatcta atacagcagt atttgtgcta gctccttcga gggcttccct  1980
ctgcatttca atagttgtaa gggttccatc tatttgtagt tgggtctttt ccaatcgttt  2040
cttcttttttg agggcttgga gtgcaactct tttatttttc gacgcatttt tctttgcgct  2100
cctgcaggcg gccgcgtgga tgaggagtta atcggtcgtg tgagagtagt gatcgagtgg  2160
atgtcgtcga gagtgatgag tgttgatgtt gttagtgata tgtggtagaa ggtatcgtga  2220
taaagcgtta acgcgatcgc agtacttgca aagaaaaatg cgtcgaaaaa taaaagagtt  2280
gcactccaag ccctcaaaaa gaagaaacga ttggaaaaga cccaactaca aatagatgga  2340
acccttacaa ctattgaaat gcagagggaa gccctcgaag gagctagcac aaatactgct  2400
gtattagatt ctatgaaaaa tgctgcagat gcccttaaga aagctcataa gaatttgaat  2460
gtagatgatg ttcacgatat catggatggt atcgcacagc gactgctgag ggacgtcgag  2520
ctcccgcttg gtatctgcat tacaatgaaa tgagcaaaga ctatgtgagt aacactggtc  2580
aacactaggg agaaggcatc gagcaagata cgtatgtaaa gagaagcaat atagtgtcag  2640
ttggtagata ctagatacca tcaggaggta aggagagcaa caaaaaggaa actctttatt  2700
tttaaatttt gttacaacaa acaagcagat caatgcatca aaatactgtc agtacttatt  2760
tcttcagaca acaatattta aaacaagtgc atctgatctt gacttatggt cacaataaag  2820
gagcagagat aaacatcaaa atttcgtcat ttatatttat tccttcaggc gttaacaatt  2880
taacagcaca caaacaaaaa cagaatagga atatctaatt ttggcaaata ataagctctg  2940
cagacgaaca aattattata gtatcgccta taatatgaat ccctatacta ttgacccatg  3000
tagtatgaag cctgtgccta aattaacagc aaacttctga atccaagtgc cctataacac  3060
caacatgtgc ttaaataaat accgctaagc accaaattac acatttctcg tattgctgtg  3120
taggttctat cttcgtttcg tactaccatg tccctatatt ttgctgctac aaaggacggc  3180
aagtaatcag cacaggcaga acacgatttc agagtgtaat tctagatcca gctaaaccac  3240
tctcagcaat caccacacaa gagagcattc agagaaacgt ggcagtaaca aaggcagagg  3300
gcggagtgag cgcgtaccga agacggtcgt acggaaaata gagagagata gatttgtaga  3360
gagagactgg tgatttcagc gtgtcctctc caaatgaaat gaacttcctt atatagagga  3420
agagtcttgc gaaggatagt gggattgtgc gtcatccctt acgtcagtgg agatatcaca  3480
tcaatccact tgctttgaag acgtggttgg aacgtcttct ttttccacga tgctcctcgt  3540
gggtgggggt ccatctttgg gaccactgtc ggcagaggca tcttgaacga tagcctttcc  3600
tttatcgcaa tgatggactt tgtaggagcc accttccttt tctactgtcc tttccatgaa  3660
gtgacagata gatgggcaat ggaatccgag gaggtttcct gatattaccc tttgttgaaa  3720
agtctcaata gccctttggt cttctgagac tgtatctttg atattcttgg agtagacgag  3780
agtgtcgtgc tccaccatgt tgacgaagat tttcttcttg tcattgagtc gtaaaagact  3840
ctgtatgaac tgtccgccag tcttcacggc gagttctgtt agatcctcga tctgaatttt  3900
tgactccttg ctgatggacg gtgtggaggg aggtgctttc gtgcttggcg gcatgcacgg  3960
gtaatcggca acgcatgtgt gctttgagcg ttgcctggtt gtcatgggat acaggacaac  4020
aaccatcgtc atgtggagat cgatcgagat ataggatcgg agcaagttga caaatcatgt  4080
caaaatcact caacgaggta gcatgttgta taaacagatc aatgcagaaa tacattagtg  4140
ctagctggaa ttgttccgat cagctggcgc tattattatt ttatcgaaac tgatgcgtgt  4200
gcgtgctcgc cttattttgt gttctgcggg ggcggctccc gcgaatacct attatttctg  4260
tgagcgctcc cttcaaaagt gacatgattt tatatatccc tctacgatac gacgaccaga  4320
tcaagctacc actaccaccg aaatcaggac ctctgctaac cggtggccca gaccggacaa  4380
aagttattgc attgtatatg ggtagggttt atgtccattt tacatcgcgc atagtacgca  4440
caatttctgt tggcccatca atatataccg agtgtgctgc agcctatagt gatagagttt  4500
tacttaattc taagcctagg atccgaacag tgattggaaa tccttagtta cagtctgaca  4560
gtataaaggt cactctcact acctggtagt agagccatga cccggtgctg atatcactat  4620
caggtacagc cataaccaca gtgctagtgg aaatatcact acgtactagg ccaatctata  4680
atctgatgag aacacatata gttgacatag tcgatacgta cccatgttat gagtcccgag  4740
tgactgtcaa ggacatgatt tgagttttgg taagtgtgtg ttggacaaat cgaagcatga  4800
gtagggttca tggcctgtga tttgtactag tctaactaac taaattatcg tgtacaaccg  4860
ttgatctgag agggtcccgc gctgcaaatc tattgtaata ctccctgtcg taatactgtg  4920
ttaatttgtg ctcagtcgga cggctcagac tttacggtga tataaacctt tactgagctg  4980
aactcgacct ggagatcgaa tcgaccccgc aggtgttccg aagcgtacca cggcgagcgt  5040
taggtctaag caaaagccac acccttcaca gaacgaagga gtttcgcgaa gtcacgctga  5100
tttaaaaaga gcgggccact ttttccactc ttggtcaaca gaaaaaggcg gacgagttca  5160
gatttaaggc cagctgcacg ccgatcagca gattcgacgt tacccgcgga gagaaggctg  5220
cctgctactt cccagtcgaa agtggtgtag ttcaagtgat ctctaaagct aaggctccgc  5280
tggtcctagt cgttaattac cgagcagctc tccggcgtac agaaccacga agttacttct  5340
tgaggtgaag cgtaagtggt ggtgagggta agtagttgga agcagaagcc ttaagtgata  5400
caatctggct tccaccttgt cggaactcgt taaaatttcc cttgattaca atataagtac  5460
ctgcctgatc gttctggtag cctgatcgat ttttattttt gggctacggg caattgctcg  5520
caatttattg aagtcgcacg ggcgcgaaag aagacgttgt tctctctgct tgctagaagc  5580
```

-continued

```
cgcggataag cgattctatc cgatatttaa gacccgtgta gaccagcaga cgtgagtggg  5640
ccgtttccag aaaccgtctc tccttgcgac gatagatccg atagtaagta acttcacccc  5700
tgatcaacgg cgtagtcgcc tgtctggttc ggatctgtat agatttggcg gattccgctt  5760
gcgaaatctt tagcagctta ggtccggagc cccggtgga tctggctgtt cagcggcacg  5820
gtccaatctc cttagctcct ctgtgaacag cagtcgaact ctaagattct tgatacgcgc  5880
aacacgggcc ttggcgagcc tggggataac tcgcgaggac gctctcgccg cgctaaagcg  5940
tgcgatcaca ccgctccgac aagtgacttt gccaaatcta gaaagagaga ctacactgct  6000
tgccggtgca gtcttgatcc accttggagg ggctgacgct aactaactaa ggcgcgcctg  6060
cctactaggc ctcgaccctt gttcgtcact gctgacgtct ttttctccat tattggagga  6120
tgagtcactg caagctgtaa agcttgtatt attgctagtg gaggccccac ctgcacatgc  6180
cgagcaatta tgattgtcgg ccagtagctt tttgagctgt ttgcagagca ataacttagt  6240
ggatgtcccc accattacat cgttattgat gatgctttct tcaaaggaag ataagatgct  6300
gacatcctgt ctggagattg tcgctccata gtgactcgtg atcaatactc tttcatgtga  6360
gtaattgatt tttatctttg tttctccgtt gatggcctac taggccaaat ggatgaaaca  6420
acttggacca atcagagatg gccacgtcag ctcccgatcg tcgtaaccga ccaaacccga  6480
tcgataacgg tttaggctcc aatacaccgt cggtaccacc cggtcgctat catctgcccc  6540
cgtcccaacg ctattggtat cgtccgcccc tatatcggtc ggtagcccag tccaccgtcg  6600
gggccaatcg tcccctgctg cgtccgctcg tgtcggtacc gatcgccaaa aacgccacgt  6660
caacggcact gcggtaccga ccgccgctgg caccggcctt agcgggccac acgaccgatc  6720
gctgttgtac ggacgtagag gtgaatcatg cgattgaatt ttcgctagag gaaagttatc  6780
atcttattat ctccaaccct ccttcctacg gctggatccg acgaaaattt accctggacg  6840
gtgccagtaa caattgcagg tctcactcac gtgctaaatc cagcaatcaa acacgaagga  6900
atatacgtga tctggccaga acatgcaaga gaataataca gtagtgttag agtacgaaac  6960
ctacacgatt caacgaatta atcaatgggt tcacgttcac gggtatgctc gcgcacgtcc  7020
aaaatccaac gacattttta taagcggcat gatccagacg ggccagctcg agcaccacat  7080
ggcgtggctc catctcgcat cccccatcac cgctataaat accattggcc atgcacaccc  7140
gcactcccac acagcacaag cagcagcagc agcagcagct cgatcgaact agcttagcta  7200
ctacgtgcgc gtgcaacaag cagctcgatc gatcgccctc acggtaattt cttctcccaa  7260
aataaaccta atctttaatc tgttgcctgt ctactcttcc tatctgttgc taaaaatttg  7320
aatttggtat gtgcaggagg acttaattaa gggacccacc gccatgtcat ccacggacgt  7380
gcaagagcgc ctgcgggact tggcgcgcga agacgaggcg ggaacgttca acgaggcttg  7440
gaacaccaac ttcaagccgt cggacgagca gcaattcagc tactcgccga cggagggaat  7500
tgtcttcctc acgccgccta agaacgtcat cggtgagcgg cgcatctccc agtacaaggt  7560
gaacaatgcc tgggcaactc tggagggctc tcccaccgag gcgagcggta cgccgttgta  7620
cgcgggcaag aatgtactgg acaactcgaa aggcacaatg gaccaggagt tgcttacacc  7680
cgagttcaac tacacctaca cggagagcac gagcaacacg acgacgcacg gcctcaaact  7740
cggcgtgaag accaccgcga ccatgaagtt ccctatcgct caaggctcga tggaggcgag  7800
caccgagtac aatttccaga actcctccac cgataccaag accaaacaag tgtcttacaa  7860
gtctccgagc cagaagatta aggttcctgc gggcaagacg taccgcgtgc tggcgtacct  7920
gaacaccggc tctatctctg gcgaggctaa cctgtacgcg aacgtcggcg gcatcgcgtg  7980
gcgggtctcg ccaggctatc ctaacggcgg cggcgtgaac atcggcgctg tcctgaccaa  8040
gtgccagcag aagggttggg gcgacttccg caacttccag ccctccgggc gcgacgtcat  8100
cgtgaagggt cagggcacct tcaagtccaa ctacggcacc gacttcatcc ttaagattga  8160
ggacatcacc gacagcaagc tccgcaacaa caacggctcc gggacggtcg tacaggagat  8220
caaggtgcca ctcatccgca ccgagatttg ataggggtcc ccggtccgat gaagtgccat  8280
catgccatgg atgcggggtg aaagctcgcg gcgtcgaata taatctccgg ttccagtttc  8340
agctactatg gcgactcgtg tcgtgtgtgt gtggttactc tgcttttgta tgtttggtaa  8400
tggtgtgtgc gctgttgtcc agagtttcat ggtggtactg cttcctagca gtgttgtgta  8460
ctagtctcgg tactttgcct gtatgttgag ctcggctcag tatgttctgg gagtgaataa  8520
ataaaaataa aaaaaaccag atattgtagt atactaactg ccgttgctct gtttcatcca  8580
catacacaga atcctatgaa ctgatctttg tggggacttg ggagccatct gctcggatct  8640
tcttcatggg attctctcaa tttctcctca tttttctaag gctgtgtgtt tagatgtagg  8700
gagaaaagtt tttggattgt acatcgtgtt gggtactaat ttagtctact actccgtccg  8760
tgaatagatg acattttctt tcggtgttgt tcgtcgtgcc acaaagtttt gaatttattt  8820
atatgcaatc ctgcaggtgt ttaaacacct gcaggtctgc atgttcagtt agcacaagca  8880
ggttgcagct tcaccaaaca catacagtcg gccattgctg cttcaccaaa cataaacact  8940
acctgttgga gctacaccaa acacttgcac tgaccaaaga acattaatag atcatcagga  9000
ctgttcaagt aatcacgcat gacaagatag aaagcagcag gtccccttcc ttctcaaagt  9060
agcctgcagc ttcattcttt ggttcaccat tacataaaca gcaaaaccag aaatagcaga  9120
caataattcc tcctctaggt aaataaccag acacagtaat accctcacaa gtaccactta  9180
ttaggacagt acaatacaaa tgatagcaag gggcagatca agaatcacaa cacagaagcc  9240
acaaaacatg ataagcgcag cagaccaaaa gcttcttctc aaagggcgcc cggaccgtca  9300
gttgttggtc tggctgtaca tgacatccga cttctgaatc cacttgtgta gcaccttcag  9360
gtccttcccg ccgaccgtcg cccagagctc tacgctagca tctttcgtcg ggtaggtccc  9420
gccgttaggg ttcttgagat taaacgtaat ctggaacaag aacgggctcg gcttgctgac  9480
ggtctggacc ttcttgccgt tcacgcggat cttgtagctc gacacgttgt tgtagaagat  9540
gtcgggcagc ttgtacaggc tgaggccgga gtacaggttt ggattctctg agagatacca  9600
ccagcctgag aatttgtggg cgtcgatcat aactttctcg atctcggact cgccaagctc  9660
agcgactttc actttgaggt tgtcgttctt ctcgtcaacg gcgtagagct ccataggcgt  9720
gatcgcagtg atgctgccgt acgtcaccgt ccgcttcccg ttggcgtcca gaggcggcgc  9780
agggatgatg ctaccgaggc ggccgttgat cttccactgg tatcggatct tgctactcgg  9840
cacgcgagtg aacgtggcac cgatcaccat ctcgtcgttg gagccgaagg accacttctc  9900
aaagatgtgt ttcttctgca ggttctcgtt ggtcttccac tcgatcacgg agacatcgtc  9960
gaagtgcagg ttggcgttcc cgttattctt caggccgatg atcttgaagt attcagggtt  10020
attgaacgtg ttgaaggaga actccgctat cttccacttc ccgccggtca ccttcccgga  10080
aaccttcgcg ccttgcccgt tgccggagct gttgtcagcg tagaagacga cctcgttgct  10140
cccagtggtg ctggcggtgc gcacgtacgc ccgcacagtg taggaggtgt atggcttcag  10200
ctgcgggttt gacatcgccg tgccgtgccc gtcagtgccg atccgcccgc gcttcttgcc  10260
ggtgtagcct ccggattctt ggtaggtgta gtaccacagg ttctctgagg tctcgaagtc  10320
```

```
gtagtacttg atcgggacgt gtagcgtgat cttcatgccg cgcttccact tcacgtcgta  10380
caccgtcttg ccgggcatct ggttcagctg gcgctcgatt tctttcttcg tgttctcgtc  10440
cgtgatgagg ttgatggaag gctcatcaat gaagatgtcc ttctcaccct ggtccgtgta  10500
gtacagtctg ccgtccttct cctgagcgtt aaacgccttc ttgatggcct ccttgatggt  10560
gatctccgga gtcttgtcct ccggatcgtt catgttcttc gccgcgaccc ggcgctcgag  10620
gctatccttg cccgtgccga ggttaagagt aaggctccca ctgacagcgt caatgtttgt  10680
ccggatcggg tcccactcgc ctccgggtat cacctggcct ttctcgtcga ggataccgta  10740
ctggccgcgg ttctgcgtag tctcgatgtt gagaatctcc gtgcccgcct ggatcttgtc  10800
cagctgctcg gcgttgatcg ctatcttcac ggtgcccgcc tcgttggcct tgtctaggga  10860
gataggagcc tggcccttct gcggatatgt gtcgccggca ccgagcgagt tgccgatctg  10920
gttagggccg gcggtgatcg tggtgatgct gtcgcctgag ttctggaaga cgaagttggt  10980
ggtcggcttc aggtcgtaga tgggcgcggt gccaccattg taatagcgca cgttcgcgtt  11040
gagatacgcc ctctcggcag tgttgatccc tatctgcgaa ctccaggtag tagagtcggt  11100
gtcggccaca cttgtggacg acgaccagct gtgggtgtac tttggtgaga ttgagaaact  11160
gaagcccttg tcgctgaagc ccaggctgcc gccgatctcg acggtgttgg tcgtggtgtc  11220
ggtcttagtt gtagtcttgc tctttgtatc cgcgttgccc tccgtcaccg tatcgttctt  11280
gctgaagtgg agcttctcca ttccgacgcc aacggaggga taggcggcca ctagaggatc  11340
gcgcgcctca tacttcgtag cagcgggcat gtgcccagtc accttctcga agtcggtgta  11400
cgggtctttg accgtacggg cgtggtaagg gttgctcacg tacttcttgt agccttctgc  11460
actgtaggcg tcgttccacg gcacgatctg ctggttacgg aaggtgtatc ctttctcttc  11520
ccattcatca gggatgcagt cgttgtcggt gtccaccggc gtggacatcg actgcttctc  11580
gccgttctct tgctggcggt cgaagaggtt gtagttcggg aagaagctct gggtctcctt  11640
ctccgcgaga gagttcgcct tctcgctgaa attcgggctc agtatgtact tctccgggat  11700
ctgttccttc tgcgcgttgt tcatcgacca gaagagctgt aggtccggca gggtgttgga  11760
ggtgttcctg tactcgatct taatctcgta gacctggttt gcctctagtt tgaggttctt  11820
ctggatgctc gcctggttga tgaccgtctc gccattgatc tggaggatta cgttctcgtc  11880
ggaggatgtg gagaggcggt actcgccggt ctgcgggctc ttcaggttgc ccatccaccg  11940
aatggactgg atctgctggg cgtccgtgtt gatgcgagcc ttgttcatga ggttggactt  12000
ctcgcccacc tggatgaaca tgagctcctt gaaggttgag tccttgaagt agaagccgac  12060
caggccgatg accgtcgctt gctcactctt ggaggagaca atgttctgca tggtggtggc  12120
cggccaagta acggtccgct accctgcaag aggtagcaaa aaaggggtat cagttaacag  12180
caagtgtatc ctgctagata gtagctgtac aagggaacca gtaagcatcg taaacataaa  12240
agttttgaag gcatatcaac tgaaccttta tatttgtgca tctataagtc aataaaaaca  12300
acatatgtac agagcttact gccaggcaaa agtgggattc atttcaccga ctaggctaat  12360
gttgtactcc ctccgttcca aattgtaggt cgttttgact tttctagatt catagatatt  12420
attatgcacc tagacataca ctatatctag atgcataata atatctatga acctacaaaa  12480
gtcaaaacga cctacaattt ggaacggaga gagtaagaaa taatctgata acttgcggac  12540
tgttgtttcc aacatttata aaaatgtgta aagtaccata accaaacatt cgtataacta  12600
aacatgatag gaaaagacta gcattgcttt gaaaaagtag tgtacatgta ctggccaatc  12660
taacaagctt ttttgttgtc taaaatgtga cctgcagagc aacaaaaatc acatgctgaa  12720
cttttcagcc taacatttgg tgccatgaaa catcactaag ttgtcactaa ttttgggtgg  12780
tatgtgctca atagctattc atgacaagga aacatcctaa catgcagata tgctttccaa  12840
atagctctct ccgaatgaac cacacacgga tttttacact ctggtagttc aatcacacca  12900
aattaactat ccgcgacttt catccaacca tgttaccagt taccgcaact atctggactt  12960
gctagacaga gcatcacgaa gctctcccag actcccagtc aagcaggaaa ctagaacgtc  13020
ggagctggga agtagtcaag cagtcacacc ccaagggctc gtgcatcgcc agcaacacgt  13080
aagcgcattc aggcacatca cagtcaccat tcctaggtac gtagctcaga gagcctcctc  13140
gcacggcagt cccgcaaaca cacatcaggc gtgcgcacaa aatcagacgc atcggcacgc  13200
agaaacgcta cagatcagga acaggacgga gttcatcaag cacagacgtc agacgaacac  13260
cctagcacca accacgaagc acgatccgct ggcggatcgc gcggtacccg ccccggatct  13320
ggcgggagca ccggaggcaa gtgaccagaa cgcatgagca aaccgcagat ctcgagccag  13380
gccgctcaga tctgagcgcc aaacactcga aaaatgctgg agcaggagct agtgcgtggg  13440
gagatcgcga gtagaggggc tccagggagc ggaggggagg gggaggagga gattaccggg  13500
gaggccggcc tgctgcagag tacagaaagc acttgcttga tcactagcgc gaagcagagg  13560
tgtgcctgcc cttagtatta actgatcact aagcgcttgt gatggttcgt ggtggcgctt  13620
gattgttgca tttataggag aaccatcggc gcagtgccga ttattgtaat agcagtgttg  13680
ttgtgtgagt ttacattccc gtgagcatga gtgcatgtga gggcgattat taattagatg  13740
gctgatcaat gcagaacagc gcaagtggcc aagattgctc cactggtgga tgcatgttga  13800
tgtttgttct cgcttgatgg ttgatcattt ttattcagtt taggacgaac ttgtcatatg  13860
ggttggctgc ttgtatctag taacgtgatc gagtgctaaa catcagcaga ggtatcatgg  13920
tgatgcatgg acggtggacg cccaagttgt tgaacagttg aagtattttt ttttctgcac  13980
ttcacgggat ccaagcgcag agctatgcat aattgcatat agcggtgggt acgggtgcac  14040
ccttgcatgg taaaactgaa tgcgctcaga aggcaattgc aatcactaaa atttgcttta  14100
gctctgttcc tgatcgggtc aaggtttatt atgttcagtt ggaacattca aagttagagg  14160
cttgaatttg cttaaaaagc attcccacaa acaacggtgg gtgccctttt tgtatgacgt  14220
actgttggct agatggttcc gcttgtttat gaaaaaagag tgtactaata aatttacccg  14280
aactcttcac taccgcagat aactcttttg ccgagtgctt catgcacttc acaaagtcca  14340
gaaaacactt ggcaagctcc aagcttaaga aacataaatg acgtgcataa gttcaaaaat  14400
agtttaatac aagactaaga tgtccaaaag aacggtaaat tatattaaaa taatacttct  14460
tataatagat caatgctatc gaatagccca cttcactctt taagcataca taaatttcca  14520
attatatcat aaaatttcta cgtcctactg cgtttcaacc atatttcagc atgacaatta  14580
tagtaataca aaacaagaat tgaattgctt gaatgtaaat gttcaaagta aagaaggatt  14640
attaatatga tgatgtttta tcgagatatc agagagtcaa cactcctcat tgatccttgt  14700
tagagcaccc atgtaagtgt gtcgctcccc cttcatccgt gcaagcagga tcaaatgctc  14760
tctagaagga acgtgggcat ctaagagagg gatgaatccg aacataactg ggatttttgg  14820
aggattctga tgaaaccatt taccctaact tgagataact ggagtaaaag atccttactg  14880
tccaccattt cttgtgatgg gttaaaatcc ctcttgccgg agagacctat ctctatcagg  14940
tgatatgcct ggtagctgtt tccttcttcc caatctggca ggcccttgtt cgtcactgct  15000
gacgtctttt tcctcattat tggaggatga gtcactgcaa gctgtaaagc ttgtattatt  15060
```

```
gctggtggag gccccacctt cacatgctga gcatttatgg ttgtcggcca ataatttctt  15120
cagctgtttg caaagcaata attttgtaga tgtccctaca tcaactttgg catgtgcaat  15180
gctttcttca aaggaagata agatgtcaac atcttgtctg gagattggtg ctccgtagtg  15240
actcatgatc aataccttt  tctgtgcgta attgatcttg atttttgtct tcccgtcgat  15300
ggcgcgccaa gaagaacgat tggcaaacag ctattatggg tattatgggt aggcctgccc  15360
aaactaggga taacagggta ataggtctca cgcggcaaat cctaccacct catttaaata  15420
gagtgaggtt gatttgcggc cgctataact tcgtataatg tatgctatac gaagttatgt  15480
cgactcgtgg tggccgcatc gatcgtgaag tttctcatct aagcccccat ttggacgtga  15540
atgtagacac gtcgaaataa agatttccga attagaataa tttgtttatt gctttcgcct  15600
ataaatacga cggatcgtaa tttgtcgttt tatcaaaatg tactttcatt ttataataac  15660
gctgcggaca tctacatttt tgaattgaaa aaaaattggt aattactctt tctttttctc  15720
catattgacc atcatactca ttgctgatcc atgtaactat aacacagagg ctggccaacc  15780
tggaggcgca gcggcgccac aaggtccaga tctcgttcat cctggccacg ttgctcgcga  15840
ctccgaggac gtgcaggcca ctcgtcgtag ctctacctcg gcagcctctg tcgcgactcc  15900
gaggacgtgc aggccgcgca gctcgcgcgc tccttccgtg ccctctccgg ttttgtgatt  15960
ccctgcgccc tctccggctt cgccgccgca tccgggttta cgtggtggtg ggccaccgca  16020
gtcccaccat ccgcgaggca gccagcaggg cccccgcgct cgacgatagg ctgctgaagc  16080
ccctcgccca tcaccgtctt ctggggcgtg cctactgcga ggaggatggg gtcttccaca  16140
ccatgccaca aggtgttcga cgctcgttcc aactccgacg cgcagcctgt ctgctcgccc  16200
atcaccggcc acctgtctgg acgcgcagcc tgctgcgtca acatgctcag cagcatcaac  16260
tgctcaagaa gctacaccaa catcactcct cttcctccac gggggactgg attcgccatt  16320
ggtacctgct gcttcatgct caaccaacac ccttcttgcc aaggatgatg gagattatat  16380
gaaccggtgt ttcagttggt gttggaagtc cccatggtta catccagatc agtcggaatt  16440
tagagacttc ctccaatggt cttcttggca tttccaattt gtcaggtgca gagcatcaca  16500
gttaccaatt ccttggccac cacctataac attgcgtttg gttagagatg accttgttgt  16560
gatgccagtg attccaagta tgctattgtt atctcagtgc tatttcagtg gagtagaatg  16620
tgtgctgaca actatagatc cattattttc taaattttgt gctgagagag agctgttctg  16680
gaagccacct tggcaacctc cagttcctaa caccagatct gagataccgt tgttgataga  16740
gtttgtccat cttactacag gagtctgtga tactctgcat atggttactg aatttcctaa  16800
gcaatacttt gttggcctgc ttgtgctgat tacaagggaa tttttcatgt ctgggagaat  16860
a                                                                 16861
```

```
SEQ ID NO: 11          moltype = DNA  length = 1073
FEATURE                Location/Qualifiers
source                 1..1073
                       mol_type = genomic DNA
                       note = A 1,073 nucleotide sequence representing the 5'
                        flanking corn genomic DNA up to the inserted T-DNA.
                       organism = Zea mays
SEQUENCE: 11
gaacatttgg cggaagaaca tgttttaagg gctagtttgg aagctcaatt ttcccaagag  60
attcttattt tcccaaggga aaataaacta atttcccttg tgaaaatgaa aatcccttgg  120
aataacgtgg ttcccaaact aaacctaagg gcttttttt  atcattgtgt caaacagttt  180
accagctaat tttagtacct taacatttaa ataggtcagc taaaaaagta gctaattgtt  240
agccgaagaa ctgataaatt atttgtccat tagctatttg accttactaa tagatattaa  300
taaatcatat aaatagtcaa gtcttcaaat ataccctgac taatatttgc tagttaatta  360
tttattttct gattaattat tagccactgc taaacaataa gtcagtacga cccaaacaag  420
gcctagttac tactcctatc cataaaaaaa agttgtttga ccattttgac gccaaattta  480
accggcttat attaccaaaa tatttgaaaa aacattaaaa acagttgctg gttaaagtaa  540
attgtatgat aaactaaatc ggaatgaaaa taaataatag ttataatttt ttaataagat  600
gagccagtca aatttgacaa aaagttaaac cgatattctt tctggaacgg aaggagtaga  660
ctgtgttaat gttatgatat tgtgagcaag agagaagggg gtcgatagca acgacccaag  720
tgagtgggag gaggaaggtt ggggcgacga tgttgtgggg agggtgaagg atgatctaaa  780
taatattgtt cgctggattt gagtgagtaa gagcaacccc aacagtttag atataaatcc  840
tagctaaatt tagagtcttg ccaagagatt tttattttt caaaaaaata gtttattttt  900
ctttgggaaa tagaaatctc ttggaacaat agtgttttta aactagtctt ggcgtttgta  960
aagaagatag atagactcca attttttatg aagacgggtc aaaactcaac aaatcaacgg  1020
ataccgtccc ttttttggcg catgaagttt caggtctgta gcagccggcc cga         1073
```

```
SEQ ID NO: 12          moltype = DNA  length = 1106
FEATURE                Location/Qualifiers
source                 1..1106
                       mol_type = genomic DNA
                       note = A 1,106 nucleotide sequence representing the 3'
                        flanking corn genomic DNA after the inserted T-DNA.
                       organism = Zea mays
SEQUENCE: 12
actataacac agaggctggc caacctggag gcgcagcggc gccacaaggt ccagatctcg  60
ttcatcctgg ccacgttgct cgcgactccg aggacgtgca ggccactcgt cgtagctcta  120
cctcggcagc ctctgtcgcg actccgagga cgtgcaggcc gcgcagctcg cgcgctcctt  180
ccgtgccctc tccggttttg tgattccctg cgccctctcc ggcttcgccg ccgcatccgg  240
gtttacgtgg tggtgggcca ccgcagtccc accatccgcg aggcagccag cagggccccc  300
gcgctcgacg ataggctgct gaagcccctc gcccatcacc gtcttctggg gcgtgcctac  360
tgcgaggagg atggggtctt ccacaccatg ccacaaggtg ttcgacgctc gttccaactc  420
cgacgcgcag cctgtctgct cgcccatcac cggccacctg tctggacgcg cagcctgctg  480
cgtcaacatg ctcagcagca tcaactgctc aagaagctac accaacatca ctcctcttcc  540
tccacggggg actggattcg ccattggtac ctgctgcttc atgctcaacc aacacccttc  600
ttgccaagga tgatggagat tatatgaacc ggtgtttcag ttggtgttgg aagtccccat  660
ggttacatcc agatcagtcg gaatttagag acttcctcca atggtcttct tggcatttcc  720
```

```
aatttgtcag gtgcagagca tcacagttac caattccttg gccaccacct ataacattgc  780
gtttggttag agatgacctt gttgtgatgc cagtgattcc aagtatgcta ttgttatctc  840
agtgctattt cagtggagta gaatgtgtgc tgacaactat agatccatta ttttctaaat  900
tttgtgctga gagagagctg ttctggaagc caccttggca acctccagtt cctaacacca  960
gatctgagat accgttgttg atagagtttg tccatcttac tacaggagtc tgtgatactc  1020
tgcatatggt tactgaattt cctaagcaat actttgttgg cctgcttgtg ctgattacaa  1080
gggaattttt catgtctggg agaata                                        1106

SEQ ID NO: 13           moltype = DNA  length = 19612
FEATURE                 Location/Qualifiers
source                  1..19612
                        mol_type = other DNA
                        note = A 19,612 nucleotide sequence representing the
                         transgene cassette comprised within the binary plasmid
                         transformation vector used to transform corn to produce
                         corn event MON95275.
                        organism = synthetic construct
SEQUENCE: 13
aggatttttc ggcgctgcgc tacgtccgcg accgcgttga gggatcaagc cacagcagcc  60
cactcgacct tctagccgac ccagacgagc caagggatct tttggaatg ctgctccgtc  120
gtcaggcttt ccgacgtttg ggtggttgaa cagaagtcat tatcgcacgg aatgccaagc  180
actcccgagg ggaaccctgt ggttggcatg cacatacaaa tggacgaacg gataaacctt  240
ttcacgccct tttaaatatc cgattattct aataaacgct cttttctctt aggtttaccc  300
gccaatatat cctgtcaaac actgatagtt tcccggtaac tataacggtc ctaaggtagc  360
gacttaggct gagcccgggc aggcctaccc ataataccca taatagctgt ttgccaatcg  420
ttcttcttgg cgcgccgttg tcaatcaatt ggcaagtcat aaaatgcatt aaaaaatatt  480
ttcatactca actacaaatc catgagtata actataatta taaagcaatg attagaatct  540
gacaaggatt ctggaaaatt acataaagga aagttcataa atgtctaaaa cacaagagga  600
catacttgta ttcagtaaca tttgcagctt ttctaggtct gaaaatatat ttgttgccta  660
gtgaataagc ataatggtac aactacaagt gttttactcc tcatattaac ttcggtcatt  720
agaggccacg atttgacaca tttttactca aaacaaaatg tttgcatatc tcttataatt  780
tcaaattcaa cacacaacaa ataagagaaa aaacaaataa tattaatttg agaatgaaca  840
aaaggaccat atcattcatt aactcttctc catccatttc catttcacag ttcgatagcg  900
aaaaccgaat aaaaaacaca gtaaattaca agcacaacaa atggtacaag aaaaacagtt  960
ttcccaatgc cataatactc aaactcagta ggattctggt gtgtgcgcaa tgaaactgat  1020
gcattgaact tgacgaacgt tgtcgaaacc gatgatacga acgaaagcta ggcctcagcg  1080
agtaccgctg gcgatctaat ccatgatatc gtgaacatca tctacattca aattcttatg  1140
agctttctta agggcatctg cagcattttt catagaatct aatacagcag tatttgtgct  1200
agctccttcg agggcttccc tctgcatttc aatagttgta agggttccat ctatttgtag  1260
ttgggtcttt tccaatcgtt tcttctttt gagggcttgg agtgcaactc ttttattttt  1320
cgacgcattt ttctttgcgc tcctgcaggc ggccgcgtgg atgaggagtt aatcggtcgt  1380
gtgagagtag tgatcgagtg gatgtcgtcg agagtgatga gtgttgatgt tgttagtgat  1440
atgtggtaga aggtatcgtg ataaagcgtt aacgcgatcg cagtacttgc aaagaaaaat  1500
gcgtcgaaaa ataaaagagt tgcactccaa gccctcaaaa agaagaaacg attggaaaag  1560
acccaactac aaatagatgg aacccttaca actattgaaa tgcagaggga agccctcgaa  1620
ggagctagca caaatactgc tgtattagat tctatgaaaa atgctgcaga tgcccttaag  1680
aaagctcata agaatttgaa tgtagatgat gttcacgata tcatggatgg tatcgcacag  1740
cgactgctga gggacgtcga gctcccgctt ggtatctgca ttacaatgaa atgagcaaag  1800
actatgtgag taacactggt caacactagg gagaaggcat cgagcaagat acgtatgtaa  1860
agagaagcaa tatagtgtca gttggtagat actagatacc atcaggaggt aaggagagca  1920
acaaaaagga aactctttat ttttaaattt tgttacaaca aacaagcaga tcaatgcatc  1980
aaaatactgt cagtacttat ttcttcagac aacaatattt aaaacaagtg catctgatct  2040
tgacttatgg tcacaataaa ggagcagaga taaacatcaa aatttcgtca tttatattta  2100
ttccttcagg cgttaacaat ttaacagcac acaaacaaaa acagaatagg aatatctaat  2160
tttggcaaat aataagctct gcagacgaac aaattattat agtatcgcct ataatatgaa  2220
tccctatact attgacccat gtagtatgaa gcctgtgcct aaattaacag caaacttctg  2280
aatccaagtg ccctataaca ccaacatgtg cttaaataaa taccgctaag caccaaatta  2340
cacatttctc gtattgctgt gtaggttcta tcttcgtttc gtactaccat gtccctatat  2400
tttgctgcta caaaggacgg caagtaatca gcacaggcag aacacgattt cagagtgtaa  2460
ttctagatcc agctaaacca ctctcagcaa tcaccacaca agagagcatt cagagaaacg  2520
tggcagtaac aaaggcagag ggcggagtga gcgcgtaccg aagacggtcg tacggaaaat  2580
agagagagat agatttgtag agagagactg gtgatttcag cgtgtcctct ccaaatgaaa  2640
tgaacttcct tatatagagg aagagtcttg cgaaggatag tgggattgtg cgtcatccct  2700
tacgtcagtg gagatatcac atcaatccac ttgctttgaa gacgtggttg gaacgtcttc  2760
tttttccacg atgctcctcg tgggtggggg tccatctttg ggaccactgt cggcagaggc  2820
atcttgaacg atagcctttc ctttatcgca atgatggact ttgtaggagc caccttcctt  2880
ttctactgtc ctttccatga agtgacagat agatgggcaa tggaatccga ggaggtttcc  2940
tgatattacc ctttgttgaa aagtctcaat agccctttgg tcttctgaga ctgtatcttt  3000
gatattcttg gagtagacga gagtgtcgtg ctccaccatg ttgacgaaga ttttcttctt  3060
gtcattgagt cgtaaaagac tctgtatgaa ctgtccgcca gtcttcacgg cgagttctgt  3120
tagatcctcg atctgaattt ttgactcctt gctgatggac ggtgtggagg gaggtgcttt  3180
cgtgcttggc ggcatgcacg ggtaatcggc aacgcatgtg tgctttgagc gttgcctggt  3240
tgtcatggga tacaggacaa caaccatcgt catgtggaga tcgatcgaga tataggatcg  3300
gagcaagttg acaaatcatg tcaaaatcac tcaacgaggt agcatgttgt ataaacagat  3360
caatgcagaa atacattagt gctagctgga attgttccga tcagctggcg ctattattat  3420
tttatcgaaa ctgatgcgtg tgcgtgctcg ccttattttg tgttctgcgg gggcggctcc  3480
cgcgaatacc tattatttct gtgagcgctc ccttcaaaag tgacatgatt ttatatatcc  3540
ctctacgata cgacgaccag atcaagctac cactaccacc gaaatcagga cctctgctaa  3600
ccggtggccc agaccggaca aaagttattg cattgtatat gggtagggtt tatgtccatt  3660
```

-continued

```
ttacatcgcg catagtacgc acaatttctg ttggcccatc aatatatacc gagtgtgctg  3720
cagcctatag tgatagagtt ttacttaatt ctaagcctag gatccgaaca gtgattggaa  3780
atccttagtt acagtctgac agtataaagg tcactctcac tacctggtag tagagccatg  3840
acccggtgct gatatcacta tcaggtacag ccataaccac agtgctagtg gaaatatcac  3900
tacgtactag gccaatctat aatctgatga gaacacatat agttgacata gtcgatacgt  3960
acccatgtta tgagtcccga gtgactgtca aggacatgat ttgagttttg gtaagtgtgt  4020
gttggacaaa tcgaagcatg agtagggttc atggcctgtg atttgtacta gtctaactaa  4080
ctaaattatc gtgtacaacc gttgatctga gagggtcccg cgctgcaaat ctattgtaat  4140
actccctgtc gtaatactgt gttaatttgt gctcagtcgg acggctcaga ctttacggtg  4200
atataaacct ttactgagct gaactcgacc tggagatcga atcgaccccg caggtgttcc  4260
gaagcgtacc acggcgagcg ttaggtctaa gcaaaagcca caccccttcac agaacgaagg  4320
agtttcgcga agtcacgctg atttaaaaag agcgggccac tttttccact cttggtcaac  4380
agaaaaaggc ggacgagttc agatttaagg ccagctgcac gccgatcagc agattcgacg  4440
ttacccgcgg agagaaggct gcctgctact tcccagtcga aagtggtgta gttcaagtga  4500
tctctaaagc taaggctccg ctggtcctag tcgttaatta ccgagcagct ctccggcgta  4560
cagaaccacg aagttacttc ttgaggtgaa gcgtaagtgg tggtgagggt aagtagttgg  4620
aagcagaagc cttaagtgat acaatctggc ttccaccttg tcggaactcg ttaaaatttc  4680
ccttgattac aatataagta cctgcctgat cgttctggta gcctgatcga tttttatttt  4740
tgggctacgg gcaattgctc gcaatttatt gaagtcgcac gggcgcgaaa gaagacgttg  4800
ttctctctgc ttgctagaag ccgcggataa gcgattctat ccgatattta agacccgtgt  4860
agaccagcag acgtgagtgg gccgtttcca gaaaccgtct ctccttgcga cgatagatcc  4920
gatagtaagt aacttcaccc ctgatcaacg gcgtagtcgc ctgtctggtt cggatctgta  4980
tagatttggc ggattccgct tgcgaaatct ttagcagctt aggtccggag cccccggtgg  5040
atctggctgt tcagcggcac ggtccaatct ccttagctcc tctgtgaaca gcagtcgaac  5100
tctaagattc ttgatacgcg caacacgggc cttggcgagc ctggggataa ctcgcgagga  5160
cgctctcgcc gcgctaaagc gtgcgatcac accgctccga caagtgactt tgccaaatct  5220
agaaagagag actacactgc ttgccggtgc agtcttgatc caccttggag gggctgacgc  5280
taactaacta aggcgcgccg gcctactagg cctcgaccct tgttcgtcac tgctgacgtc  5340
tttttctcca ttattggagg atgagtcact gcaagctgta aagcttgtat tattgctagt  5400
ggaggcccca cctgcacatg ccgagcaatt atgattgtcg gccagtagct ttttgagctg  5460
tttgcagagc aataacttag tggatgtccc caccattaca tcgttattga tgatgctttc  5520
ttcaaaggaa gataagatgc tgacatcctg tctggagatt gtcgctccat agtgactcgt  5580
gatcaatact ctttcatgtg agtaattgat ttttatcttt gtttctccgt tgatggccta  5640
ctaggccaaa tggatgaaac aacttggacc aatcagagat ggccacgtca gctcccgatc  5700
gtcgtaaccg accaaacccg atcgataacg gtttaggctc caatacaccg tcggtaccac  5760
ccggtcgcta tcatctgccc ccgtcccaac gctattggta tcgtccgccc ctatatcggt  5820
cggtagccca gtccaccgtc ggggccaatc gtcccctgct gcgtccgctc gtgtcggtac  5880
cgatcgccaa aaacgccacg tcaacggcac tgcggtaccg accgccgctg gcaccggcct  5940
tagcgggcca cacgaccgat cgctgttgta cggacgtaga ggtgaatcat gcgattgaat  6000
tttcgctaga ggaaagttat catcttatta tctccaaccc tccttcctac ggctggatcc  6060
gacgaaaatt taccctggac ggtgccagta acaattgcag gtctcactca cgtgctaaat  6120
ccagcaatca aacacgaagg aatatacgtg atctggccag aacatgcaag agaataatac  6180
agtagtgtta gagtacgaaa cctacacgat tcaacgaatt aatcaatggg ttcacgttca  6240
cgggtatgct cgcgcacgtc caaaatccaa cgacattttt ataagcggca tgatccagac  6300
gggccagctc gagcaccaca tggcgtggct ccatctcgca tcccccatca ccgctataaa  6360
taccattggc catgcacacc cgcactccca cacagcacaa gcagcagcag cagcagcagc  6420
tcgatcgaac tagcttagct actacgtgcg cgtgcaacaa gcagctcgat cgatcgccct  6480
cacggtaatt tcttctccca aaataaacct aatctttaat ctgttgcctg tctactcttc  6540
ctatctgttg ctaaaaattt gaatttggta tgtgcaggag gacttaatta agggacccac  6600
cgccatgtca tccacggacg tgcaagagcg cctgcgggac ttggcgcgcg aagacgaggc  6660
gggaacgttc aacgaggctt ggaacaccaa cttcaagccg tcggacgagc agcaattcag  6720
ctactcgccg acggagggaa ttgtcttcct cacgccgcct aagaacgtca tcggtgagcg  6780
gcgcatctcc cagtacaagg tgaacaatgc ctgggcaact ctggagggct ctcccaccga  6840
ggcgagcggt acgccgttgt acgcgggcaa gaatgtactg gacaactcga aaggcacaat  6900
ggaccaggag ttgcttacac ccgagttcaa ctacacctac acggagagca cgagcaacac  6960
gacgacgcac ggcctcaaac tcggcgtgaa gaccaccgcg accatgaagt tccctatcgc  7020
tcaaggctcg atggaggcga gcaccgagta caatttccag aactcctcca ccgataccaa  7080
gaccaaacaa gtgtcttaca agtctccgag ccagaagatt aaggttcctg cgggcaagac  7140
gtaccgcgtg ctggcgtacc tgaacaccgg ctctatctct ggcgaggcta acctgtacgc  7200
gaacgtcggc ggcatcgcgt ggcgggtctc gccaggctat cctaacggcg gcggcgtgaa  7260
catcggcgct gtcctgacca agtgccagca gaagggttgg ggcgacttcc gcaacttcca  7320
gccctccggg cgcgacgtca tcgtgaaggg tcagggcacc ttcaagtcca actacggcac  7380
cgacttcatc cttaagattg aggacatcac cgacagcaag ctccgcaaca acaacggctc  7440
cgggacggtc gtacaggaga tcaaggtgcc actcatccgc accgagattt gataggggtc  7500
cccggtccga tgaagtgcca tcatgccatg gatgcggggt gaaagctcgc ggcgtcgaat  7560
ataatctccg gttccagttt cagctactat ggcgactcgt gtcgtgtgtg tgtggttact  7620
ctgcttttgt atgtttggta atggtgtgtg cgctgttgtc cagagtttca tggtggtact  7680
gcttcctagc agtgttgtgt actagtctcg gtactttgcc tgtatgttga gctcggctca  7740
gtatgttctg ggagtgaata aataaaaata aaaaaaacca gatattgtag tatactaact  7800
gccgttgctc tgtttcatcc acatacacag aatcctatga actgatcttt gtggggactt  7860
gggagccatc tgctcggatc ttcttcatgg gattctctca atttctcctc atttttctaa  7920
ggctgtgtgt ttagatgtag ggagaaaagt ttttggattg tacatcgtgt tgggtactaa  7980
tttagtctac tactccgtcc gtgaatagat gacattttct ttcggtgttg ttcgtcgtgc  8040
cacaaagttt tgaatttatt tatatgcaat cctgcaggtg tttaaacacc tgcaggtctg  8100
catgttcagt tagcacaagc aggttgcagc ttcaccaaac acatacagtc ggccattgct  8160
gcttcaccaa acataaacac tacctgttgg agctacacca aacacttgca ctgaccaaag  8220
aacattaata gatcatcagg actgttcaag taatcacgca tgacaagata gaaagcagca  8280
ggtccccttc cttctcaaag tagcctgcag cttcattctt tggttcacca ttacataaac  8340
agcaaaacca gaaatagcag acaataattc ctcctctagg taaataacca gacacagtaa  8400
```

```
taccctcaca agtaccactt attaggacag tacaatacaa atgatagcaa ggggcagatc  8460
aagaatcaca acacagaagc cacaaaacat gataagcgca gcagaccaaa agcttcttct  8520
caaagggcgc ccggaccgtc agttgttggt ctggctgtac atgacatccg acttctgaat  8580
ccacttgtgt agcaccttca ggtccttccc gccgaccgtc gcccagagct ctacgctagc  8640
atctttcgtc gggtaggtcc cgccgttagg gttcttgaga ttaaacgtaa tctggaacaa  8700
gaacgggctc ggcttgctga cggtctggac cttcttgccg ttcacgcgga tcttgtagct  8760
cgacacgttg ttgtagaaga tgtcgggcag cttgtacagg ctgaggccgg agtacaggtt  8820
tggattctct gagagatacc accagcctga gaatttgtgg gcgtcgatca taactttctc  8880
gatctcggac tcgccaagct cagcgacttt cactttgagg ttgtcgttct tctcgtcaac  8940
ggcgtagagc tccataggcg tgatcgcagt gatgctgccg tacgtcaccg tccgcttccc  9000
gttggcgtcc agaggcggcg cagggatgat gctaccgagg cggccgttga tcttccactg  9060
gtatcggatc ttgctactcg gcacgcgagt gaacgtggca ccgatcacca tctcgtcgtt  9120
ggagccgaag gaccacttct caaagatgtg tttcttctgc aggttctcgt tggtcttcca  9180
ctcgatcacg gagacatcgt cgaagtgcag gttggcgttc ccgttattct tcaggccgat  9240
gatcttgaag tattcagggt tattgaacgt gttgaaggag aactccgcta tcttccactt  9300
cccgccggtc accttcccgg aaaccttcgc gccttgcccg ttgccggagc tgttgtcagc  9360
gtagaagacg acctcgttgc tcccagtggt gctggcggtg cgcacgtacg cccgcacagt  9420
gtaggaggtg tatggcttca gctgcgggtt tgacatcgcc gtgccgtgcc cgtcagtgcc  9480
gatccgcccg cgcttcttgc cggtgtagcc tccggattct tggtaggtgt agtaccacag  9540
gttctctgag gtctcgaagt cgtagtactt gatcgggacg tgtagcgtga tcttcatgcc  9600
gcgcttccac ttcacgtcgt acaccgtctt gccgggcatc tggttcagct ggcgctcgat  9660
ttctttcttc gtgttctcgt ccgtgatgag gttgatggaa ggctcatcaa tgaagatgtc  9720
cttctcaccc tggtccgtgt agtacagtct gccgtccttc tcctgagcgt taaacgcctt  9780
cttgatggcc tccttgatgg tgatctccgg agtcttgtcc tccggatcgt tcatgttctt  9840
cgccgcgacc cggcgctcga ggctatcctt gcccgtgccg aggttaagag taaggctccc  9900
actgacagcg tcaatgtttg tccggatcgg gtcccactcg cctccgggta tcacctggcc  9960
tttctcgtcg aggataccgt actggccgcg gttctgcgta gtctcgatgt tgagaatctc  10020
cgtgcccgcc tggatcttgt ccagctgctc ggcgttgatc gctatcttca cggtgcccgc  10080
ctcgttggcc ttgtctaggg agataggagc ctggcccttc tgcggatagg tgtcgccggc  10140
accgagcgag ttgccgatct ggttagggcc ggcggtgatc gtggtgatgc tgtcgcctga  10200
gttctggaag acgaagttgg tggtcggctt caggtcgtag atgggcgcgg tgccaccatt  10260
gtaatagcgc acgttcgcgt tgagatacgc cctctcggca gtgttgatcc ctatctgcga  10320
actccaggta gtagagtcgg tgtcggccac acttgtggac gacgaccagc tgtgggtgta  10380
ctttggtgag attgagaaac tgaagccctt gtcgctgaag cccaggctgc cgccgatctc  10440
gacggtgttg gtcgtggtgt cggtcttagt tgtagtcttg ctctttgtat ccgcgttgcc  10500
ctccgtcacc gtatcgttct tgctgaagtg gagcttctcc attccgacgc caacggaggg  10560
ataggcggcc actagaggat cgcgcgcctc atacttcgta gcagcgggca tgtgcccagt  10620
caccttctcg aagtcggtgt acgggtcttt gaccgtacgg gcgtggtaag ggttgctcac  10680
gtacttcttg tagccttctg cactgtaggc gtcgttccac ggcacgatct gctggttacg  10740
gaaggtgtat cctttctctt cccattcatc agggatgcag tcgttgtcgg tgtccaccgg  10800
cgtggacatc gactgcttct cgccgttctc ttgctggcgg tcgaagaggt tgtagttcgg  10860
gaagaagctc tgggtctcct tctccgcgag agagttcgcc ttctcgctga aattcgggct  10920
cagtatgtac ttctccggga tctgttcctt ctgcgcgttg ttcatcgacc agaagagctg  10980
taggtccggc agggtgttgg aggtgttcct gtactcgatc ttaatctcgt agacctggtt  11040
tgcctctagt ttgaggttct tctggatgct cgcctggttg atgaccgtct cgccattgat  11100
ctggaggatt acgttctcgt cggaggatgt ggagaggcgg tactcgccgg tctgcgggct  11160
cttcaggttg cccatccacc gaatggactg gatctgctgg gcgtccgtgt tgatgcgagc  11220
cttgttcatg aggttggact tctcgcccac ctggatgaac atgagctcct tgaaggttga  11280
gtccttgaag tagaagccga ccaggccgat gaccgtcgct tgctcactct tggaggagac  11340
aatgttctgc atggtggtgg ccggccaagt aacggtccgc taccctgcaa gaggtagcaa  11400
aaaaggggta tcagttaaca gcaagtgtat cctgctagat agtagctgta caagggaacc  11460
agtaagcatc gtaaacataa aagttttgaa ggcatatcaa ctgaaccttt atatttgtgc  11520
atctataagt caataaaaac aacatatgta cagagcttac tgccaggcaa aagtgggatt  11580
catttcaccg actaggctaa tgttgtactc cctccgttcc aaattgtagg tcgttttgac  11640
ttttctagat tcatagatat tattatgcac ctagacatac actatatcta gatgcataat  11700
aatatctatg aacctacaaa agtcaaaacg acctacaatt tggaacggag agagtaagaa  11760
ataatctgat aacttgcgga ctgttgtttc caacatttat aaaaatgtgt aaagtaccat  11820
aaccaaacat tcgtataact aaacatgata ggaaaagact agcattgctt tgaaaaagta  11880
gtgtacatgt actggccaat ctaacaagct tttttgttgt ctaaaatgtg acctgcagag  11940
caacaaaaat cacatgctga acttttcagc ctaacatttg gtgccatgaa acatcactaa  12000
gttgtcacta attttgggtg gtatgtgctc aatagctatt catgacaagg aaacatccta  12060
acatgcagat atgctttcca aatagctctc tccgaatgaa ccacacacgg atttttacac  12120
tctggtagtt caatcacacc aaattaacta tccgcgactt tcatccaacc atgttaccag  12180
ttaccgcaac tatctggact tgctagacag agcatcacga agctctccca gactcccagt  12240
caagcaggaa actagaacgt cggagctggg aagtagtcaa gcagtcacac cccaagggct  12300
cgtgcatcgc cagcaacacg taagcgcatt caggcacatc acagtcacca ttcctaggta  12360
cgtagctcag agagcctcct cgcacggcag tcccgcaaac acacatcagg cgtgcgcaca  12420
aaatcagacg catcggcacg cagaaacgct acagatcagg aacaggacgg agttcatcaa  12480
gcacagacgt cagacgaaca ccctagcacc aaccacgaag cacgatccgc tggcggatcg  12540
cgcggtaccc gccccggatc tggcgggagc accggaggca agtgaccaga acgcatgagc  12600
aaaccgcaga tctcgagcca ggccgctcag atctgagcgc caaacactcg aaaaatgctg  12660
gagcaggagc tagtgcgtgg ggagatcgcg agtagagggg ctccagggag cggaggggag  12720
ggggaggagg agattaccgg ggaggccggc ctgctgcaga gtacagaaag cacttgcttg  12780
atcactagcg cgaagcagag gtgtgcctgc ccttagtatt aactgatcac taagcgcttg  12840
tgatggttcg tggtggcgct tgattgttgc atttatagga gaaccatcgg cgcagtgccg  12900
attattgtaa tagcagtgtt gttgtgtgag tttacattcc cgtgagcatg agtgcatgtg  12960
agggcgatta ttaattagat ggctgatcaa tgcagaacag cgcaagtggc caagattgct  13020
ccactggtgg atgcatgttg atgtttgttc tcgcttgatg gttgatcatt tttattcagt  13080
ttaggacgaa cttgtcatat gggttggctg cttgtatcta gtaacgtgat cgagtgctaa  13140
```

```
acatcagcag aggtatcatg gtgatgcatg gacggtggac gcccaagttg ttgaacagtt  13200
gaagtatttt tttttctgca cttcacggga tccaagcgca gagctatgca taattgcata  13260
tagcggtggg tacgggtgca cccttgcatg gtaaaactga atgcgctcag aaggcaattg  13320
caatcactaa aatttgcttt agctctgttc ctgatcgggt caaggtttat tatgttcagt  13380
tggaacattc aaagttagag gcttgaattt gcttaaaaag cattcccaca aacaacggtg  13440
ggtgcccttt ttgtatgacg tactgttggc tagatggttc cgcttgttta tgaaaaaaga  13500
gtgtactaat aaatttaccc gaactcttca ctaccgcaga taactctttt gccgagtgct  13560
tcatgcactt cacaaagtcc agaaaacact tggcaagctc caagcttaag aaacataaat  13620
gacgtgcata agttcaaaaa tagtttaata caagactaag atgtccaaaa gaacggtaaa  13680
ttatattaaa ataatacttc ttataataga tcaatgctat cgaatagccc acttcactct  13740
ttaagcatac ataaatttc aattatatca taaaatttct acgtcctact gcgtttcaac  13800
catatttcag catgacaatt atagtaatac aaaacaagaa ttgaattgct tgaatgtaaa  13860
tgttcaaagt aaagaaggat tattaatatg atgatgtttt atcgagatat cagagagtca  13920
acactcctca ttgatccttg ttagagcacc catgtaagtg tgtcgctccc ccttcatccg  13980
tgcaagcagg atcaaatgct ctctagaagg aacgtgggca tctaagagag ggatgaatcc  14040
gaacataact gggattttg gaggattctg atgaaaccat ttaccctaac ttgagataac  14100
tggagtaaaa gatccttact gtccaccatt tcttgtgatg ggttaaaatc cctcttgccg  14160
gagagaccta tctctatcag gtgatatgcc tggtagctgt ttccttcttc ccaatctggc  14220
aggcccttgt tcgtcactgc tgacgtcttt ttcctcatta ttggaggatg agtcactgca  14280
agctgtaaag cttgtattat tgctggtgga ggccccacct tcacatgctg agcatttatg  14340
gttgtcggcc aataatttct tcagctgttt gcaaagcaat aattttgtag atgtccctac  14400
atcaactttg gcatgtgcaa tgctttcttc aaaggaagat aagatgtcaa catcttgtct  14460
ggagattggt gctccgtagt gactcatgat caataccttt ttctgtgcgt aattgatctt  14520
gatttttgtc ttcccgtcga tggcgcgcca agaagaacga ttggcaaaca gctattatgg  14580
gtattatggg taggcctgcc caaactaggg ataacagggt aataggtctc acgcggcaaa  14640
tcctaccacc tcatttaaat agagtgaggt tgatttgcgg ccgctataac ttcgtataat  14700
gtatgctata cgaagttatc ctagggacaa caacatgctt ctcatcaaca tggagggaag  14760
agggagggag aaagtgtcgc ctggtcacct ccattgtcac actagccact ggccagctct  14820
cccacaccac caatgccagg ggcgagcttt agcacagcca ccgcttcacc tccaccaccg  14880
cactacccta gcttcgccca acagccaccg tcaacgcctc ctctccgtca acataagaga  14940
gagagagaag aggagagtag ccatgtgggg aggaggaata gtacatgggg cctaccgttt  15000
ggcaagttat tttgggttgc caagttaggc caataagggg agggatttgg ccatccggtt  15060
ggaaaggtta ttggggtagt atctttttac tagaattgtc aaaaaaaaat agtttgagag  15120
ccatttggag aggatgttgc ctgttagagg tgctcttagg acatcaaatt ccataaaaac  15180
atcagaaaaa ttctctcgat gaagatttat aaccactaaa actgccctca attcgaaggg  15240
agttcaaaac aattaaaatc atgttcgaat tgagtttcaa tttcacttta accccttga  15300
aatctcaatg gtaaaacatc aacccgtcag gtagcatggt tctttttatt cctttcaaaa  15360
agagttaatt acaaacagaa tcaaaactaa cagttaggcc caaggcccat ccgagcaaac  15420
aatagatcat gggccaggcc tgccaccacc ctccccctcc tggctcccgc tcttgaattt  15480
caaaatccaa aaatatcggc acgactggcc gccgacggag cgggcggaaa atgacggaac  15540
aacccctcga attctacccc aactacgccc accaacccac acgccactga caatccggtc  15600
ccacccttgt gggcccacct acaagcgaga cgtcagtcgc tcgcagcaac cagtgggccc  15660
acctcccagt gagcggcggg tagatctgga ctcttaccca cccacactaa acaaaacggc  15720
atgaatattt tgcactaaaa ccctcagaaa aattccgata ttccaaacca gtacagttcc  15780
tgaccgttgg aggagccaaa gtggagcgga gtgtaaaatt gggaaactta atcgaggggg  15840
ttaaacgcaa aaacgccgag gcgcctcccg ctctatagaa aggggaggag tgggaggtgg  15900
aaaccctacc acaccgcaga gaaaggcgtc ttcgtactcg cctctctccg cgccctcctc  15960
cgccgccgct cgccgccgtt cgtctccgcc gccaccggct agccatccag gtaaaacaaa  16020
caaaaacgga tctgatgctt ccattcctcc gtttctcgta gtagcgcgct tcgatctgtg  16080
ggtggatctg ggtgatcctg gggtgtggtt cgttctgttt gatagatctg tcggtggatc  16140
tggccttctg tggttgtcga tgtccggatc tgcgttttga tcagtggtag ttcgtggatc  16200
tggcgaaatg ttttggatct ggcagtgaga cgctaagaat cgggaaatga tgcaatatta  16260
ggggggtttc ggatggggat ccactgaatt agtctgtctc cctgctgata atctgttcct  16320
ttttggtaga tctggttagt gtatgtttgt ttcggataga tctgatcaat gcttgtttgt  16380
tttttcaaat tttctaccta ggttgtatag gaatggcatg cggatctggt tggattgcca  16440
tgatccgtgc tgaaatgccc ctttggttga tggatcttga tattttactg ctgttcacct  16500
agatttgtac tcccgtttat acttaatttg ttgcttatta tgaatagatc tgtaacttag  16560
gcacatgtat ggacggagta tgtggatctg tagtatgtac attgctgcga gctaagaact  16620
atttcagagc aagcacagaa aaaaatattt agacagattg ggcaactatt tgatggtctt  16680
tggtatcatg ctttgtagtg ctcgtttctg cgtagtaatc ttttgatctg atctgaagat  16740
aggtgctatt atattcttaa aggtcattag aacgctatct gaaaggctgt attatgtgga  16800
ttggttcacc tgtgactccc tgttcgtctt gtcttgataa atcctgtgat aaaaaaaatt  16860
cttaaggcgt aatttgttga aatcttgttt tgtcctatgc agcctgatcc atggcgcaag  16920
ttagcagaat ctgcaatggt gtgcagaacc catctcttat ctccaatctc tcgaaatcca  16980
gtcaacgcaa atctccctta tcggtttctc tgaagacgca gcagcatcca cgagcttatc  17040
cgatttcgtc gtcgtgggga ttgaagaaga gtgggatgac gttaattggc tctgagcttc  17100
gtcctcttaa ggtcatgtct tctgtttcca cggcgtgcat gcttcacggt gcaagcagcc  17160
ggcccgcaac cgcccgcaaa tcctctggcc tttccggaac cgtccgcatt cccggcgaca  17220
agtcgatctc ccaccggtcc ttcatgttcg gcggtctcgc gagcggtgaa acgcgcatca  17280
ccggccttct ggaaggcgag gacgtcatca atacgggcaa ggccatgcag gcgatgggcg  17340
cccgcatccg taaggaaggc gacacctgga tcatcgatgg cgtcggcaat ggcggcctcc  17400
tggcgcctga ggcgccgctc gatttcggca atgccgccac gggctgccgc ctgacgatgg  17460
gcctcgtcgg ggtctacgat ttcgacagca ccttcatcgg cgacgcctcg ctcacaaagc  17520
gcccgatggg ccgcgtgttg aacccgctgc gcgaaatggg cgtgcaggtg aaatcggaag  17580
acggtgaccg tcttcccgtt accttgcgcg ggccgaagac gccgacgccg atcacctacc  17640
gcgtgccgat ggcctccgca caggtgaagt ccgccgtgct gctcgccggc ctcaacacgc  17700
ccggcatcac gacggtcatc gagccgatca tgacgcgcga tcatacggaa aagatgctgc  17760
agggctttgg cgccaacctt accgtcgaga cggatgcgga cggcgtgcgc accatccgcc  17820
tggaaggccg cggcaagctc accggccaag tcatcgacgt gccgggcgac ccgtcctcga  17880
```

-continued

```
cggccttccc gctggttgcg gccctgcttg ttccgggctc cgacgtcacc atcctcaacg  17940
tgctgatgaa ccccacccgc accggcctca tcctgacgct gcaggaaatg ggcgccgaca  18000
tcgaagtcat caacccgcgc cttgccggcg gcgaagacgt ggcggacctg cgcgttcgct  18060
cctccacgct gaagggcgtc acggtgccgg aagaccgcgc gccttcgatg atcgacgaat  18120
atccgattct cgctgtcgcc gccgccttcg cggaaggggc gaccgtgatg aacggtctgg  18180
aagaactccg cgtcaaggaa agcgaccgcc tctcggccgt cgccaatggc ctcaagctca  18240
atggcgtgga ttgcgatgag ggcgagacgt cgctcgtcgt gcgtggccgc cctgacggca  18300
aggggctcgg caacgcctcg ggcgccgccg tcgccaccca tctcgatcac cgcatcgcca  18360
tgagcttcct cgtcatgggc ctcgtgtcgg aaaaccctgt cacggtggac gatgccacga  18420
tgatcgccac gagcttcccg gagttcatgg acctgatggc cgggctgggc gcgaagatcg  18480
aactctccga tacgaaggct gcctgatgag ctccagggtt cttgcctggt gccttggcaa  18540
tgcttgatta ctgctgctat cctatgatct gtccgtgtgg gcttctatct atcagtttgt  18600
gtgtctggtt ttgaaaaaca tttgcttttc gattatgtag ggtttgcttg tagctttcgc  18660
tgctgtgacc tgtgttgttt atgtgaacct tctttgtggc atctttaata tccaagttcg  18720
tggtttgtcg taaaacgaag cctctacttc gtaaagttgt gtctatagca ttgaaatcgt  18780
ttttttgctc gagaataatt gtgaccttta gttggcgtga aactagtttt ggatatctga  18840
ttctctggtt cgcaatcttg agatcgtcgc tgcttaggtg agctaagtga tgttcctaag  18900
taaatgctcc tcaccagaat acgtagctgt gtgaaaagag aacgcgtgaa tacgtagctg  18960
tgtaaagatt gtgtcccaag taaacctcag tgatttttgt ttggattttt aatttagaaa  19020
cattcgactg ggagcggcta gagccacacc caagttccta actatgataa agttgctctg  19080
taacagaaaa caccaactag tataacttcg tataatgtat gctatacgaa gttatgtcga  19140
ctcgtggtgg ccgcatcgat cgtgaagttt ctcatctaag cccccatttg gacgtgaatg  19200
tagacacgtc gaaataaaga tttccgaatt agaataattt gtttattgct ttcgcctata  19260
aatacgacgg atcgtaattt gtcgttttat caaaatgtac tttcatttta taataacgct  19320
gcggacatct acatttttga attgaaaaaa aattggtaat tactctttct ttttctccat  19380
attgaccatc atactcattg ctgatccatg tagatttccc ggacatgaag ccatttacaa  19440
ttgaatatat cctgccgccg ctgccgcttt gcacccggtg gagcttgcat gttggtttct  19500
acgcagaact gagccggtta ggcagataat ttccattgag aactgagcca tgtgcacctt  19560
ccccccaaca cggtgagcga cggggcaacg gagtgatcca catgggactt tt          19612
```

```
SEQ ID NO: 14          moltype = DNA  length = 35
FEATURE                Location/Qualifiers
source                 1..35
                       mol_type = other DNA
                       note = A 35 nucleotide sequence representing the LoxP sites
                        used for Cre-mediated excision and recombination.
                       note = Enterobacteria phage P1
                       organism = Punavirus P1
SEQUENCE: 14
tataacttcg tataatgtat gctatacgaa gttat                          35

SEQ ID NO: 15          moltype = DNA  length = 27
FEATURE                Location/Qualifiers
source                 1..27
                       mol_type = other DNA
                       note = A 27 nucleotide sequence corresponding to a thermal
                        amplification primer referred to as SQ20267 used to
                        identify corn event MON95275 DNA in a sample.
                       organism = synthetic construct
SEQUENCE: 15
ctctttcttt ttctccatat tgaccat                                   27

SEQ ID NO: 16          moltype = DNA  length = 24
FEATURE                Location/Qualifiers
source                 1..24
                       mol_type = other DNA
                       note = A 24 nucleotide sequence corresponding to a thermal
                        amplification primer referred to as SQ51355 used to
                        identify corn event MON95275 DNA in a sample.
                       organism = synthetic construct
SEQUENCE: 16
gttggccagc ctctgtgtta tagt                                      24

SEQ ID NO: 17          moltype = DNA  length = 19
FEATURE                Location/Qualifiers
source                 1..19
                       mol_type = other DNA
                       note = A 19 nucleotide sequence corresponding to a probe
                        referred to as PB10263 used to identify corn event
                        MON95275 DNA in a sample.
                       organism = synthetic construct
SEQUENCE: 17
atactcattg ctgatccat                                            19

SEQ ID NO: 18          moltype = DNA  length = 24
FEATURE                Location/Qualifiers
source                 1..24
                       mol_type = other DNA
                       note = A 24 nucleotide sequence corresponding to a thermal
```

```
                      amplification primer referred to as SQ20222 used as an
                      internal control for the event and zygosity assay for corn
                      event MON95275.
                     organism = synthetic construct
SEQUENCE: 18
gccctatgac ttaccgagag ttca                                         24

SEQ ID NO: 19        moltype = DNA  length = 28
FEATURE              Location/Qualifiers
source               1..28
                     mol_type = other DNA
                     note = A 28 nucleotide sequence corresponding to a thermal
                      amplification primer referred to as SQ20221 used as an
                      internal control for the event and zygosity assay for corn
                      event MON95275.
                     organism = synthetic construct
SEQUENCE: 19
gttgctatgt actaacagaa ctgcatgt                                     28

SEQ ID NO: 20        moltype = DNA  length = 17
FEATURE              Location/Qualifiers
source               1..17
                     mol_type = other DNA
                     note = A 17 nucleotide sequence corresponding to a probe
                      referred to as PB50298 used as an internal control for the
                      event and zygosity assay for corn event MON95275.
                     organism = synthetic construct
SEQUENCE: 20
ttgttgtgtg gctccat                                                 17

SEQ ID NO: 21        moltype = DNA  length = 20
FEATURE              Location/Qualifiers
source               1..20
                     mol_type = other DNA
                     note = A 20 nucleotide sequence corresponding to a thermal
                      amplification primer referred to as PNEG95275_F used in
                      the zygosity assay for corn event MON95275.
                     organism = synthetic construct
SEQUENCE: 21
tctctttctt ccacctcacg                                              20

SEQ ID NO: 22        moltype = DNA  length = 20
FEATURE              Location/Qualifiers
source               1..20
                     mol_type = other DNA
                     note = A 20 nucleotide sequence corresponding to a thermal
                      amplification primer referred to as PNEG95275_R used in
                      the zygosity assay for corn event MON95275.
                     organism = synthetic construct
SEQUENCE: 22
cgaatgcctc tgataccaat                                              20

SEQ ID NO: 23        moltype = DNA  length = 17
FEATURE              Location/Qualifiers
source               1..17
                     mol_type = other DNA
                     note = A 17 nucleotide sequence corresponding to a probe
                      referred to as PRBNEG95275 used in the zygosity assay for
                      corn event MON95275.
                     organism = synthetic construct
SEQUENCE: 23
gtaccgcaac gctaaca                                                 17

SEQ ID NO: 24        moltype = DNA  length = 496
FEATURE              Location/Qualifiers
source               1..496
                     mol_type = other DNA
                     note = An enhancer that is a re-arrangement of fragments
                      derived from Dahlia mosaic virus with altered nucleotides.
                     organism = synthetic construct
SEQUENCE: 24
atcgacggga agacaaaaat caagatcaat tacgcacaga aaaaggtatt gatcatgagt  60
cactacggag caccaatctc cagacaagat gttgacatct tatcttcctt tgaagaaagc  120
attgcacatg ccaaagttga tgtagggaca tctacaaaat tattgctttg caaacagctg  180
aagaaattat tggccgacaa ccataaatgc tcagcatgtg aaggtggggc ctccaccagc  240
aataatacaa gctttacagc ttgcagtgac tcatcctcca ataatgagga aaaagacgtc  300
agcagtgacg aacaagggcc tgccagattg ggaagaagga aacagctacc aggcatatca  360
cctgatagag ataggtctct ccggcaagag ggattttaac ccatcacaag aaatggtgga  420
cagtaaggat cttttactcc agttatctca agttagggta aatggtttca tcagaatcct  480
```

-continued

```
ccaaaaatcc cagtta                                                496

SEQ ID NO: 25          moltype = DNA  length = 576
FEATURE                Location/Qualifiers
source                 1..576
                       mol_type = other DNA
                       note = A promoter operably linked to a leader derived from
                        Cauliflower mosaic virus isolate NY8153, wherein
                        nucleotide position 2 has been altered to change a
                        potential start codon.
                       organism = synthetic construct
SEQUENCE: 25
aaggagtcaa aaattcagat cgaggatcta acagaactcg ccgtgaagac tggcggacag  60
ttcatacaga gtcttttacg actcaatgac aagaagaaaa tcttcgtcaa catggtggag  120
cacgacactc tcgtctactc caagaatatc aaagatacag tctcagaaga ccaaagggct  180
attgagactt ttcaacaaag ggtaatatca ggaaacctcc tcggattcca ttgcccatct  240
atctgtcact tcatggaaag gacagtagaa aaggaaggtg gctcctacaa agtccatcat  300
tgcgataaag gaaaggctat cgttcaagat gcctctgccg acagtggtcc caaagatgga  360
cccccaccca cgaggagcat cgtggaaaaa gaagacgttc caaccacgtc ttcaaagcaa  420
gtggattgat gtgatatctc cactgacgta agggatgacg cacaatccca ctatccttcg  480
caagactctt cctctatata aggaagttca tttcatttgg agaggacacg ctgaaatcac  540
cagtctctct ctacaaatct atctctctct attttc                          576

SEQ ID NO: 26          moltype = DNA  length = 322
FEATURE                Location/Qualifiers
source                 1..322
                       mol_type = unassigned DNA
                       note = An enhancer derived from Dahlia mosaic virus.
                       organism = Dahlia mosaic virus
SEQUENCE: 26
atcaacggag aaacaaagat aaaaatcaat tactcacatg aaagagtatt gatcacgagt  60
cactatggag cgacaatctc cagacaggat gtcagcatct tatcttcctt tgaagaaagc  120
atcatcaata acgatgtaat ggtggggaca tccactaagt tattgctctg caaacagctc  180
aaaaagctac tggccgacaa tcataattgc tcggcatgtg caggtggggc ctccactagc  240
aataatacaa gctttacagc ttgcagtgac tcatcctcca ataatggaga aaaagacgtc  300
agcagtgacg aacaagggtc ga                                         322
```